US010093907B2

(12) United States Patent
Meulewaeter et al.

(10) Patent No.: US 10,093,907 B2
(45) Date of Patent: Oct. 9, 2018

(54) HETERO-TRANSGLYCOSYLASE AND USES THEREOF

(71) Applicants: Bayer CropScience NV, Diegem (BE); The University Court of the University of Edinburgh, Edinburgh (GB)

(72) Inventors: Frank Meulewaeter, Merelbeke (BE); Ilse Van Den Brande, Welle (BE); Stephen C. Fry, Edinburgh (GB); Kyle E. Mohler, Zionsville, IN (US); Lenka Frankova, Edinburgh (GB); Tom J. Simmons, Lancashire (GB); Claire Holland, Manchester (GB); Andrew Hudson, Midlothian (GB)

(73) Assignee: BASF SE, Ludwigshafen am Rhein (DE)

( * ) Notice: Subject to any disclaimer, the term of this patent is extended or adjusted under 35 U.S.C. 154(b) by 53 days.

(21) Appl. No.: 15/023,153

(22) PCT Filed: Sep. 24, 2014

(86) PCT No.: PCT/EP2014/070381
§ 371 (c)(1),
(2) Date: Mar. 18, 2016

(87) PCT Pub. No.: WO2015/044209
PCT Pub. Date: Apr. 2, 2015

(65) Prior Publication Data
US 2016/0230150 A1 Aug. 11, 2016

(30) Foreign Application Priority Data

Sep. 24, 2013 (EP) .................................... 13185727
Nov. 8, 2013 (EP) .................................... 13192054

(51) Int. Cl.
| | | |
|---|---|---|
| *C12N 15/82* | (2006.01) | |
| *C12N 9/10* | (2006.01) | |
| *C08L 1/02* | (2006.01) | |
| *D06M 16/00* | (2006.01) | |
| *C08B 1/00* | (2006.01) | |
| *C08B 37/00* | (2006.01) | |
| *C08H 8/00* | (2010.01) | |
| *D06M 15/03* | (2006.01) | |
| *C12P 19/04* | (2006.01) | |
| *C12P 19/18* | (2006.01) | |

(52) U.S. Cl.
CPC ............. *C12N 9/1051* (2013.01); *C08B 1/00* (2013.01); *C08B 37/0057* (2013.01); *C08H 8/00* (2013.01); *C08L 1/02* (2013.01); *C12N 15/8246* (2013.01); *C12P 19/04* (2013.01); *C12P 19/18* (2013.01); *C12Y 204/01207* (2013.01); *D06M 15/03* (2013.01); *D06M 16/003* (2013.01)

(58) Field of Classification Search
CPC .. C12N 9/1051; C12N 15/82; C12N 15/8242; C12N 15/8261
See application file for complete search history.

(56) References Cited

U.S. PATENT DOCUMENTS

| | | | |
|---|---|---|---|
| 4,761,373 A | 8/1988 | Anderson et al. | |
| 4,962,028 A | 10/1990 | Bedbrook et al. | |
| 5,004,863 A | 4/1991 | Umbeck | |
| 5,013,659 A | 5/1991 | Bedbrook et al. | |
| 5,084,082 A | 1/1992 | Sebastian | |
| 5,141,870 A | 8/1992 | Bedbrook et al. | |
| 5,164,316 A | 11/1992 | McPherson et al. | |
| 5,196,525 A | 3/1993 | McPherson et al. | |
| 5,198,599 A | 3/1993 | Thill | |
| 5,276,268 A | 1/1994 | Strauch et al. | |
| 5,304,732 A | 4/1994 | Anderson et al. | |
| 5,322,938 A | 6/1994 | McPherson et al. | |
| 5,331,107 A | 7/1994 | Anderson et al. | |
| 5,352,605 A | 10/1994 | Fraley et al. | |
| 5,359,142 A | 10/1994 | McPherson et al. | |
| 5,378,824 A | 1/1995 | Bedbrook et al. | |
| 5,424,200 A | 6/1995 | McPherson et al. | |
| 5,463,175 A | 10/1995 | Barry et al. | |
| 5,561,236 A | 10/1996 | Leemans et al. | |

(Continued)

FOREIGN PATENT DOCUMENTS

| | | |
|---|---|---|
| EP | 0255378 A2 | 2/1988 |
| EP | 0507698 A1 | 3/1991 |

(Continued)

OTHER PUBLICATIONS

Romo et al (Plant Physiology and Biochemistry 43 (2005) 169-176) (Year: 2005).*

(Continued)

*Primary Examiner* — Lee A Visone

(57) ABSTRACT

The present invention relates to a hetero-transglycosylase protein having cellulose:xyloglucan endotransglucosylase (CXE) activity in addition to mixed-linkage beta-glucan:xyloglucan endotransglucosylase (MXE) activity. The protein may comprise the amino acid sequence of any one of SEQ ID NOs: 2, 6 and 8 or a functional fragment thereof; or an amino acid sequence having at least 60% sequence identity to any one of SEQ ID NO: 2, 6 and 8, or to SEQ ID NO: 2 from amino acid 22 to 280, to SEQ ID NO: 6 from amino acid 26 to 283, or to SEQ ID NO: 8 from amino acid 29 to 287. The invention furthermore relates to an isolated nucleic acid encoding the protein described herein, a chimeric gene comprising, inter alia, the nucleic acid described herein, a vector comprising said chimeric gene, a host cell comprising said vector or said chimeric gene and an according transgenic plant. Further disclosed herein in are a method of producing a transgenic plant and a method of improving properties of cellulosic material.

Figure 1:
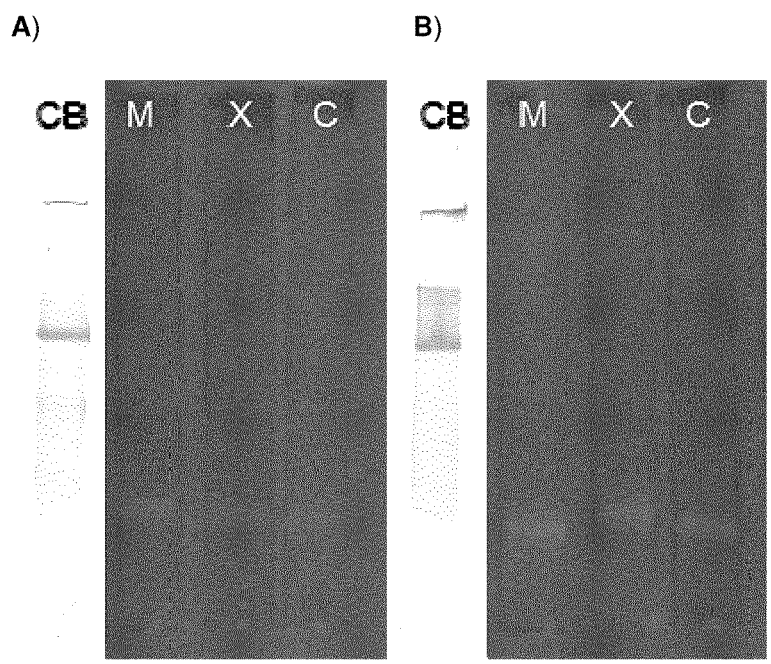

15 Claims, 11 Drawing Sheets
Specification includes a Sequence Listing.

(56) References Cited

U.S. PATENT DOCUMENTS

| | | | |
|---|---|---|---|
| 5,593,874 A | 1/1997 | Brown et al. | |
| 5,605,011 A | 2/1997 | Bedbrook et al. | |
| 5,637,489 A | 6/1997 | Strauch et al. | |
| 5,641,876 A | 6/1997 | McElroy et al. | |
| 5,646,024 A | 7/1997 | Leemans et al. | |
| 5,648,477 A | 7/1997 | Leemans et al. | |
| 5,659,122 A | 8/1997 | Austin | |
| 5,670,349 A | 9/1997 | Cramer et al. | |
| 5,731,180 A | 3/1998 | Dietrich | |
| 5,739,082 A | 4/1998 | Donn | |
| 5,792,930 A | 4/1998 | Chaubet et al. | |
| 5,767,361 A | 6/1998 | Dietrich | |
| 5,773,702 A | 6/1998 | Penner et al. | |
| 5,776,760 A | 7/1998 | Barry et al. | |
| 5,792,933 A | 8/1998 | Ma | |
| 5,879,903 A | 3/1999 | Strauch et al. | |
| 5,908,810 A | 6/1999 | Donn | |
| 5,928,937 A | 7/1999 | Kakefuda et al. | |
| 6,096,950 A | 8/2000 | John | |
| 6,166,294 A | 12/2000 | Kasukabe et al. | |
| 6,259,003 B1 | 7/2001 | Fujisawa et al. | |
| 6,271,443 B1 | 8/2001 | Stalker et al. | |
| 6,423,885 B1 | 7/2002 | Waterhouse et al. | |
| 6,483,013 B1 | 11/2002 | Reynaerts et al. | |
| 6,768,044 B1 | 7/2004 | Boudec et al. | |
| 7,053,205 B1 | 5/2006 | Verdaguer et al. | |
| 7,112,665 B1 | 9/2006 | Leemans et al. | |
| 7,172,881 B2 | 2/2007 | Huang et al. | |
| 7,635,798 B2 * | 12/2009 | Weglarz | C12N 15/8243 435/320.1 |
| 2003/0106097 A1 | 6/2003 | Haigler et al. | |
| 2003/0180945 A1 | 9/2003 | Wang et al. | |
| 2005/0144667 A1 | 6/2005 | Stanley et al. | |

FOREIGN PATENT DOCUMENTS

| | | |
|---|---|---|
| EP | 0633317 A1 | 6/1993 |
| EP | 0837944 A2 | 4/1998 |
| EP | 04077624.7 | 9/2004 |
| EP | 04077984.5 | 10/2004 |
| EP | 06009836.5 | 5/2006 |
| EP | 08075514.3 | 5/2008 |
| EP | 08010791.5 | 6/2008 |
| EP | 1999141 A2 | 12/2008 |
| EP | 1999263 A1 | 12/2008 |
| WO | 8707644 A1 | 12/1987 |
| WO | 9012107 A1 | 10/1990 |
| WO | 9215675 A1 | 9/1992 |
| WO | 9217580 A1 | 10/1992 |
| WO | 9421795 A1 | 9/1994 |
| WO | 9506742 A1 | 3/1995 |
| WO | 9606932 A1 | 3/1996 |
| WO | 9633270 A1 | 10/1996 |
| WO | 9638567 A2 | 12/1996 |
| WO | 9640924 A2 | 12/1996 |
| WO | 9711193 A1 | 3/1997 |
| WO | 9741218 A1 | 11/1997 |
| WO | 9800549 A1 | 1/1998 |
| WO | 9830698 A1 | 7/1998 |
| WO | 9845445 A1 | 10/1998 |
| WO | 9845461 A1 | 10/1998 |
| WO | 9854844 A1 | 12/1998 |
| WO | 9924585 A1 | 5/1999 |
| WO | 9924586 A1 | 5/1999 |
| WO | 9934008 A1 | 7/1999 |
| WO | 9953050 A1 | 10/1999 |
| WO | 9957965 A1 | 11/1999 |
| WO | 0004173 A1 | 1/2000 |
| WO | 0066746 A1 | 11/2000 |
| WO | 0066747 A1 | 11/2000 |
| WO | 0071733 A1 | 11/2000 |
| WO | 0112824 A1 | 2/2001 |
| WO | 0117333 A1 | 3/2001 |
| WO | 0124615 A1 | 4/2001 |
| WO | 0165922 A2 | 9/2001 |
| WO | 0166704 A2 | 9/2001 |
| WO | 0200904 A2 | 1/2002 |
| WO | 0210377 A1 | 2/2002 |
| WO | 0210413 A1 | 2/2002 |
| WO | 0224928 A1 | 3/2002 |
| WO | 0226995 A1 | 4/2002 |
| WO | 0236782 A2 | 5/2002 |
| WO | 0236787 A2 | 5/2002 |
| WO | 0245485 A1 | 6/2002 |
| WO | 0246387 A2 | 6/2002 |
| WO | 03013226 A2 | 2/2003 |
| WO | 03052108 A2 | 6/2003 |
| WO | 03076619 A1 | 9/2003 |
| WO | 03092360 A2 | 11/2003 |
| WO | 04040012 A2 | 5/2004 |
| WO | 04053219 A2 | 6/2004 |
| WO | 04073390 A1 | 9/2004 |
| WO | 2004090140 A2 | 10/2004 |
| WO | 04106529 A2 | 12/2004 |
| WO | 0512515 A2 | 2/2005 |
| WO | 2005017157 A1 | 2/2005 |
| WO | 2005020673 A1 | 3/2005 |
| WO | 2005047505 A2 | 5/2005 |
| WO | 2005052170 A2 | 6/2005 |
| WO | 2005093093 A2 | 10/2005 |
| WO | 2005098004 A2 | 10/2005 |
| WO | 2006007373 A2 | 1/2006 |
| WO | 2006015376 A2 | 2/2006 |
| WO | 2006024351 A1 | 3/2006 |
| WO | 2006045633 A1 | 5/2006 |
| WO | 2006074400 A2 | 7/2006 |
| WO | 2006129204 A2 | 12/2006 |
| WO | 2006133827 A2 | 12/2006 |
| WO | 2006136351 A2 | 12/2006 |
| WO | 0724782 A2 | 3/2007 |
| WO | 2007024782 A2 | 3/2007 |
| WO | 2007027777 A2 | 3/2007 |
| WO | 2007035650 A2 | 3/2007 |
| WO | 2007074405 A2 | 7/2007 |
| WO | 2007080126 A2 | 7/2007 |
| WO | 2007080127 A2 | 7/2007 |
| WO | 2007103567 A2 | 9/2007 |
| WO | 2007107302 A2 | 9/2007 |
| WO | 2007107326 A1 | 9/2007 |
| WO | 2008011681 A1 | 1/2008 |
| WO | 2008150473 A2 | 12/2008 |
| WO | 2009144079 A1 | 12/2009 |
| WO | 2011047646 A1 | 4/2011 |
| WO | 2011093970 A2 | 8/2011 |

OTHER PUBLICATIONS

Mans et al (Journal of Experimental Botany, vol. 62, No. 1, pp. 261-271, 2011) (Year: 2010).*

Abdel-Massih, Roula M., et al., In vitro biosynthesis of 1,4-b-galactan attached to a pectin-xyloglucan complex in pea, Planta, 2003, pp. 502-511, vol. 216.

An, Yong-Qiang, et al., Conserved Expression of the Arabidopsis ACTT and ACT3 Actin Subclass in Organ Primordia and Mature Pollen, The Plant Cell, Jan. 1996, pp. 15-30, vol. 8.

Baumann, Martin J., et al., Structural Evidence for the Evolution of Xyloglucanase Activity from Xyloglucan Endo-Transglycosylases: Biological Implications for Cell Wall Metabolism, The Plant Cell, Jun. 2007, pp. 1947-1963, vol. 19.

Benfey, Philip N., et al., The CaMV 35S enhancer contains at least two domains which can confer different developmental and tissue-specific expression patterns, The EMBO Journal, 1989, pp. 2195-2202, vol. 8, No. 8.

Carrington, James C., et al., Cap-Independent Enhancement of Translation by a Plant Potyvirus 5' Nontranslated Region, Journal of Virology, Apr. 1990, pp. 1590-1597, vol. 64, No. 4.

Cocuron, Jean-Christophe, et al., A gene from the cellulose synthase-like C family encodes a-1,4 glucan synthase, PNAS, May 15,2007, pp. 8550-8555, vol. 104, No. 20.

Comai, et al., An Alterred aroA Gene Product Confers Resistance to the Herbicide Glyphosate, Science, 1983, pp. 370-371, vol. 221.

(56) References Cited

OTHER PUBLICATIONS

Cornelissen, Ben J.C., et aL., Molecular characterization of messenger RNAs for 'pathogenesisrelated' proteins la, lb and lc, induced by TMV infection of tobacco, The EMBO Journal, 1986, pp. 37-40, vol. 5, No. 1Nucl.

Cornelissen, Marc, et al., Nuclear Transcriptional Activity of the Tobacco Plastid psbA Promoter, Nucleic Acids Research, 1989, vol. 17, No. 1.

Cregg, James M., Recent Advances in the Expression of Foreign Genes in Pichia Pastoris, 1993, Biotechnology (N.Y.), pp. 905-910, vol. 11.

Crickmore, N., et al., Revision of the Nomenclature for the Bacillus thuringiensis Pesticidal Crystal Proteins, Microbiology and Molecular Biology Reviews, Sep. 1998, pp. 807-813, vol. 62, No. 3.

Cumming, Carol M., et al., Biosynthesis and cell-wall deposition of a pectin-xyloglucan complex in pea, Planta, 2005, pp. 546-555, vol. 222.

Datla, Raju, et al., Plant Promoters for Transgene Expression, Biotechnology Annual Review, 1997, pp. 269-296, vol. 3.

Faik, Ahmed, et al., An *Arabidopsis* gene encoding a-xylosyltransferase involved in xyloglucan biosynthesis, PNAS, May 28, 2002, pp. 7797-7802, vol. 99, No. 11.

Frankova, Lenka, et al., Biochemistry and physiological roles of enzymes that 'cut and paste' plant cell-wall polysaccharides, Journal of Experimental Botany, 2013, pp. 3519-3550, vol. 64, No. 12.

Fry, Stephen, et al., Xyloglucan endotransglycosylase, a new wall-loosening enzyme activity from plants, Biochemical Journal, 1992, pp. 821-828, vol. 282.

Fry, Stephen, et al., An unambiguous nomenclature for xyloglucan-derived oligosaccharides, Physiologia Plantarum, 1993, pp. 1-3, vol. 89.

Fry, Stephen, et al., Mixed-linkage b-glucan : xyloglucan endotransglucosylase, a novel wall-remodelling enzyme from *Equisetum* (horsetails) and charophytic algae, The Plant Journal, 2008, pp. 240-252, vol. 55.

Gasser, Charles S., et al., Structure, Expression, and Evolution of the 5-Enolpyruvylshikimate-3-phosphate Synthase Genes of Petunia and Tomato, The Journal of Biological Chemistry, 1988, pp. 4280-4289, vol. 263, No. 9.

Giritch, Anatoli, et al., Rapid high-yield expression of full-size IgG antibodies in plants coinfected with noncompeting viral vectors, PNAS, Oct. 3, 2006, pp. 14701-14706, vol. 103, No. 40.

Gurjanov, Oleg P., et al., Polysaccharides, tightly bound to cellulose in cell wall of flax bast fibre: Isolation and identification, Carbohydrate Polymers, 2008, pp. 719-729, vol. 72.

Harpster, Mark H., et al., Relative Strengths of the 35S califlower mosaic virus, 1', 2', and nopaline synthase promoters in transformed tobacco surgarbeet and oilseed rape callus tissue, Mol. Biol. Genet, 1988, pp. 182-190, vol. 212.

Holtorf, Sonke, et al., Comparison of different constitutive and inducible promoters for the overexpression of transgenes in *Arabidopsis thaliana*, Plant Molecular Biology, 1995, pp. 637-646, vol. 29.

Hou, Lei, et al., SCFP, a novel fiber-specific promoter in cotton, Chinese Science Bulletin, Chinese Science Bulletin, 2008, pp. 2639-2645, vol. 53.

Hrmova, Maria, et al., A Barley Xyloglucan Xyloglucosyl Transferase Covalently Links Xyloglucan, Cellulosic Substrates, and (1,3;1,4)-D-Glucans, The Journal of Biological Chemistry, Apr. 27, 2007, pp. 12951-12962, vol. 282, No. 17.

Hrmova, Maria, et al., Substrate specificity and catalytic mechanism of a xyloglucan xyloglucosyl transferase HvXET6 from barley (*Hordeum vulgare* L.), FEBS Journal, 2009, pp. 437-456, vol. 276.

Keller, Beat, et al., Glycine-rich cell wall proteins in bean: gene structure and association of the protein with the vascular system, The EMBO Journal, 1988, pp. 3625-3633, vol. 7, No. 12.

Keller, Beat, et al., Specific expression of a novel cell wall hydroxyproline-rich glycoprotein gene in lateral root initiation, The EMBO Journal, 1989, Genes Dev. pp. 1639-1646, vol. 3.

Lindbo, John A., TRBO: A High-Efficiency Tobacco Mosaic Virus RNA-Based Overexpression Vector1[C][OA], Plant Physiology, Dec. 2007, pp. 1232-1240, vol. 145.

Maris, An, et al., Differences in enzymic properties of five recombinant xyloglucan endotransglucosylase/hydrolase (XTH) proteins of *Arabidopsis thaliana*, Journal of Experimental Botany, 2011, pp. 261-271, vol. 62, No. 1.

Moellenbeck, Daniel J., et al., Insecticidal proteins from Bacillus thuringiensis protect corn from corn rootworms, Nature Biotechnology, Jul. 2001, vol. 9.

Mohand, Fairouz, et al., Screening for hetero-transglycosylating activities in extracts from nasturtium (*Tropaeolum majus*), Carbohydrate Research, 2006, pp. 577-581, vol. 341.

Moreira, Andres, Genetic algorithms for the imitation of genomic styles in protein backtranslation, Theoretical Computer Science, 2004, pp. 297-312, vol. 322.

Moreira, L. R. S. et al., An overview of mannan structure and mannan-degrading enzyme systems, Applied Microbiology Biotechnology, 2008, pp. 165-178, vol. 79.

Needleman, Saul B., et al., A General Method Applicable to the search for Similarities in the Amino Acid Sequence of Two Proteins, J. Mol. Biol., 1970, pp. 443-453, vol. 48.

Odell, T., et al., Identification of DNA sequences required for activity of the cauliflower mosaic virus 35S promoter, Nature, 1985, pp. 810-812.

Panstruga, Ralph, et al., Testing the efficiency of dsRNAi constructs in vivo: A transient expression assay based on two fluorescent proteins, Molecular Biology Reports, 2003, pp. 135-140, vol. 30.

Pearson, William R., et al., Improved tools for biological sequence comparison, Proc. Natl. Acad. Sci., Apr. 1988, pp. 2444-2448, vol. 85.

Peleman, Johan, et al., Structure and expression analyses of the S-adenosylmethionine synthetase gene family in *Arabidopsis thaliana*, Gene, 1989, pp. 359-369, vol. 84.

Pu, Li, et al., The R2R3 MYB Transcription Factor GhMYB109 Is Required for Cotton Fiber Development, Genetics, Oct. 2008, pp. 811-820, vol. 180.

Rose, Jocelyn K.C., et al., Cooperative disassembly of the cellulose Dxyloglucan network of plant cell walls: parallels between cell expansion and fruit ripening, Genetics, May 1999, pp. 1360-1385, vol. 4, No. 5.

Samac, Deborah A., et al., A comparison of constitutive promoters for expression of transgenes in alfalfa (*Medicago sativa*), Transgenic Research, 2004, pp. 349-361, vol. 13.

Sanger, Margaret, et al., Characteristics of a strong promoter from figwort mosaic virus: comparison with the analogous 35S promoter from cauliflower mosaic virus and the regulated mannopine synthase promoter, Plant Molecular Biology, 1990, pp. 433-443, vol. 14.

Schnepf, J. Ernest, et al., Characterization of Cry34/Cry35 Binary Insecticidal Proteins from Diverse Bacillus thuringiensis Strain Collections, Applied and Environmental Microbiology, Apr. 2005, pp. 1765-1774, vol. 71, No. 4.

Schramm, Guido, et al., A simple and reliable 5'-RACE approach, Nucleic Acids Research, 2000, e96, vol. 28, No. 22.

Shah, Dilip M., et al., Engineering Herbicide Tolerance in Transgenic Plants, Science, 1986, pp. 478-481, vol. 233.

Smith, et al., Nature, Sep. 2000, pp. 319-320, vol. 407.

Somerville, Chris, et al., Toward a Systems Approach to Understanding Plant Cell Walls, Science, 2004, vol. 306.

Sorensen, Iben, et al., Mixed-linkage (1 fi 3),(1 fi 4)-b-D-glucan is not unique to the Poales and is an abundant component of Equisetum arvense cell walls, The Plant Journal, 2008, pp. 510-521, vol. 54.

Sutliff, Thomas D., et al., Characterization of an-amylase multigene cluster in rice, Plant Molecular Biology, 1991, pp. 579-591, vol. 16.

Thompson, James E., et al., Evidence for covalent linkage between xyloglucan and acidic pectins in suspension-cultured rose cells, Planta, 2000, pp. 275-286, vol. 211.

Tranel, Patrick J., et al., Resistance of weeds to ALS-inhibiting herbicides: what have we learned?, Weed Science, 2002, pp. 700-712, vol. 50.

Wagner, Birgit, et al., Plant virus expression systems for transient production of recombinant allergens in Nicotiana benthamiana, Methods, 2004, pp. 227-234, vol. 32.

(56) References Cited

OTHER PUBLICATIONS

Waterhouse, Peter M., et al, Exploring Plant Genomes by RNA-Induced Gene Silencing, Nature Reviews, Genetics, Jan. 2003, pp. 29-38, vol. 4.
Zanoni, Ivan, et al., CD14 regulates the dendritic cell life cycle after LPS exposure through NFAT activation, Nature, 2009, pp. 264-268, vol. 460.
Accession DY921601.
Accession GV605969.

* cited by examiner

A)

```
SEQ ID NO 1      1 --------------------ATGCTGGGTCTGGTG----
SEQ ID NO 5      1 ATGAAGAAG------------AAGATTGGAATGGTGCTGC
SEQ ID NO 7      1 ATGAAGAAGAAGACCGCGTCGATGCTGGGTTTGGCG----

SEQ ID NO 1     16 --TTTGGAATGTTGGTGATCATGCTGGCGTCTCCAAAATT
SEQ ID NO 5     29 TTTTGGGGCTTTTCATGATCATCATAGCGTCTCCCAA---
SEQ ID NO 7     37 --TTTGGGATGTTGTTGATCATGCTGGCGTCTCCAAAATT

SEQ ID NO 1     54 AGCAATGGCAGGTTTCTATGGGGACTTTCAGGTAGAACCG
SEQ ID NO 5     66 AGCAGAGGCAAATTTCTATCAAGATTTCGTCGTAGTTACA
SEQ ID NO 7     75 AGCAATAGCAGGTTTCTATGAGGACTTTGACGTAGATCCA

SEQ ID NO 1     94 GTTCCCGACCACGTGATAATCCAAAGCGATAGCCTCCTCC
SEQ ID NO 5    106 GCTCCTGACCATGTCCAAATCCTTAATGATAACCTCCTCC
SEQ ID NO 7    115 CCTCCCGACCACGTGATAATCCAAAGTGATAGCCTCCTCG

SEQ ID NO 1    134 AACTCACCATGGATAAGAACTCTGGTGGCTCAGTTGTCTC
SEQ ID NO 5    146 AGCTTACCATGGATAAGAATACTGGTAGCTCAATTAGCTC
SEQ ID NO 7    155 AACTCACCATGGATAAGAACTCTGGTAGCACAGTTGTCTC

SEQ ID NO 1    174 CAAAAGTAATTATCTGTTTGGCTACTTCAACATGAAGATG
SEQ ID NO 5    186 CACCAGTAAATACCTGTTTGGCTACTTCAACATGAGGATG
SEQ ID NO 7    195 CACCCGTAAATATCTGTTTGGCTACTTCAACATGAAGATG

SEQ ID NO 1    214 AAGCTCATATCAGGAAACTCTGCAGGGACAGTAACCACAT
SEQ ID NO 5    226 AAGCTCATAGCAGGCAACTCTGCAGGGACAGTGACCACCT
SEQ ID NO 7    235 AAGCTCATATCAGGCAACTCTGCAGGGACAGTAACCACAT

SEQ ID NO 1    254 TCTATATCTTCTCTGATGAAGCAAACCACGATGAGATAGA
SEQ ID NO 5    266 TCTATCTCTTCTCCAGTGAACCCAACCATGATGAGCTAGA
SEQ ID NO 7    275 TCTATATCTTCTCTGAGGAAGCAAACCACGATGAGATAGA

SEQ ID NO 1    294 CTTTGAGTTCCTTGGCAACTATTCAGGGGATCCTTATCTT
SEQ ID NO 5    306 CTTTGAGTTCCTTGGCAATCTTTCAGGGGAACCTTATGTT
SEQ ID NO 7    315 CTTTGAGTTCCTTGGCAACTATTCAGGGGATCCTTATCTT

SEQ ID NO 1    334 TTGCATACTAATATTTTTGCAAGTGGTGTTGGAAATAGAG
SEQ ID NO 5    346 TTGCATACAAATGTTTTTGCAAGTGGTGTTGGAAATAGAG
SEQ ID NO 7    355 TTGCATACTAATATTTTTGCAAGTGGTGTTGGAAATAGAG

SEQ ID NO 1    374 AACAACAATTTTTTCTGTGGTTTGACCCTACAGCTGACTT
SEQ ID NO 5    386 AACAACAATTTTTTCTGTGGTTTGACCCTACAACTGACTT
SEQ ID NO 7    395 AACAACAATTTTTTCTGTGGTTTGACCCTACAGCTGACTT
```

Figure 8

```
SEQ ID NO 1    414  CCATGATTATACAATAATTTGGAACCCTCAACAAATATTG
SEQ ID NO 5    426  CCACGACTATACAATAATTTGGAACCCTCAACAAGTATTG
SEQ ID NO 7    435  CCATGATTATACAATAATTTGGAACCCTCAACAAATATTG

SEQ ID NO 1    454  TTTCTTGTTGATGGAAGGGCTGTTAGATCTTTTCCGAATA
SEQ ID NO 5    466  TTTGTTGTTGATGGAAGGACTGTTAGATCTTTCCCAAATA
SEQ ID NO 7    475  TTTCTTGTTGATGGAAGGGCTGTTAGATCTTTTCCGAATA

SEQ ID NO 1    494  ATGAGGCTATAGGTGTCCCTTACTTAAAAAGTCAATGGAT
SEQ ID NO 5    506  ATGAGGCTATAGGTGTCCCTTACTTAAAAAGTCAATGGAT
SEQ ID NO 7    515  ATGAGGCTATAGGTGTCCCTTACTTAAAAAGTCAATGGAT

SEQ ID NO 1    534  GAATGTACATTTAAGTCTTTGGAATGGCGAGACTTGGGCC
SEQ ID NO 5    546  GAATGTATATGCAAGCCTTTGGAATGGTGAGTCTTGGGCC
SEQ ID NO 7    555  GAATGTACATTTAAGTCTTTGGAATGGCGAGACTTGGGCC

SEQ ID NO 1    574  ACACTAGGAGGGTTGAGAAGGATAGATTGGAATTCAGCCC
SEQ ID NO 5    586  ACACTAGGAGGGCTGATAAAGATAGATTGGAGTGTATCCC
SEQ ID NO 7    595  ACACTAGGAGGGTTGAGAAGGATAGATTGGAATTCAGCCC

SEQ ID NO 1    614  CTTTTGTAGCTTCCTATTCTACTTTTGTAGGAGACTCATG
SEQ ID NO 5    626  CTTTTGTGGCTTCCTATGCTGATTTGCAGCAGACTCATG
SEQ ID NO 7    635  CTTTTGTAGCTTCCTATTCTACTTTTGTAGGAGACTCATG

SEQ ID NO 1    654  CTTCGATAGCGCAGATTCCCCGTGCATGGCCTCAAAATGG
SEQ ID NO 5    666  CTTTGATAGTGCAGATTCCTCATGCATGGCCACAAAGTGG
SEQ ID NO 7    675  CTTCGATAGCGCAGATTCCCCGTGCATGGCCTCAAAATGG

SEQ ID NO 1    694  TGGAACCAAGCTGCATATCAATCTTTAAGCACAAGTGATG
SEQ ID NO 5    706  TGGAACCAACCTGCATATCAATTTTTAAGCACAAATGATG
SEQ ID NO 7    715  TGGAACCAAGCTGCATATCAATCTTTAAGCACAAGTGATG

SEQ ID NO 1    734  CCAGCAGTATTCAATGGGTTAGGGAAAATTATCTCAAATA
SEQ ID NO 5    746  CAAGCAGTATTCAATGGGTTAGGGCAAATTATCTCAAATA
SEQ ID NO 7    755  CCAGCAGTATTCAATGGGTTAGGGCAAATTATCTCAAATA

SEQ ID NO 1    774  TGACTATTGTTATGATACAAAACTCTATCCGAACGGCTTT
SEQ ID NO 5    786  CGACTATTGTTATGATACGGAACTCTATCC-AACTCC--T
SEQ ID NO 7    795  TGACTATTGTTATGATACAAAACTCTATCCGAACGGCTTT

SEQ ID NO 1    814  CCCAGAGAATGCTCAAACCGTGGTTTCTAG
SEQ ID NO 5    823  CCCATCGAATGTCAGAACCGTGGCTTCTAG
SEQ ID NO 7    835  CCCAGCGAATGCTCAAACCGTGGTTTCTAG
```

Figure 8, continued

B)
```
SEQ ID NO 2      1 -------MLGLVF--GMLVIMLASPKLAMAGFYGDFQVEP
SEQ ID NO 6      1 MKK----KIGMVLLLGLFMIIIASPK-AEANFYQDFVVVT
SEQ ID NO 8      1 MKKKTASMLGLAF--GMLLIMLASPKLAIAGFYEDFDVDP

SEQ ID NO 2     32 VPDHVIIQSDSLLQLTMDKNSGGSVVSKSNYLFGYFNMKM
SEQ ID NO 6     36 APDHVQILNDNLLQLTMDKNTGSSISSTSKYLFGYFNMRM
SEQ ID NO 8     39 PPDHVIIQSDSLLELTMDKNSGSTVVSTRKYLFGYFNMKM

SEQ ID NO 2     72 KLISGNSAGTVTTFYIFSDEANHDEIDFEFLGNYSGDPYL
SEQ ID NO 6     76 KLIAGNSAGTVTTFYLFSSEPNHDELDFEFLGNLSGEPYV
SEQ ID NO 8     79 KLISGNSAGTVTTFYIFSEEANHDEIDFEFLGNYSGDPYL

SEQ ID NO 2    112 LHTNIFASGVGNREQQFFLWFDPTADFHDYTIIWNPQQIL
SEQ ID NO 6    116 LHTNVFASGVGNREQQFFLWFDPTTDFHDYTIIWNPQQVL
SEQ ID NO 8    119 LHTNIFASGVGNREQQFFLWFDPTADFHDYTIIWNPQQIL

SEQ ID NO 2    152 FLVDGRAVRSFPNNEAIGVPYLKSQWMNVHLSLWNGETWA
SEQ ID NO 6    156 FVVDGRTVRSFPNNEAIGVPYLKSQWMNVYASLWNGESWA
SEQ ID NO 8    159 FLVDGRAVRSFPNNEAIGVPYLKSQWMNVHLSLWNGETWA

SEQ ID NO 2    192 TLGGLRRIDWNSAPFVASYSTFVGDSCFDSADSPCMASKW
SEQ ID NO 6    196 TLGGLIKIDWSVSPFVASYADFAADSCFDSADSSCMATKW
SEQ ID NO 8    199 TLGGLRRIDWNSAPFVASYSTFVGDSCFDSADSPCMASKW

SEQ ID NO 2    232 WNQAAYQSLSTSDASSIQWVRENYLKYDYCYDTKLYPNGF
SEQ ID NO 6    236 WNQPAYQFLSTNDASSIQWVRANYLKYDYCYDTELYPTP-
SEQ ID NO 8    239 WNQAAYQSLSTSDASSIQWVRANYLKYDYCYDTKLYPNGF

SEQ ID NO 2    272 PRECSNRGF
SEQ ID NO 6    275 PIECQNRGF
SEQ ID NO 8    279 PSECSNRGF
```

Figure 8, continued

HETERO-TRANSGLYCOSYLASE AND USES THEREOF

CROSS REFERENCE TO RELATED APPLICATIONS

This application is a § 371 U.S. national stage of International Patent Application No. PCT/EP14/070381 filed on Sep. 24, 2014, which claims the benefit of European Patent Application Serial No. 13185727.8, filed Sep. 24, 2013, and European Patent Application Serial No. 13192054.8, filed Nov. 8, 2013, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "BCS13-2019-WO1.txt," created on Oct. 30, 2013, and having a size of 30 kilobytes and is filed concurrently with the specification. The sequence listing contained in this ASCII formatted document is part of the specification and is herein incorporated by reference in its entirety.

The present invention relates to hetero-transglycosylase (HTG) proteins having cellulose:xyloglucan endotransglucosylase (CXE) activity in addition to mixed-linkage beta-glucan:xyloglucan endotransglucosylase (MXE) activity. The protein may comprise the amino acid sequence of any one of SEQ ID NO: 2, 6 and 8 or a functional fragment thereof; or the protein may comprise an amino acid sequence having at least 60% sequence identity to any one of SEQ ID NOs: 2, 6 and 8 or to SEQ ID NO: 2 from amino acid 22 to 280, to SEQ ID NO: 6 from amino acid 26 to 283, or to SEQ ID NO: 8 from amino acid 29 to 287. The invention furthermore relates to an isolated nucleic acid encoding the protein described herein, a chimeric gene comprising, inter alia, the nucleic acid described herein, a vector comprising said chimeric gene, a host cell comprising said vector or said chimeric gene and transgenic plant comprising said chimeric gene.

Further disclosed herein are a method of producing a transgenic plant and a method of altering at least one fiber property in a fiber-producing plant or for strengthening a plant as characterized in the claims.

In this specification, a number of documents including patent applications and manufacturers' manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The structural integrity of land plants is mediated in large part by the cell walls surrounding plant cells which are held responsible for strength and flexibility of plants. Besides this function, plant cell walls are also important for intercellular cohesion and cell-to-cell communication. Porosity of the cell walls enable water and nutrient exchange. The primary cell walls of vascular plants consist of cellulose microfibrils embedded in a chemically complex matrix consisting of polysaccharides such as mainly xyloglucans and pectic polysaccharides in dicotyledonous plants and many monocotyledonous plants or glucuronoarabinoxylans and (1,3;1,4)-beta-D-glucans mainly in grasses and cereals. Although the types and abundance of polysaccharides in plant cell walls have been elucidated so far, only little information is available on the molecular interactions between polysaccharides in the cell wall. Extensive intermolecular hydrogen bonding rather than covalent interactions has very long been held responsible for holding different polysaccharides in place (Bacic et al. 1988; Somerville et al. 2004).

BACKGROUND OF THE INVENTION

Xyloglucans have been found to be an important factor in cell wall morphogenesis (reviewed in Baumann et al., 2007) and are able to make hydrogen bonds to cellulose, for reference see The Plant Journal, 1993, p. 1-30.

Polysaccharide transglycosylases, also called polysaccharide transglycanases, catalyze the reorganization of polysaccharide molecules by cleaving glycosidic linkages in polysaccharide chains and transferring their cleaved portions to hydroxyl groups at non-reducing residues of other polysaccharide or oligosaccharide molecules (reviewed by Franková and Fry, 2013; herewith incorporated by reference). Examples of transglycosylases are transglucosylases (also called transglucanases), transxylanases and transmannanases. Of these, Xyloglucan endotransglucosylases (XETs; also called xyloglucan endotransglucanases, or XTHs or xyloglucan xyloglucosyl transferases) restructure xyloglucan in primary and secondary cell walls of land plants including *Equisetum* and liverworts (Fry et al., 1992; Fry et al. 2008). Unlike most other land plants tested, *Equisetum* additionally exhibits a distinct endotransglucosylase (or endotransglucanase) called mixed-linkage beta-glucan:xyloglucan endotransglucosylase (MXE) (or mixed-linkage beta-glucan:xyloblucan endotransglucanase). The latter enzyme uses mixed-linkage (1,3;1,4)-beta-glucan (MLG) as the donor substrate and attaches it covalently to xyloglucan or a fragment thereof (Fry et al., 2008). So far, enzymes catalyzing hetero transglycosylation, i. e. using qualitatively different donor and acceptor substrates, have been found but not characterized in detail (Ait Mohand and Farkaš, 2006), or have been found to only have a minor hetero-transglycosylation activity (Hrmova et al., see below).

It has been shown that xyloglucans are covalently linked to pectic polysaccharides (Thompson and Fry 2000). Evidence for covalent linkage between xyloglucan and acidic pectins in suspension-cultured rose cells is described in Abdel-Massih et al. (2003) and Cumming et al. (2005,). Furthermore, Hrmova et al. have shown that an XET from barley links MLG, hydroxyethylcellulose and sulfuric acid swollen cellulose (i. e. cellulose sulfate) to xyloglucan (Hrmova et al. 2007). In its capacity to link MLG to xyloglucan, this barley enzyme exhibits MXE activity which, however, amounts only to about 0.2% of its XET activity.

DISCLOSURE OF THE PRESENT INVENTION

So far no transglucosylase activity has been described that covalently attaches insoluble cellulose to xyloglucan. Such activity could have important applications in the functionalization of cellulosic materials such as textiles, paper or wood pulp.

Accordingly, in a first embodiment, the present invention relates to a protein having cellulose:xyloglucan endotransglucosylase (CXE) activity.

In one embodiment, the protein is derived from *Equisetum*, such as *Equisetum fluviatile, Equisetum hyemale*, or *Equisetum diffusum*.

In another embodiment, the protein comprises (a) the amino acid sequence of any one of SEQ ID NOs: 2, 6 and 8 or a functional fragment thereof; or (b) an amino acid sequence having at least 60% sequence identity to the sequence of any one of SEQ ID NOs: 2, 6 and 8; or (c) an amino acid sequence having at least 60% sequence identity to the sequence of SEQ ID NO: 2 from amino acid 22 to 280, to the sequence of SEQ ID NO: 6 from amino acid 26 to 283, or to the sequence of SEQ ID NO: 8 from amino acid 29 to 287.

Unless indicated otherwise, the embodiments and examples described below for certain aspects disclosed herein are also applicable to respective embodiments of other aspects disclosed herein.

The term "protein" as used herein describes a group of molecules consisting of more than 30 amino acids, whereas the term "peptide" describes molecules consisting of up to 30 amino acids. Proteins and peptides may further form dimers, trimers and higher oligomers, i.e. consisting of more than one (poly)peptide molecule. Protein or peptide molecules forming such dimers, trimers etc. may be identical or non-identical. The corresponding higher order structures are, consequently, termed homo- or heterodimers, homo- or heterotrimers etc. The terms "protein" and "peptide" also refer to naturally modified proteins or peptides wherein the modification is effected e.g. by glycosylation, acetylation, phosphorylation and the like. Such modifications are well known in the art.

Cellulose:xyloglucan endotransglucosylase (CXE) activity denotes the activity of the protein of the invention to catalyse the transfer of glucan (or cello-oligosaccharides) units from cellulose as the donor molecule to xyloglucan (or oligosaccharides thereof) as acceptor molecule. More particularly, the protein of the invention cleaves a β-(1→4)-glucose bond in a cellulose chain, and then re-forms a glycosidic bond to a non-reducing residue of a xyloglucan polymer or oligomer, the acceptor substrate.

As used herein, the term "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein or attached to another nucleic acid or protein stretch. A chimeric gene comprising a DNA region which is functionally or structurally defined may accordingly comprise additional DNA regions etc. However, in context with the present disclosure, the term "comprising" also includes "consisting of".

A "functional fragment" of the amino acid sequences of any one of SEQ ID NOs: 2, 6 and 8 denotes a protein or peptide comprising a stretch of the amino acid sequences listed above which still exerts the desired function, i. e. which has cellulose:xyloglucan endotransglucosylase activity. An assay for determining of whether a functional fragment has cellulose:xyloglucan endotransglucosylase activity is disclosed in the appended examples. An example of a functional fragment of the amino acid sequence of SEQ ID NO: 2 is the fragment comprising amino acids 22 to 280 of SEQ ID NO: 2; an example of a functional fragment of the amino acid sequence of SEQ ID NO: 6 is the fragment comprising amino acids 26 to 283 of SEQ ID NO: 6, and an example of a functional fragment of the amino acid sequence of SEQ ID NO: 8 is the fragment comprising amino acids 29 to 287 of SEQ ID NO: 8.

In one aspect, the present protein having cellulose:xyloglucan endotransglucosylase activity comprises an amino acid sequence having at least 50%, at least 60%, at least 70%, at least 80%, at least 90%, at least 95% or at least 98% sequence identity to SEQ ID NO: 2 or to SEQ ID NO: 2 from amino acid 22 to 280 or to SEQ ID NO: 6 or to SEQ ID NO: 6 from amino acid 26 to 283, or to SEQ ID NO: 8, or to SEQ ID NO: 8 from amino acid 29 to 287. Such amino acid sequences also include artificially derived amino acid sequences, such as those generated, for example, by mutagenesis of the nucleic acids encoding the amino acid of SEQ ID NO: 2 or of SEQ ID NO: 2 from amino acid 22 to 280 or of SEQ ID NO: 6 or of SEQ ID NO: 6 from amino acid 26 to 283, or of SEQ ID NO: 8, or of SEQ ID NO: 8 from amino acid 29 to 287. Generally, amino acid sequences disclosed herein may have at least 50%, such as 52%, 54%, 56%, 58%, at least 60%, such as 62%, 64%, 66%, 68%, at least 70%, such as 72%, 74%, 75%, 76%, 78%, at least 80%, e.g., 81% to 84%, at least 85%, e.g., 86%, 87%, 88%, 89%, 90%, 91%, 92%, 93%, 94%, 95%, 96%, 97%, to 98%, and 99% sequence identity to the amino acid sequence of SEQ ID NO: 2 or of SEQ ID NO: 2 from amino acid 22 to 280 or of SEQ ID NO: 6 or of SEQ ID NO: 6 from amino acid 26 to 283, or of SEQ ID NO: 8, or of SEQ ID NO: 8 from amino acid 29 to 287.

As used herein, the term "percent sequence identity" refers to the percentage of identical amino acids between two segments of a window of optimally aligned amino acid sequences. Optimal alignment of sequences for aligning a comparison window are well-known to those skilled in the art and may be conducted by tools such as the local homology algorithm of Smith and Waterman (Waterman, M. S., Chapman & Hall. London, 1995), the homology alignment algorithm of Needleman and Wunsch (1970), the search for similarity method of Pearson and Lipman (1988), and preferably by computerized implementations of these algorithms such as GAP, BESTFIT, FASTA, and TFASTA available as part of the GCG (Registered Trade Mark), Wisconsin Package (Registered Trade Mark from Accelrys Inc., San Diego, Calif.). An "identity fraction" for aligned segments of a test sequence and a reference sequence is the number of identical components that are shared by the two aligned sequences divided by the total number of components in the reference sequence segment, i.e., the entire reference sequence or a smaller defined part of the reference sequence. Percent sequence identity is represented as the identity fraction times 100. The comparison of one or more amino acid or DNA sequences may be to a full-length amino acid or DNA sequence or a portion thereof, or to a longer amino acid or DNA sequence. Sequence identity is calculated based on the shorter nucleotide or amino acid sequence.

Only proteins which have cellulose:xyloglucan endotransglucosylase activity are encompassed by the present invention. Proteins having cellulose:xyloglucan endotransglucosylase activity disclosed herein include the amino acid sequences disclosed herein and those with the indicated degree of sequence identity but also deletions of sequence, single or multiple sequence alterations or addition of functional elements as long as cellulose:xyloglucan endotransglucosylase activity is essentially retained. Techniques for obtaining such derivatives are well-known in the art (see, for example, J. F. Sambrook, D. W. Russell, and N. Irwin, 2000). For example, one of ordinary skill in the art may delimit the functional elements within the protein disclosed herein and delete any non-essential elements. The functional elements may be modified or combined to increase the utility or expression of the sequences of the invention for any particular application. Those of skill in the art are familiar with the standard resource materials that describe specific conditions and procedures for the construction, manipulation, and isolation of macromolecules (e.g. DNA molecules, plasmids, proteins etc.), as well as the generation of recombinant organisms and the screening and isolation of DNA molecules and proteins.

The present inventors, for the first time, show that heterotransglucosylases exist which are able to directly link cellulose to xyloglucan.

As described above, Baumann et al. describe the enzymatic activity of NXG1 from *Tropaeolum majus* which can use cello-oligosaccharides as acceptors. They observed, inter alia, cellobiose, cellotriose and cellotetraose products. This partly contradicts the findings of Ait Mohand et al. (2006) who could show such products when applying fluorescent dyes in the detection method but not when radiolabeled probes were used. The authors concluded that the detected activity could be an artificial one attributed to the presence of the fluorescent dye within the cellooligosaccharides used as acceptor. Hrmova et al. (2007) demonstrated that a purified XET from barley seedlings catalyzes in vitro formation of covalent linkages between certain soluble substrates (such as hydroxyethylcellulose and cellulose sulfate) and xyloglucan. The authors indicate that such activity has not been demonstrated to have any in muro significance. Such demonstration would require isolation of a short fragment of 10 or fewer glycosyl residues that can be clearly shown to originate from two distinct polysaccharide types such as cellulose and xyloglucan.

So far, no enzymatic activity linking cellulose to xyloglucan has been demonstrated, as opposed to soluble cellulosic material such as hydroxyethylcellulose or sulfuric acid swollen cellulose. As shown in the appended examples, the nucleic acids encoding an enzyme with such activity have been found in *Equisetum* by the present inventors. By a novel method enabling to directly measure the new activity with cellulose as donor they could surprisingly show that the novel enzyme is able to transfer the insoluble donor cellulose to the soluble xyloglucan whereas previous studies could only identify an enzymatic activity on soluble cellulose derivatives. By comparing the results obtained therewith with those obtained for other donor-acceptor combinations, the present inventors in addition showed that the novel activity is one of the predominant activities of the protein of the invention.

In one embodiment, said cellulose:xyloglucan endotransglucosylase activity is one of the predominant activities of the protein.

The term "predominant activity" denotes an activity of the protein disclosed herein as cellulose:xyloglucan endotransglucosylase which is at least 5% that of the highest activity on other donors/acceptors. In one example, the activity is at least 10%, at least 20%, at least 30%, at least 40%, at least 50%, at least the same (at least 100%), at least 200%, at least 500% or at least 1000% that of the highest activity on other donors/acceptors. The protein of the invention may have more than one predominant activity such as two or three which preferably differ by the factor of 10 or less. The protein of the invention may also have one or more activities related to soluble cellulose derivatives such as water-soluble cellulose acetate, hydroxyethylcellulose, carboxymethylcellulose, cellulose sulphate.

Methods of measuring and comparing an enzyme's activity on different soluble donor/acceptor combinations are known in the art and can also be found in the appended examples. A method to determine an enzyme's activity on (insoluble) cellulose as the donor molecule is disclosed in the appended examples. The nature of the soluble or insoluble donor molecules does not allow a determination of enzymatic activity under strictly the same conditions because e. g. cellulose as an insoluble donor molecule is much less accessible to the enzyme than soluble donor molecules. However, for the purpose of the present invention, a comparison between different activities can be conducted under conditions described in the appended examples for soluble and insoluble donor molecules.

In one example, the protein of the invention further has MXE activity.

Also disclosed is an isolated nucleic acid encoding the protein disclosed herein.

Nucleic acids can be DNA or RNA, single- or double-stranded. Nucleic acids can be synthesized chemically or produced by biological expression in vitro or even in vivo.

Nucleic acids can be chemically synthesized using appropriately protected ribonucleoside phosphoramidites and a conventional DNA/RNA synthesizer. Suppliers of RNA synthesis reagents are Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK).

In connection with the chimeric gene of the present disclosure, DNA includes cDNA and genomic DNA.

An "isolated nucleic acid" or "isolated nucleic acid sequence", as used in the present application, refers to a nucleic acid as defined above which is not naturally-occurring (such as an artificial or synthetic nucleic acid with a different nucleotide sequence than the naturally-occurring nucleic acid or a nucleic acid which is shorter than a naturally occurring one) or which is no longer in the natural environment wherein it was originally present, e.g., a nucleic acid coding sequence associated with a heterologous regulatory element (such as a bacterial coding sequence operably-linked to a plant-expressible promoter) in a chimeric gene or a nucleic acid transferred into another host cell, such as a transgenic plant cell.

The protein having cellulose:xyloglucan endotransglucosylase (CXE) activity according to the invention can be a HTG protein.

A "HTG protein", also called "HTG-enzyme", "hetero-trans-β-glucanase", or "hetero-trans-β-glucosylase", as used herein is a hetero-transglycosylase, or hetero-transglycanase, of which the major activity is a hetero-transglucosylase activity. Said major activity can be at least 50%, at least 60%, or at least 70% of the total activity. A HTG can have MXE and CXE activity.

The nucleic acid encoding the protein having cellulose:xyloglucan endotransglucosylase (CXE) activity, or said HTG protein, could be introduced into other plants to create modified cellulose microfibrils in the living plant, e. g. crop plant.

It is believed that expressing the present nucleic acid in a plant results in an activity of the resulting enzyme which covalently links some of the plant's cellulose molecules to its endogenous xyloglucan, thus strengthening the cell wall, e.g. in plant fiber products. Wall strengthening could also be useful in any crop plant, e.g. to minimize lodging of (crop) plants such as cereals or oilseeds or to enhance the strength of wood or crop plants.

Alternatively, a plant expressing the nucleic acid disclosed herein could be either fed, or genetically altered to synthesise endogenously, xyloglucan, wherein said xyloglucan, in case of feeding optionally has a further organic or inorganic molecule attached to it (as described further below). Potential applications include: cellulosic paper, cellulosic textiles e.g. cotton or linen, cellulosic packaging e.g. cardboard, cellulosic building materials e.g. timber and chipboard, cellulosic derivatives e.g. carboxymethylcellulose or cellulose acetate, thickening agents e.g. xanthan gum or derivatives thereof, cellulosic medical dressings e.g. cotton wool, gauzes, cellophane, dialysis tubing, cellulosic chromatography column packing materials; the attached organic or inorganic substances could be selected to enable affinity chromatography.

In another example, the plant expressing the nucleic acid disclosed herein could be harvested under conditions maintaining the activities of the HTG enzyme, e.g. in plant fibers, such that xyloglucan or a xyloglucan oligosaccharide, optionally having an organic or inorganic substance attached thereto could be incorporated into the cellulose post-harvest with no further addition of enzyme. Potential applications are listed above.

Alternatively, the HTG protein could be expressed heterologously, e.g. in a micro-organism, and, after isolation, applied post-harvest to unmodified plant fibers or (plant-derived) cellulose in the presence of xyloglucan or a xyloglucan oligosaccharide, optionally having an organic or inorganic molecule attached thereto, to which the cellulose would become attached covalently.

In summary, by adding the protein of the invention to insoluble cellulosic material, i. e. material comprising cellulose, the present inventors are able to increase the amount of xyloglucan mediated interlinkages between the cellulosic fibers. Hereby they have created an environmentally friendly enzymatic process for improving the strength and/or other properties of various cellulosic materials as an alternative to the chemical processes known so far. Alternatively, the protein of the invention allows covalently attachment of new functionalities to the cellulose through covalent linkage of modified xyloglucans.

In one example, the isolated nucleic acid comprises a nucleic acid having at least 60% sequence identity to SEQ ID NO: 1, or SEQ ID NO: 5, or SEQ ID NO: 7 or the complement thereof, or a nucleic acid having at least 60% sequence identity to SEQ ID NO: 1 from nucleotide 64 to 840 or the complement thereof, or to SEQ ID NO: 5 from nucleotide 76 to 849 or the complement thereof, or to SEQ ID NO: 7 from nucleotide 85 to 861 or the complement thereof, or a nucleic acid sequence hybridizing under high stringency conditions to the sequence of SEQ ID NO: 1, or SEQ ID NO: 5, or SEQ ID NO: 7 or the complement thereof. Said isolated nucleic acid may also comprise or consist of the nucleic acid sequence of SEQ ID NO: 1 or of SEQ ID NO: 1 from nucleotide 64 to 840 or of SEQ ID NO: 5 or of SEQ ID NO: 5 from nucleotide 76 to 849 or of SEQ ID NO: 7, or of SEQ ID NO: 7 from nucleotide 85 to 861 or the complement thereof. Further provided is a nucleic acid, which may be an isolated nucleic acid having at least 60% sequence identity to SEQ ID NO: 1 from nucleotide 64 to 840 or the complement thereof, provided that nucleotide 1 to 63 are not present, or to SEQ ID NO: 5 from nucleotide 76 to 849 or the complement thereof provided that nucleotide 1 to 75 are not present, or to SEQ ID NO: 7 from nucleotide 85 to 861 or the complement thereof, provided that nucleotide 1 to 84 are not present. Further provided is a nucleic acid, which may be an isolated nucleic acid, encoding a protein comprising an amino acid sequence having at least 60% sequence identity to the sequence of any one of SEQ ID NOs: 2, 6 and 8 of which codon usage is adapted for expression in bacteria, or for expression in yeast, or for expression in plants.

Codon usage can be optimized, for example, as described by Moreira, 2004.

Also disclosed herein is a chimeric gene comprising the following operably linked elements: (a) a promoter, e. g. a promoter expressible in plants, bacteria or yeast; (b) the nucleic acid capable of modulating expression of the protein as described herein; and, optinally, (c) a transcription termination and polyadenylation region.

A nucleic acid capable of modulating expression of the protein as described herein can be a nucleic acid capable of downregulating expression of the protein as described herein.

In another embodiment, said nucleic acid capable of modulating expression of the protein of the invention is selected from the group consisting of a nucleic acid sequence encoding the protein according to the invention; a nucleic acid sequence having at least 60% sequence identity to any one of SEQ ID NOs: 1, 5 and 7 or the complement thereof; a nucleic acid sequence having at least 60% sequence identity to the sequence of SEQ ID NO: 1 from nucleotide 64 to 840 or the complement thereof, to the sequence of SEQ ID NO: 5 from nucleotide 76 to 849 or the complement thereof, or to the sequence of SEQ ID NO: 7 from nucleotide 85 to 861 or the complement thereof; and a nucleic acid sequence hybridizing under high stringency conditions to the sequence of any one of SEQ ID NOs: 1, 5 and 7 or the complement thereof.

An nucleic acid capable of downregulating or, in other words, decreasing expression of the protein as described herein can be an nucleic acid encoding a protein which inhibits expression and/or activity of said protein. Further, said nucleic acid molecule that results in a decreased expression of the protein as described herein can also be a nucleic acid molecule which inhibits expression of a gene which is an activator of expression of said protein. Said nucleic acid molecule that inhibits the expression of the protein as described herein may also be an RNA molecule that directly inhibits expression of said protein, such as an RNA which mediates silencing of the gene encoding said protein.

Decreasing the expression and/or activity of the protein of the invention can be decreasing the amount of functional protein produced. Said decrease can be a decrease with at least 30%, 40%, 50%, 60%, 70%, 80%, 90%, 95% or 100% (i.e. no functional protein is produced by the cell) as compared to the amount of functional protein produced by a cell with wild type expression levels and activity. Said decrease in expression can be a constitutive decrease in the amount of functional protein produced. Said decrease can also be a temporal/inducible decrease in the amount of functional protein produced.

The expression of the gene encoding the protein according to the invention can conveniently be reduced or eliminated by transcriptional or post-transcriptional silencing of the expression of endogenous gene. To this end and within the chimeric gene described above, a silencing RNA molecule is introduced in the plant cells targeting the endogenous genes encoding the protein of the invention. As used herein, "silencing RNA" or "silencing RNA molecule" refers to any RNA molecule, which upon introduction into a cell, reduces the expression of a target gene. Such silencing RNA may e.g. be so-called "antisense RNA", whereby the RNA molecule comprises a sequence of at least 20 consecutive nucleotides having 95% sequence identity to the complement of the sequence of the target nucleic acid, preferably the coding sequence of the target gene. However, antisense RNA may also be directed to regulatory sequences of target genes, including the promoter sequences and transcription termination and polyadenylation signals. Silencing RNA further includes so-called "sense RNA" whereby the RNA molecule comprises a sequence of at least 20 consecutive nucleotides having 95% sequence identity to the sequence of the target nucleic acid. Other silencing RNA may be "unpolyadenylated RNA" comprising at least 20 consecutive nucleotides having 95% sequence identity to the complement of the sequence of the target nucleic acid, such as described in WO01/12824 or U.S. Pat. No. 6,423,885 (both documents herein incorporated by reference). Yet another type of silencing RNA is an RNA molecule as described in WO03/076619 (herein incorporated by reference) comprising at least 20 consecutive nucleotides having at least 95%, at least 96%, at least 97% at least 98%, at least 99% or 100% sequence identity to the sequence of the target nucleic acid or the complement thereof, and further comprising a largely-double stranded region as described in WO03/076619 (including largely double stranded regions comprising a nuclear localization signal from a viroid of the Potato spindle tuber viroid-type or comprising CUG trinucleotide repeats). Silencing RNA may also be double stranded RNA comprising a sense and antisense strand as herein defined, wherein the sense and antisense strand are capable of base-pairing with each other to form a double stranded RNA region (preferably the said at least 20 consecutive nucleotides of the sense and antisense RNA are complementary to each other). The sense and antisense region may also be present within one RNA molecule such that a hairpin RNA (hpRNA) can be formed when the sense and antisense region form a double stranded RNA region. hpRNA is well-known within the art (see e.g WO99/53050, herein incorporated by reference). The hpRNA may be classified as long hpRNA, having long, sense and antisense regions which can be largely complementary, but need not be entirely complementary (typically larger than about 200 bp, ranging between 200-1000 bp). hpRNA can also be rather small ranging in size from about 30 to about 42 bp, but not much longer than 94 bp (see WO04/073390, herein incorporated by reference). An ihpRNA is an intron-containing hairpin RNA, which has the same general structure as an hpRNA, but the RNA molecule additionally comprises an intron in the loop of the hairpin that is capable of being spliced in the cell in which the ihpRNA is expressed. The use of an intron minimizes the size of the loop in the hairpin RNA molecule following splicing, and this increases the efficiency of interference. See, for example, Smith et al (2000) Nature 407:319-320. In fact, Smith et al, show 100% suppression of endogenous gene expression using ihpRNA-mediated interference. In some embodiments, the intron is the ADHI intron 1. Methods for using ihpRNA interference to inhibit the expression of endogenous plant genes are described, for example, in Smith et al, (2000) Nature 407: 319-320; Waterhouse and Helliwell, (2003) Nat. Rev. Genet. 4:29-38; Helliwell and Waterhouse, (2003) Methods 30:289-295 and US2003180945, each of which is herein incorporated by reference. A transient assay for the efficiency of hpRNA constructs to silence gene expression in vivo has been described by Panstruga, et al. (2003). The chimeric gene for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene present in the plant. Thus, it is the loop region that determines the specificity of the RNA interference. See, for example, WO0200904 herein incorporated by reference.

Silencing RNA may also be artificial micro-RNA molecules as described e.g. in WO2005/052170, WO2005/ 047505 or US 2005/0144667, or ta-siRNAs as described in WO2006/074400 (all documents incorporated herein by reference).

A chimeric gene is an artificial gene constructed by operably linking fragments of unrelated genes or other nucleic acid sequences. In other words "chimeric gene" denotes a gene which is not normally found in a plant species or refers to any gene in which the promoter or one or more other regulatory regions of the gene are not associated in nature with a part or all of the transcribed nucleic acid, i. e. are heterologous with respect to the transcribed nucleic acid. More particularly, a chimeric gene is an artificial, i. e. non-naturally occurring, gene produced by an operable linkage of a promoter expressible in plants and the nucleic acid disclosed herein, such as the nucleic acid comprising the nucleic acid sequence of SEQ ID NO: 1 or of SEQ ID NO: 1 from nucleotide 64 to 840 or of SEQ ID NO: 5 or of SEQ ID NO: 5 from nucleotide 76 to 849, or of SEQ ID NO: 7, or of SEQ ID NO: 7 from nucleotide 85 to 861, or a functional fragment of any one of these sequences, or a nucleic acid sequence having at least 60% sequence identity to SEQ ID NO:1 or to SEQ ID NO: 1 from nucleotide 64 to 840 or of SEQ ID NO: 5 or of SEQ ID NO: 5 from nucleotide 76 to 849, or of SEQ ID NO: 7, or of SEQ ID NO: 7 from nucleotide 85 to 861 any of which encode a protein having cellulose:xyloglucan endotransglucosylase activity, wherein said plant expressible promoter is not naturally operably linked to said nucleic acid.

The term "heterologous" refers to the relationship between two or more nucleic acid or protein sequences that are derived from different sources. For example, a promoter is heterologous with respect to an operably linked nucleic acid sequence, such as a coding sequence, if such a combination is not normally found in nature. In addition, a particular sequence may be "heterologous" with respect to a cell or organism into which it is inserted (i.e. does not naturally occur in that particular cell or organism). For example, the chimeric gene disclosed herein is a heterologous nucleic acid.

The expression "operably linked" means that said elements of the chimeric gene are linked to one another in such a way that their function is coordinated and allows expression of the coding sequence, i.e. they are functionally linked. By way of example, a promoter is functionally linked to another nucleic acid sequence when it is capable of ensuring transcription and ultimately expression of said nucleic acid sequence, and two protein encoding nucleotide sequences, e.g. a signal peptide encoding nucleic acid sequence and a nucleic acid sequence encoding a protein having cellulose: xyloglucan endotransglucosylase activity, are functionally or operably linked to each other if they are connected in such a way that a fusion protein of first and second protein or polypeptide can be formed.

A promoter may be any regulatory element being able to drive expression of a gene in a desired host cell or organism, such as plant cells and plants, bacteria or yeast. For the case of plants, use may be made of any promoter sequence of a gene which is naturally expressed in plants, such as for example promoters of bacterial, viral or plant origin.

Promoters may generally be constitutive or inducible.

A plant expressible promoter can be a constitutive promoter, i.e. a promoter capable of directing high levels of expression in most cell types (in a spatio-temporal independent manner).

Examples of plant expressible constitutive promoters include promoters of bacterial origin, such as the octopine synthase (OCS) and nopaline synthase (NOS) promoters from *Agrobacterium*, but also promoters of viral origin, such as that of the cauliflower mosaic virus (CaMV) 35S transcript (Hapster et al., 1988) or 19S RNA genes (Odell et al., 1985; U.S. Pat. No. 5,352,605; WO 84/02913; Benfey et al., 1989), promoters of the cassava vein mosaic virus (CsVMV; WO 97/48819, U.S. Pat. No. 7,053,205), the circovirus (AU 689 311) promoter, the sugarcane bacilliform badnavirus (ScBV) promoter (Samac et al., 2004), the figwort mosaic virus (FMV) promoter (Sanger et al., 1990), the subterranean clover virus promoter No 4 or No 7 (WO 96/06932) and the enhanced 35S promoter as described in U.S. Pat. No. 5,164,316, U.S. Pat. No. 5,196,525, U.S. Pat. No. 5,322,938, U.S. Pat. No. 5,359,142 and U.S. Pat. No. 5,424,200. Among the promoters of plant origin, mention will be made of the promoters of the plant ribulose-bisphosphate carboxylase/oxygenase (Rubisco) small subunit promoter (U.S. Pat. No. 4,962,028), the promoter of the *Arabidopsis thaliana* histone H4 gene (Chabouté et al., 1987), the ubiquitin promoters (Holtorf et al., 1995) of Maize, Rice and sugarcane, the Rice actin 1 promoter (Act-1, U.S. Pat. No. 5,641,876), the histone promoters as described in EP 0 507 698 A1 and the Maize alcohol dehydrogenase 1 promoter (Adh-1).

Alternatively, a promoter sequence specific for particular regions, tissues or organs of plants can be used to express the protein disclosed herein. Examples of such promoters that can be used are tissue-specific or organ-specific promoters like organ primordia-specific promoters (An et al., 1996), stem-specific promoters (Keller et al., 1988), mesophyll-specific promoters (such as the light-inducible Rubisco promoters), fiber-specific promoters such as the fiber-specific promoter of the fiber-specific β-tubulin gene (as described in WO0210377), of a fiber-specific actin gene (as described in WO0210413), of a fiber specific lipid transfer protein gene (as described in U.S. Pat. No. 5,792,933), the promoter from the seed coat and fiber-specific protease (Hou et al., 2008), the promoter from fiber-specific R2R3 MYB gene from cotton (Pu et al., 2008), a promoter from an expansin gene from cotton (WO9830698), a promoter from a chitinase gene in cotton (US2003106097), the promoter of CesA1 (U.S. Pat. No. 6,271,443), the F286 promoter (see US2003/106097), the cotton E6 promoter (see U.S. Pat. No. 6,096,950) or the promoters of the fiber specific genes described in U.S. Pat. No. 6,259,003 or U.S. Pat. No. 6,166,294 or WO96040924), root-specific promoters (Keller et al., 1989), vascular tissue-specific promoters (Peleman et al), seed-specific promoters (Datla, R. et al., 1997), especially the napin promoter (EP 255 378 A1), the phaseolin promoter, the glutenin promoter, the *petunia* FBP7 promoter, the helianthinin promoter (WO 92/17580), the albumin promoter (WO 98/45460), the oleosin promoter (WO 98/45461), the SAT1 promoter or the SAT3 promoter (PCT/US98/06978), and the like.

Use may also be made of an inducible promoter advantageously chosen from the phenylalanine ammonia lyase (PAL), HMG-CoA reductase (HMG), chitinase, glucanase, proteinase inhibitor (PI), PR1 family gene, nopaline synthase (nos) and vspB promoters (U.S. Pat. No. 5,670,349, Table 3), the HMG2 promoter (U.S. Pat. No. 5,670,349), the apple beta-galactosidase (ABG1) promoter and the apple aminocyclopropane carboxylate synthase (ACC synthase) promoter (WO 98/45445).

Suitable promoters for (inducible) expression in bacteria are well-known in the art and include the T3 or T7 promoters (in connection with the expression of a T3 or T7 RNA polymerase), the lac promoter, the trc and tac promoters, the phage promoter pL, the tetA promoter and the PPBAD or rhaPBAD promoters.

Promoters suitable for expression in yeasts are well-known in the art and include the TEF promoter, the CYC1 promoter, the ADH1 promoter, the AOX1 promoter (methanol inducible) and the GAL promoter and variants thereof.

The (plant expressible) promoter may for example be altered to contain e. g. "enhancer DNA" to assist in elevating gene expression. As is well-known in the art, certain DNA elements can be used to enhance the transcription of DNA. These enhancers are often found 5' to the start of transcription in a promoter that functions in eukaryotic cells, but can often be inserted upstream (5') or downstream (3') to the coding sequence. In some instances, these enhancer DNA elements are introns. Among the introns that are useful as enhancer DNA are the 5' introns from the rice actin 1 gene (see U.S. Pat. No. 5,641,876), the rice actin 2 gene, the *Arabidopsis* histone 4 intron, the maize alcohol dehydrogenase gene, the maize heat shock protein 70 gene (see U.S. Pat. No. 5,593,874), the maize shrunken 1 gene, the light sensitive 1 gene of *Solanum tuberosum*, and the heat shock protein 70 gene of *Petunia hybrida* (see U.S. Pat. No. 5,659,122). Thus, as contemplated herein, a promoter or promoter region includes variations of promoters derived by inserting or deleting regulatory regions, subjecting the promoter to random or site-directed mutagenesis etc. The activity or strength of a promoter may be measured in terms of the amounts of RNA it produces, or the amount of protein accumulation in a cell or tissue, relative to a promoter whose transcriptional activity has been previously assessed.

The chimeric gene may also comprise a transcription termination or polyadenylation sequence, e. g. one operable in a plant cell. As a transcription termination or polyadenylation sequence, use may be made of any corresponding sequence of bacterial origin, such as for example the nos terminator of *Agrobacterium tumefaciens*, of viral origin, such as for example the CaMV 35S terminator, or of plant origin, such as for example a histone terminator as described in published Patent Application EP 0 633 317 A1.

Within the scope of the present disclosure, use may also be made, in combination with the promoter and the nucleic acid disclosed herein, of other regulatory sequences, which are located between said promoter and said nucleic acid. Non-limiting examples of such regulatory sequences include transcription activators ("enhancers") or introns as described elsewhere in this application. Other suitable regulatory sequences include 5' UTRs. As used herein, a 5'UTR, also referred to as leader sequence, is a particular region of a messenger RNA (mRNA) located between the transcription start site and the start codon of the coding region. It is involved in mRNA stability and translation efficiency. For example, the 5' untranslated leader of a *petunia* chlorophyll a/b binding protein gene downstream of the 35S transcription start site can be utilized to augment steady-state levels of reporter gene expression (Harpster et al., 1988). WO95/006742 describes the use of 5' non-translated leader sequences derived from genes coding for heat shock proteins to increase transgene expression. The translation activators of the tobacco mosaic virus (TMV) leader described in Application WO 87/07644 as well as that of the tobacco etch virus (TEV) leader described by Carrington & Freed 1990, J. Virol. 64: 1590-1597 may also be used in the present invention.

The chimeric gene may further comprise a nucleotide sequence encoding a protein targeting sequence for targeting the expressed protein to specific organelles or compartments within the host cell, or for secretion.

A protein targeting sequence is a short (3-60 amino acids long) amino acid sequence that directs the transport of a protein within or outside the cell. Protein targeting peptides may also be called signal peptides (for secretion), transit peptides (for targeting to plastids), or protein retention sequences.

A suitable signal sequence for secretion of protein expressed in yeasts such as *Pichia pastoris* is the signal sequence of the α factor mating protein (Cregg et al., 1993). An example for a signal peptide for secretion of fused proteins in plants is that of the PR1a protein of *Nicotiana tabacum* (Cornelissen et al. 1986).

Fusion of such signal sequences to the protein disclosed herein by linking DNA fragments encoding the respective protein and the signal sequence can be achieved using standard recombinant DNA techniques.

In one embodiment, the present invention relates to a vector comprising the chimeric gene described herein.

The vector can be, e. g., a plasmid, cosmid, virus, bacteriophage or another vector used conventionally e.g. in genetic engineering.

The nucleic acid molecule of the present invention may be inserted into several commercially available vectors. Non-limiting examples include prokaryotic plasmid vectors, such as the pUCseries, pBluescript (Stratagene), the pET-series of expression vectors (Novagen) or pCRTOPO (Invitrogen), lambda gt11, pJOE, the pBBR1-MCS series, pJB861, pBSMuL, pBC2, pUCPKS, pTACT1 and vectors compatible with expression in eukaryotic cells, such as yeast or mammalian cells, like pREP (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRSVgpt, pRSVneo, pSV2-dhfr, p1ZD35, Okayama-Berg cDNA expression vector pcDV1 (Pharmacia), pRc/CMV, pcDNA1, pcDNA3 (Invitrogen), pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for the yeast *Pichia pastoris* comprise e.g. the plasmids pA0815, pPICZ, pPICZα, pPIC9K and pPIC3.5K (all Invitrogen).

Suitable vectors for introduction into plants include those disclosed in Cornelissen and Vandewiele (1989), Lindbo (2007), Gritch et al (2006) or Wagner et al (2004).

Also described herein is a host cell comprising the chimeric gene or the vector described herein. Suitable prokaryotic host cells comprise e.g. bacteria of the genera *Escherichia*, *Streptomyces*, *Salmonella* or *Bacillus*. Suitable eukaryotic host cells are e.g. yeasts such as *Saccharomyces cerevisiae* or *Pichia pastoris*. Insect cells suitable for expression are e.g. *Drosophila* S2 or *Spodoptera* Sf9 cells. Plant cells suitable for the present invention include any plant cell comprising essentially the genetic information necessary to define a plant, which may, apart from the chimeric gene disclosed herein, be supplemented by one or more further transgenes. Cells may be derived from the various organs and/or tissues forming a plant, including but not limited to fruits, seeds, embryos, reproductive tissue, meristematic regions, callus tissue, leaves, roots, shoots, flowers, vascular tissue, gametophytes, sporophytes, pollen, and microspores.

In one example, the host cell of the invention further comprises at least one further chimeric gene comprising a (plant expressible) promoter, a nucleic acid sequence encoding a protein able to synthesize xyloglucan in said host cell, and a transcription termination and polyadenylation region. For example, one chimeric gene could comprise a nucleic acid sequence encoding CsIC4 from *Arabidopsis* (Cocuron et al., 2007) in combination with another chimeric gene comprising a nucleic acid encoding an alpha-xylosyltransferase XT1 from *Arabidopsis* (Faik et al., 2002). As described further below, this embodiment serves for the production of cellulose covalently linked to xyloglucan (oligosaccharides) in case the host cell does not produce xyloglucan by itself.

Also disclosed herein is a plant, plant part or seed comprising the chimeric gene described herein, the vector described herein or the plant cell described herein.

The plant of the present invention can be any plant. Non-limiting examples of plants of the invention include wheat, cotton, canola and other oilseed rape, rice, corn, soy bean, sorghum, sunflower, tobacco, sugar beet, maize, barley, tomato, mango, peach, apple, pear, strawberry, banana, melon, potato, carrot, lettuce, cabbage, onion, sugar cane, pea, field beans, poplar, grape, citrus, alfalfa, rye, oats, turf and forage grasses, flax, nut producing plants and wood producing plants such as *Pinus*, *Prunus*, *Pseudotsuga*, *Eucalyptus*, *Picea*, *Larix*, *Thuja*, *Abies*, *Khaya*, *Acer*, *Lophira*, *Fagus*, *Diospyros*, *Quercus*, *Tilia*, *Populus*, *Platanus*, *Tectona*, *Robinia*, *Ulmus* and *Juglans*.

Plant parts include, in addition to the examples listed above for plant cells, cells, tissues or organs, seed pods, seeds, severed parts such as roots, leaves, flowers, pollen, etc. The term "plant" also includes progeny of plants which retain the distinguishing characteristics of the parents, such as seed obtained by selfing or crossing, e.g. hybrid seed, hybrid plants and plant parts derived therefrom.

Seed is formed by an embryonic plant enclosed together with stored nutrients by a seed coat. It is the product of the ripened ovule of gymnosperm and angiosperm plants, to the latter of which soybean belongs, which occurs after fertilization and to a certain extent growth within the mother plant. The seed disclosed herein retains the distinguishing characteristics of the parents, such as seed obtained by selfing or crossing, e.g. hybrid seed (obtained by crossing two inbred parental lines).

The plant cell, plant part, plant or seed can be from the plants specified above as well as from genetically modified homologues of these plants.

For the case of cotton, the cotton plant cell, plant part, plant or seed can be from any existing cotton variety. For example, the cotton plant cell can be from a variety useful for growing cotton. The most commonly used cotton varieties are *Gossypium barbadense*, *G. hirsutum*, *G. arboreum* and *G. herbaceum*. Further varieties include *G. africanum* and *G. raimondii*.

Furthermore, the invention relates to progeny of the plant of the invention or the seed of the invention.

The present invention also relates to a method of producing a transgenic plant comprising (a) providing a chimeric gene described herein or the vector described herein; and (b) introducing said chimeric gene or said vector into a plant.

"Introducing" in connection with the present application relates to the placing of genetic information in a plant cell or plant by artificial means. This can be effected by any method known in the art for introducing RNA or DNA into plant cells, tissues, protoplasts or whole plants. In addition, "introducing" also comprises introgressing genes as defined further below.

A number of methods are available to transfer DNA into plant cells. *Agrobacterium*-mediated transformation of cotton has been described e.g. in U.S. Pat. No. 5,004,863, in U.S. Pat. No. 6,483,013 and WO2000/71733.

Plants may also be transformed by particle bombardment: Particles of gold or tungsten are coated with DNA and then shot into young plant cells or plant embryos. This method also allows transformation of plant plastids. Cotton transformation by particle bombardment is reported e.g. in WO 92/15675.

Viral transformation (transduction) may be used for transient or stable expression of a gene, depending on the nature of the virus genome. The desired genetic material is packaged into a suitable plant virus and the modified virus is allowed to infect the plant. The progeny of the infected plants is virus free and also free of the inserted gene. Suitable methods for viral transformation are described or further detailed e. g. in WO 90/12107, WO 03/052108 or WO 2005/098004.

"Introgressing" means the integration of a gene in a plant's genome by natural means, i. e. by crossing a plant comprising the chimeric gene described herein with a plant not comprising said chimeric gene. The offspring can be selected for those comprising the chimeric gene.

Further transformation and introgression protocols can also be found in U.S. Pat. No. 7,172,881.

In a further aspect, the present application discloses a method of producing a plant or of strengthening a plant or a part thereof such as a plant cell wall, comprising: introducing a chimeric gene comprising a promoter expressible in plants, the nucleic acid described herein above (i. e. that encoding a protein having cellulose:xyloglucan endotransglucosylase activity), and a transcription termination and polyadenylation region; or growing the plant described herein or growing a plant from the seed disclosed herein. The chimeric gene introduced may be the chimeric gene as described herein above including all variations related thereto.

Further disclosed herein is a method of altering at least one fiber property in a fiber-producing plant or for strengthening a plant comprising expressing the chimeric gene described herein or the vector described herein in said fiber-producing plant or plant.

In one example, the fiber property is fiber strength and/or resistance to enzymatic digestion. In one example, the fiber strength and/or resistance to enzymatic digestion is increased.

In another example, strengthening a plant includes strengthening its stem, increasing resistance to lodging (e. g. flooding, heavy rain or wild damage) and increasing resistance to infection by pathogens.

In a further example of the method of producing a plant or of strengthening a plant described above, the method further comprises growing said plant until seed is produced.

The present invention also relates to a method of producing a protein comprising culturing the host cell described herein under suitable conditions and isolating the protein produced. Said host cell expresses or over-expresses the protein of the invention having cellulose:xyloglucan endotransglucosylase activity as described above. Accordingly, said protein of the invention is produced in and isolated from the host cell. In case that the host cell produces the protein of the invention and secretes it to the surrounding media, e. g. due to a suitable signal peptide attached to the protein, isolation denotes separation of the media comprising the protein from the host cell. Said media may then be the subject of further purification steps (see below).

Suitable conditions for culturing a prokaryotic or eukaryotic host are well known to the person skilled in the art. For example, suitable conditions for culturing bacteria are growing them under aeration in Luria Bertani (LB) medium. To increase the yield and the solubility of the expression product, the medium can be buffered or supplemented with suitable additives known to enhance or facilitate both. *E. coli* can be cultured from 4 to about 37° C., the exact temperature or sequence of temperatures depends on the molecule to be over-expressed. In general, the skilled person is also aware that these conditions may have to be adapted to the needs of the host and the requirements of the polypeptide expressed. In case an inducible promoter controls the nucleic acid of the invention in the vector present in the host cell, expression of the polypeptide can be induced by addition of an appropriate inducing agent Suitable expression protocols and strategies are known to the skilled person.

Suitable expression protocols for eukaryotic cells are well known to the skilled person and can be retrieved e.g. from Sambrook, 2001.

Suitable media for insect cell culture are e.g. TNM+10% FCS or SF900 medium. Insect cells are usually grown at 27° C. as adhesion or suspension culture.

Methods of isolation of the polypeptide produced are well-known in the art and comprise without limitation method steps such as ammonium sulphate precipitation, ion exchange chromatography, gel filtration chromatography (size exclusion chromatography), affinity chromatography, high pressure liquid chromatography (HPLC), reversed phase HPLC, disc gel electrophoresis or immunoprecipitation, see, for example, in Sambrook, 2001.

In another aspect, the present application discloses the use of the protein described herein, the isolated nucleic acid described herein, the chimeric gene described herein or the vector described herein for altering fiber properties in a fiber-producing plant or for strengthening a plant.

Also disclosed herein is a method of growing a plant comprising (a1) providing the transgenic plant described herein or produced by the method of producing a plant described herein; or (a2) introducing a chimeric gene described herein in a plant; and (b) growing the plant of (a1) or (a2); and optionally (c) harvesting harvestable parts produced by said plant.

The nucleic acid sequences and amino acid sequences according to the invention can be used to identify other proteins, such as orthologous proteins or homologous proteins, with HTG activity or, more particularly, with CXE activity. Homologous or orthologous sequences encoding HGT proteins can be identified using methods known in the art. Homologous nucleotide sequence may be identified and isolated by hybridization under stringent conditions using as probes a nucleic acid comprising the nucleotide sequence of any one of SEQ ID NOs: 1, 5 and 7 or part thereof. Other sequences encoding HTG proteins may also be obtained by DNA amplification using oligonucleotides specific for genes encoding HTG as primers, such as but not limited to oligonucleotides comprising or consisting of about 20 to about 50 consecutive nucleotides from any one of SEQ ID NOs: 1, 5 and 7 or its complement. Homologous genes encoding HTG proteins can be identified in silico using Basic Local Alignment Search Tool (BLAST) homology search with other nucleotide or amino acid sequences. Functionality of the identified homologous genes encoding HTG, and in particular their MXE and CXE activities can be validated using the methods described herein.

Also disclosed herein is a method of detecting the expression of a nucleic acid or protein, comprising (a) providing the plant cell or the plant disclosed herein, wherein said transgene is the nucleic acid or protein described herein (i. e. that encoding a protein having cellulose:xyloglucan endotransglucosylase activity); and (b) detecting the expression level of the nucleic acid or protein.

The term "expression of nucleic acid or protein" relates to the transcription and optionally the translation of the transcribable and translatable part of the chimeric gene disclosed herein using appropriate expression control elements that function in plant cells.

"Detecting the expression of the nucleic acid or protein" can be effected in multiple ways. The protein has cellulose: xyloglucan endotransglucosylase activity. Accordingly, expression may be detected using a substrate which can be converted into a visually detectable product, wherein said product may be detected by the appropriate means which depend on the color of said product or of the wavelength of the light emitted by said product. Suitable detection means are disclosed in the example section. Furthermore, expression of a nucleic acid sequence can be measured by PCR methods including the one disclosed in Zanoni et al. (2009,) and in Logan, Edwards and Saunders (2009), by sequencing techniques including that disclosed in the Illumina datasheet "mRNA expression analysis" (2010) available on the world wide web at illumina.com/documents/products/datasheets/datasheet_mrna_expression.pdf, and by hybridization techniques well-known in the art.

Also disclosed herein is a method for producing a cellulosic material with improved properties, the method comprising contacting, e. g. in an aqueous medium, in the presence of xyloglucan or xyloglucan oligosaccharide or xyloglucan or xyloglucan oligosaccharide to which an organic or inorganic molecule is covalently attached, cellulosic material with an effective amount of the protein of the invention.

Improved properties include increased strength or reactivity or other properties such as color (e.g. permanent dyeing of clothing, outdoor timber etc.), charge (acidic or basic), unusual paper surfaces e.g. for banknotes and legal documents, medical substances e.g. antibiotics or drugs, laboratory reagents e.g. indicator papers that would not lose the indicator during prolonged exposure to water.

The protein of the invention can be used to attach cellulose or cello-oligosaccharides covalently to xyloglucan or xyloglucan oligosaccharides, wherein said xyloglucan or xyloglucan oligosaccharides have optionally attached thereto, e.g. at the reducing terminus, various organic or inorganic compounds, which would augment the value of the celluloses.

In one example, the cellulosic material is selected from or comprised in fabric (textiles such as cotton or linen), paper, cellulose derivatives such as carboxymethylcellulose or cellulose acetate, packaging such as cardboard, building material (e. g. timber and chipboard), thickening agents such as those including and derived from xanthan gum, a medical dressing such as cotton wool and gauzes, cellophane, dialysis tubing and resin for chromatography columns.

For example, for altering the color of a material, the molecule attached to xyloglucan would be a dye. Such combination could result in a permanent dyeing of e. g. clothing or outdoor timber while achieved under very mild conditions and with no polluting by-products.

Other properties which can be altered due to attachment of a molecule with respective properties to xyloglucan within the method of producing a cellulosic material with improved properties include charge (acidic or basic), unusual paper surfaces e.g. for banknotes and legal documents, medical substances e.g. antibiotics or drugs, laboratory reagents e.g. indicator papers that would not lose the indicator during prolonged exposure to water, and numerous others.

Accordingly, in one example the method for producing a cellulosic material with improved properties includes attaching a molecule having or conferring a desired property to xyloglucan or xyloglucan oligosaccharides not having such molecule attached, said attaching taking place prior to contacting said xyloglucan or xyloglucan oligosaccharides with said cellulosic material and the protein of the invention. The molecule may be organic or inorganic. Attaching organic substances to the reducing terminus of a xyloglucan oligosaccharide can be achieved by the oligosaccharidyl-1-amino-1-deoxyalditol method disclosed in WO97/011193.

Further provided is a method for producing a cellulosic material with improved properties, said method comprising providing a plant according to the invention and harvesting the cellulosic material from said plant.

Harvesting the cellulosic material can be harvesting of the plant of the invention, comprising the cellulosic material, using conventional methods. Harvesting the cellulosic material can also be harvesting parts of the plants comprising the cellulosic material of the invention using conventional methods, such as using standard machine harvesters.

The cellulosic material can further be isolated from the harvested material, or purified from the harvested material.

Also disclosed is cellulosic material produced by the method for producing a cellulosic material disclosed herein.

Also disclosed herein is cellulosic material comprising cellulosic material covalently attached to xyloglucan or xyloglucan oligosaccharides via a glycosidic bond. In particular, said cellulosic material comprises cellulose or cello-oligosaccharides linked via a beta-glucosidic bond to xyloglucan or an oligosaccharide thereof.

In one example of said cellulosic material, an organic or inorganic molecule is covalently attached to said xyloglucan or xyloglucan oligosaccharide as described above. The effect of such modification is discussed elsewhere in this application.

Also disclosed herein is a kit comprising (a) a cellulosic material not having xyloglucan or xyloglucan oligosaccharide attached thereto and (b) xyloglucan and/or xyloglucan oligosaccharide. The kit is meant to provide the components to manufacture the cellulosic material of the invention as described elsewhere. Optionally, the kit may further comprise the protein of the invention as described herein.

Further provided is an antibody directed to the protein according to the invention. An Antibody refers to intact molecules or fragments thereof which are capable of binding an epitope of the protein of the invention. Antibodies that bind the protein of the invention can be prepared using intact polypeptides or fragments containing small peptides of interest for immunization.

Also provided is a method of producing food or feed, such as oil, meal, grain, starch, flour or protein, or an industrial product such as biofuel, fiber, industrial chemicals, a pharmaceutical or a nutraceutical, said method comprising obtaining the plant or a part thereof according to the invention and preparing the food, feed or industrial product from the plant or part thereof.

"High stringency conditions" or "high stringency hybridization conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denatured carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency conditions" or "moderate stringency hybridization conditions" refers to conditions equivalent to hybridization in the above described solution but at about 60-62° C. Moderate stringency washing may be done at the hybridization temperature in 1×SSC, 0.1% SDS.

"Low stringency" or "low stringency hybridization conditions" refers to conditions equivalent to hybridization in the above described solution at about 50-52° C. Low stringency washing may be done at the hybridization temperature in 2×SSC, 0.1% SDS. See also Sambrook et al. (1989) and Sambrook and Russell (2001).

The transformed plant cells and plants disclosed herein or obtained by the methods described herein may contain, in addition to the chimeric gene described above, at least one other chimeric gene comprising a nucleic acid encoding an expression product of interest. Examples of such expression product include RNA molecules or proteins, such as for example an enzyme for resistance to a herbicide. Herbicide-resistant cotton plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992), the genes encoding a *Petunia* EPSPS (Shah et al., 1986), a Tomato EPSPS (Gasser et al., 1988), or an *Eleusine* EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943,801 or 12/362,774. Plants comprising other genes that confer glyphosate tolerance, such as decarboxylase genes, are described in e.g. U.S. patent application Ser. Nos. 11/588,811, 11/185,342, 12/364,724, 11/185,560 or 12/423,926.

Other herbicide resistant cotton plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant cotton plants are also plants that are made tolerant to the herbicides inhibiting the enzyme hydroxyphenylpyruvatedioxygenase (HPPD). HPPD is an enzyme that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate dehydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant cotton plants are plants that are made tolerant to acetolactate synthase (ALS) inhibitors. Known ALS-inhibitors include, for example, sulfonylurea, imidazolinone, triazolopyrimidines, pryimidinyoxy (thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 07/024782 and U.S. Patent Application No. 61/288,958.

Other cotton plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Further expression products of interest confer insect resistance to a cotton plant, i.e. resistance to attack by certain target insects. Such plants can be obtained by genetic transformation, or by selection of plants containing a mutation imparting such insect resistance.

Insect-resistant plants include any plant containing at least one transgene comprising a coding sequence encoding:
1) an insecticidal crystal protein from *Bacillus thuringiensis* or an insecticidal portion thereof, such as the insecticidal crystal proteins listed by Crickmore et al. (1998,), updated by Crickmore et al. (2005) at the *Bacillus thuringiensis* toxin nomenclature, online at:

lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001; Schnepf et al. 2006) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5);

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein).

Also included are insect-resistant transgenic plants comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

Insect-resistant plants further include plants containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Further additional traits confer tolerance to abiotic stresses. Plants with such tolerance can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.

2) plants which contain a stress tolerance enhancing transgene capable of reducing the expression and/or the activity of the PARG encoding genes of the plants or plants cells, as described e.g. in WO 2004/090140.

3) plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in EP 04077624.7, WO 2006/133827, PCT/EP07/002433, EP 1999263, or WO 2007/107326.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549
b) Plants, such as cotton plants, containing an altered form of rsw2 or rsw3 homologous nucleic acids as described in WO 2004/053219
c) Plants, such as cotton plants, with increased expression of sucrose phosphate synthase as described in WO 01/17333
d) Plants, such as cotton plants, with increased expression of sucrose synthase as described in WO 02/45485
e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938
f) Plants, such as cotton plants, having fibers with altered reactivity, e.g. through the expression of N-acetylglucosaminetransferase gene including nodC and chitin synthase genes as described in WO 2006/136351

The transformed plant cells and plants obtained by the methods described herein may be further used in breeding procedures well known in the art, such as crossing, selfing, and backcrossing. Breeding programs may involve crossing to generate an F1 (first filial) generation, followed by several generations of selfing (generating F2, F3, etc.). The breeding program may also involve backcrossing (BC) steps, whereby the offspring is backcrossed to one of the parental lines, termed the recurrent parent.

Accordingly, also disclosed herein is a method for producing plants comprising the chimeric gene disclosed herein comprising the step of crossing the cotton plant disclosed herein with another plant or with itself and selecting for offspring comprising said chimeric gene.

The transformed plant cells and plants obtained by the methods disclosed herein may also be further used in subsequent transformation procedures, e. g. to introduce a further chimeric gene.

The plants or seed comprising the chimeric gene disclosed herein or obtained by the methods disclosed herein may further be treated with cotton herbicides such as Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; cotton insecticides such as Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl) methyl](2,2-difluorethyl)amino]furan-2(5H)-on, Thiodicarb, Avermectin, Flonicamid, Pyridalyl, Spiromesifen, Sulfoxaflor; and cotton fungicides such as Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin.

The sequence listing contained in the file named "BCS13-2019_ST25.txt", which is 30 kilobytes (size as measured in Microsoft Windows®), contains 8 sequences SEQ ID NO: 1 through SEQ ID NO: 8 is filed herewith by electronic submission and is incorporated by reference herein.

The figures show:

FIG. 1: Zymogram of native PAGE of extract of MXE activity. Crude extract (A) or ammonium sulphate precipitate (ASP) (B) was run on native PAGE. One lane was stained with Coomassie Blue (CB). Three lanes of the electrophoresed gels were excised and washed twice in 0.3 M citrate buffer (pH 6.3) for 15 min. Enzyme activities were detected by overlaying the lane with paper impregnated with MLG and XXXG-SR (conjugate of sulphorhodamine and a heptasaccharide of xyloglucan (Xyl3.Glc4)) (M), XyG (xyloglucan) and XXXG-SR (X), or just XXXG-SR (C). Light bands on the dark background indicate polysaccharide-to-oligosaccharide transglucosylation; in the case of (C) the polysaccharide involved was the cellulose of the paper itself.

Figure 2:
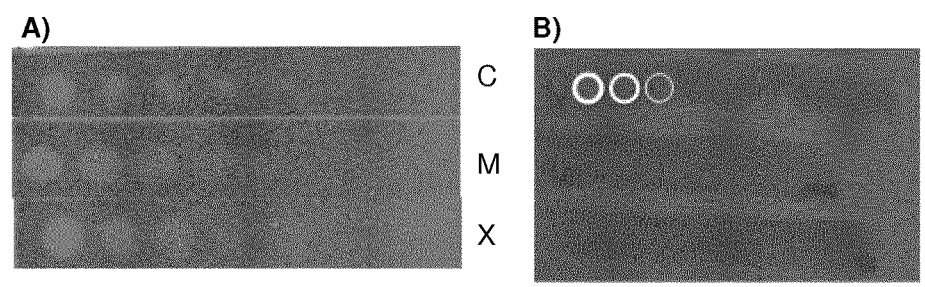

FIG. 2: Dot blot paper confirming CXE activity. A) Three test paper strips were loaded (3 µl each, 8 spots) with a 2-fold dilution series of ASP enzyme in citrate (0.3 M, pH 6.3). The strips were incubated in humid conditions for 1 h, then dried at room temperature. The strips were washed in ethanol/formic acid/water (EFW) and photographed. B) The strips were washed in 6 M NaOH at 37° C. overnight, rinsed in water, dried, and photographed again. The papers shrank in size during the wash. Circles show the remaining firmly bound endotransglucosylase product attributable to cellulose-to-XXXG transglycosylation. C=CX; M=MXE; X=XET.

Figure 3:
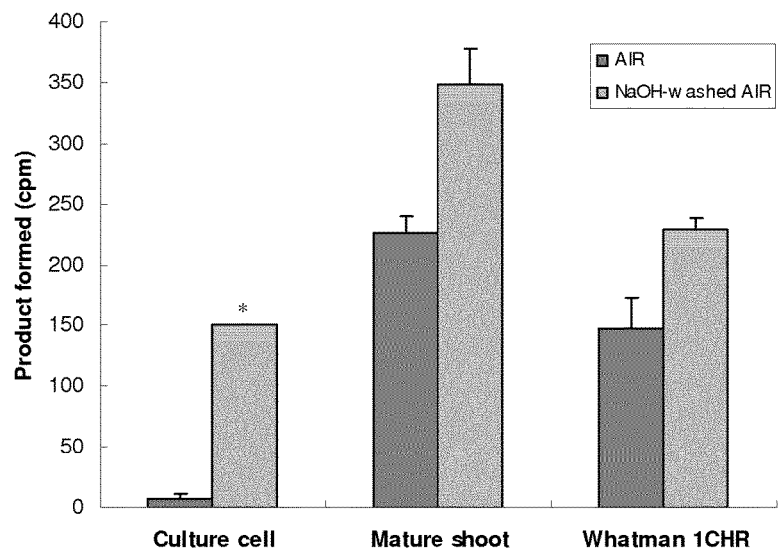

FIG. 3: Natural cellulose as donor for HTG. Ground culture cells and mature shoots were washed in 75% EtOH until chlorophyll removed, and dried. A portion of the AIR (alcohol-insoluble residue) was incubated in 6 M NaOH at 37° C. overnight, then washed in water to remove the alkali, lyophilized, and stored. Each substrate (10 mg) was rehydrated overnight, and excess liquid was removed prior to assay. The solid substrate was mixed with [$^3$H]XXXGol (reduced XXXG (i.e., Xyl3.Glc3.glucitol) (2 kBq), ASP, and citrate buffer (0.3 M, pH 6.3, 97 µl). After 2 h, the reaction was stopped with formic acid (FA) (30 µl), and the solids were washed in water until void of remaining free [$^3$H] XXXGOL. The solids (in 1 ml water) were transferred to scintillation vials and incubated with scintillant overnight before $^3$H testing. Each sample tested in triplicate, ±SD shown. * n=1.

Figure 4:
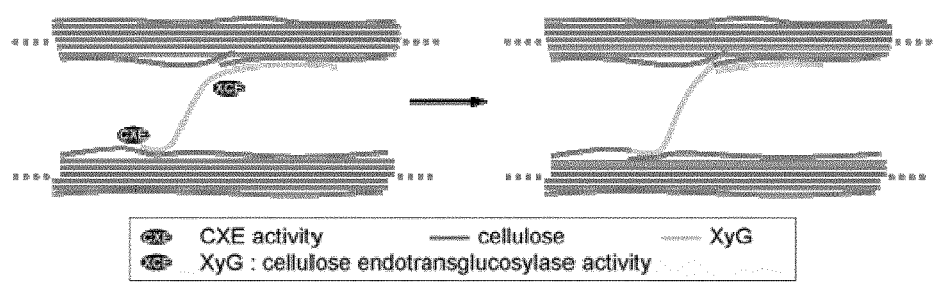

FIG. 4: Potential of activities to covalently link cellulose microfibrils.

Figure 5:
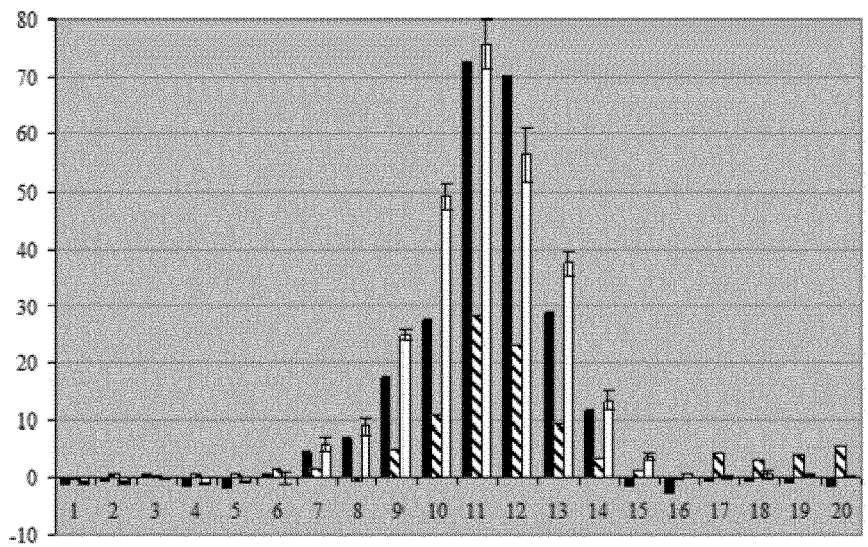

FIG. 5: Corrected radioactivity (cpm for MXE and XET, cpm/6 for CXE) of fractions 1-20 containing three endo-transglucosylase activities (XET (diagonally striped bars), MXE (black bars), CXE (white bars)) after isoelectric focusing of ammonium-sulphate-precipitated *Equisetum* proteins.

Figure 6:
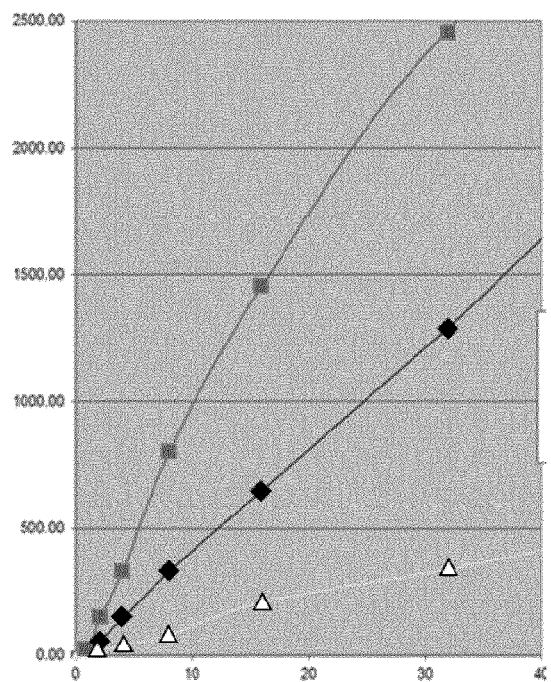

FIG. 6: Timescale of XET, MXE and CXE activity of the HTG protein expressed in *Pichia*. XET activity is indicated with diamonds, MXE activity is indicated with squares, and CXE activity is indicated with triangles. X-axis: Time (min); Y-axis: radioactivity incorporated (cpm).

Figure 7:
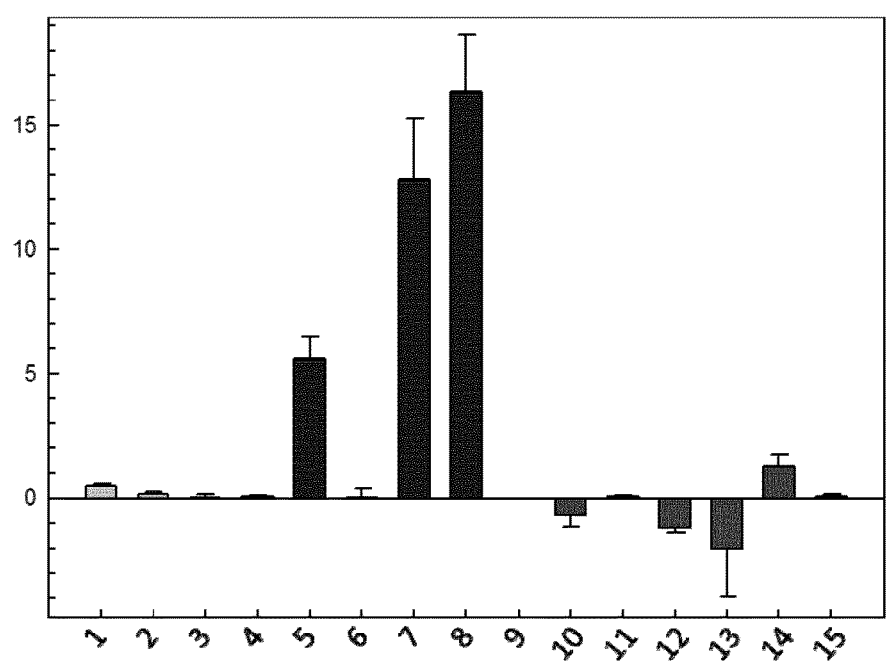

FIG. 7: Acceptor substrate-specificity of recombinant HTG in an assay in which barley mixed-linkage glucan was used as donor. Percentage incorporation is shown for the potential acceptor substrates (all $^3$H-labeled) (1→4)-β-mannohexaitol (1), cellohexaitol (2), (1→4)-β-galactohexaitol (3), (1→4)-α-galacturonohexaitol (4), XXLGol (5), GGXXXGol (6), XXXGol (7), GXXXGol (8), maltohexaitol (9), cellulase-generated heptasaccharides and octasaccharides of MLG (10), (1→4)-β-xylohexaitol (11), lichenase-generated hepta- to decasaccharides of MLG (12), lichenase-generated octasaccharide of MLG (13), lichenase-generated heptasaccharide of MLG (14), and laminaritetraitol (15). The abbreviated nomenclature of the xyloglucan oligosaccharides (XXLGol, GGXXXGol, XXXGol, GXXGol) is as explained by Fry et al. (1993).

FIG. 8: Alignment of nucleotide (A) and amino acid (B) sequences of the sequences of SEQ ID NOs 1, 5 and 7, and SEQ ID NOs 2, 6 and 8, respectively.

Figure 9:
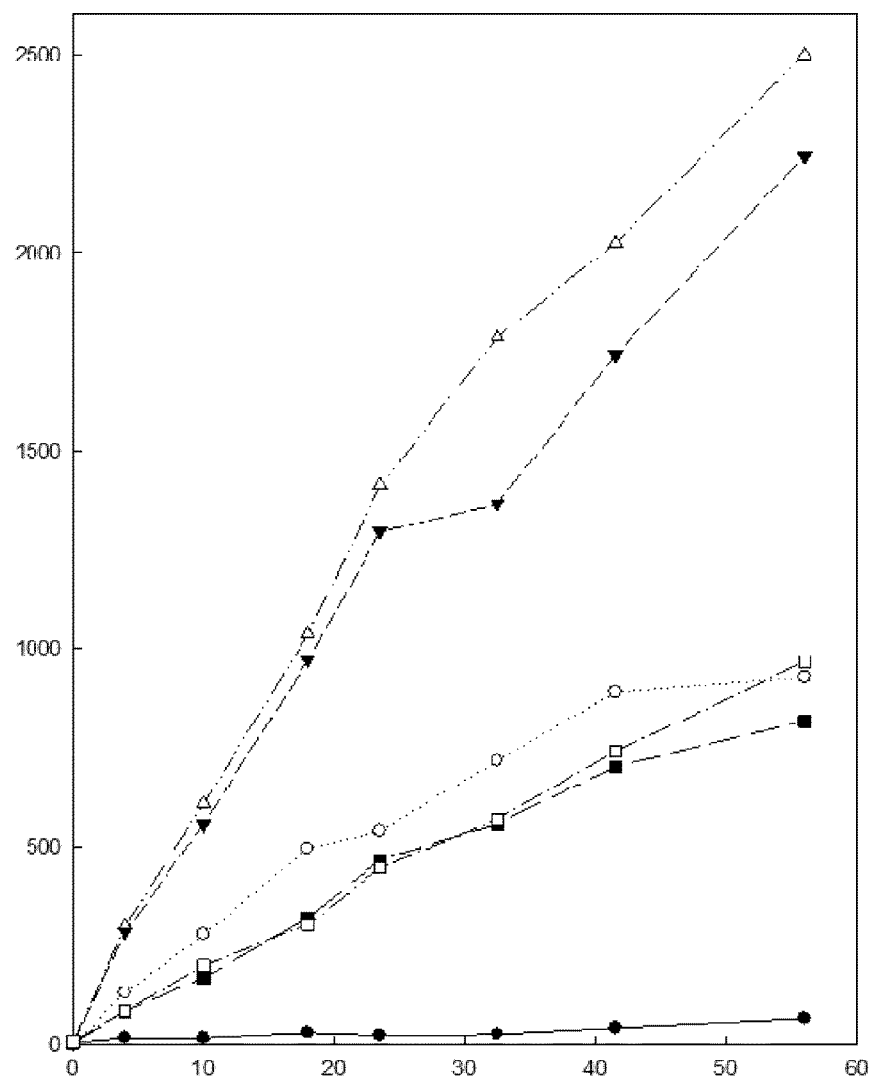

FIG. 9: Timescale of XET, MXE and CXE activity of the HTG protein expressed in *Pichia* in presence and absence of BSA. XET activity with BSA: white squares; XET activity without BSA: black squares; MXE activity with BSA: white triangles; MXE activity without BSA: black triangles; CXE activity with BSA: white circles; CXE activity without BSA: black circles. X-axis: Incubation time (h); Y-axis: $^3$H radioactivity incorporated (cpm/kBq of substrate supplied).

Figure 10:
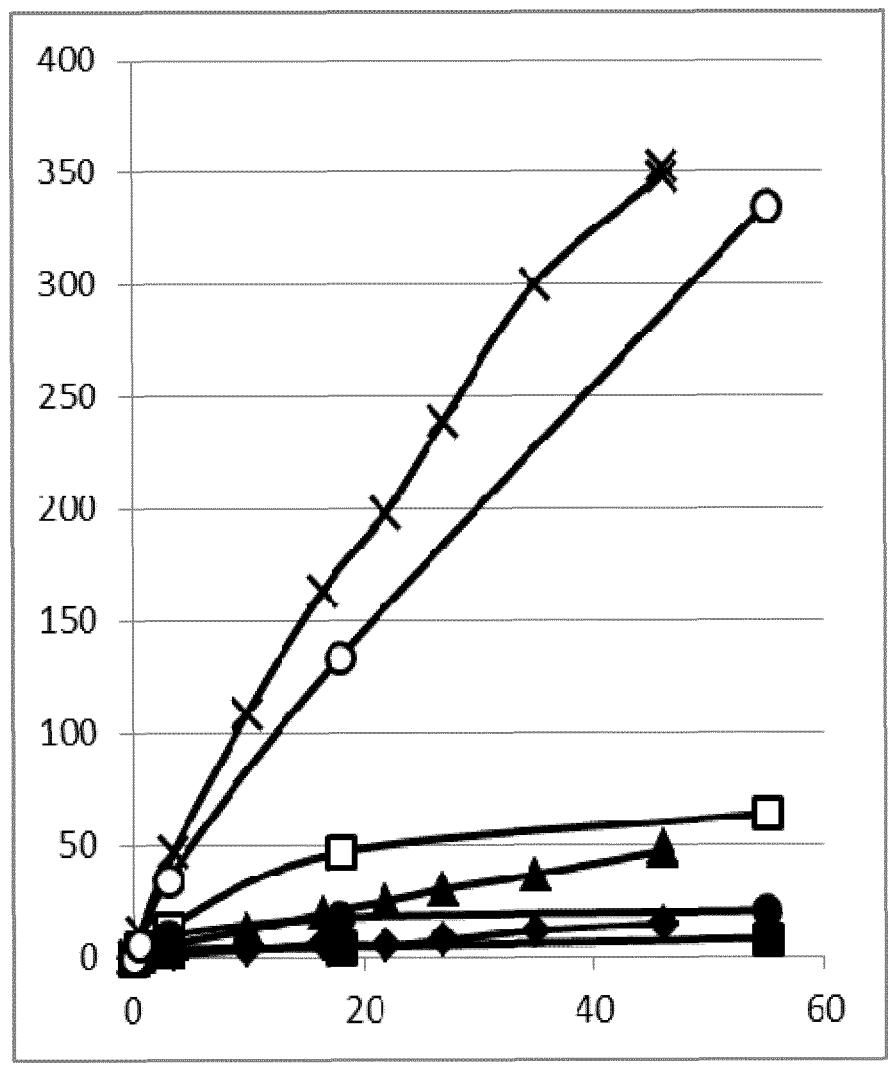

FIG. 10: HTG-catalysed transglycosylations with [$^3$H] XXXGol as acceptor-substrate and various donor-substrates, including: mixed-linkage glucan (MLG) (crosses); xyloglucan (triangles) water-soluble cellulose acetate (WSCA) (diamonds); plain paper (PP) (black squares); alkali-pretreated paper (AP) (black circles); alkali-pretreated paper+bovine serum albumin (AP+BSA) (white circles), plain paper+ bovine serum albumin (PP+BSA) (white squares). X-axis: Incubation time (h); Y-axis: $^3$H radioactivity incorporated (Bq/kBq supplied).

Figure 11:
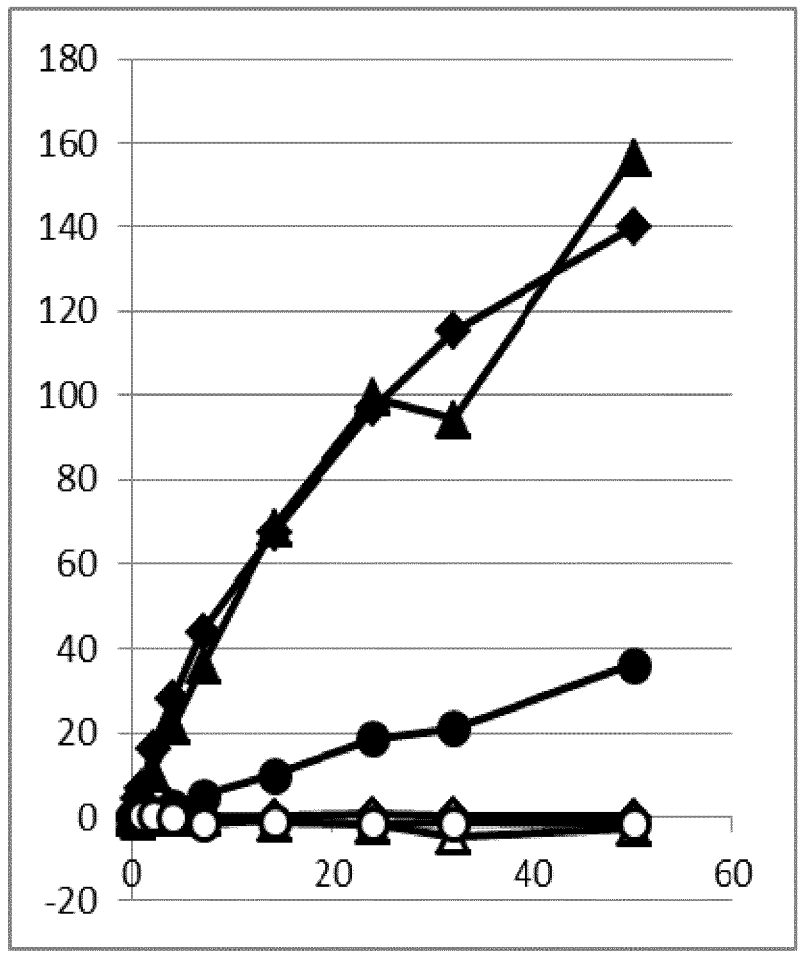

FIG. 11: Transglycosylation with [$^3$H]XXXGol (black symbols) or [$^3$H]cellotetraitol (GGGGol) (white symbols) as acceptors, and with various donor substrates, including alkali-pretreated paper+BSA (AP+BSA) (diamonds; black diamonds with XXXGol, white diamonds with GGGGol), mixed-linkage glucan (MLG) (triangles; black triangles with XXXGol, white triangles with GGGGol) and xyloglucan (circles; black circles with XXXGol, white circles with GGGGol). X-axis: Incubation time (h); Y-axis: $^3$H radioactivity incorporated (Bq/kBq supplied).

Figure 12:
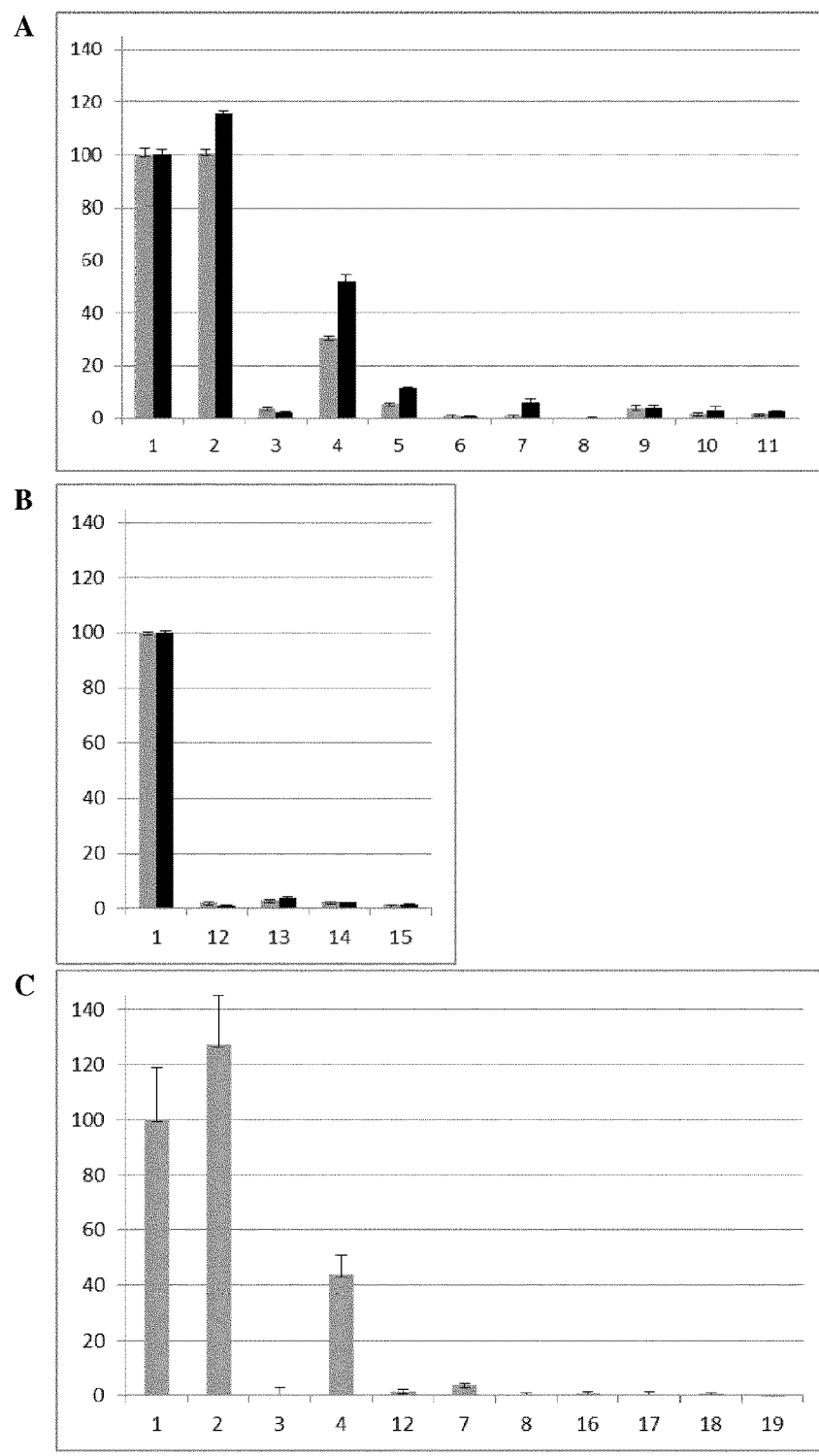

FIG. 12: HTG-catalysed transglycosylation rates with MLG (gray bars) or xyloglucan (black bars) as donor-substrate and various $^3$H-oligosaccharides as potential acceptors. The reaction rate with XXXGol is set at 100%. A, B, and C represent three independent experiments. Experiments B and C utilised affinity-column-purified HTG. In Experiment C, only MLG was used as donor. 1: XXXGol; 2: GXXGol; 3: GGXXXGol; 4: XXLGol; 5: XLLGol; 6: Cell4-ol; 7: Man6-ol; 8: Xyl6-ol; 9: MLGO-ol A; 10: MLGO-ol B; 11: MLGO-ol C; 12: Cell6-ol; 13: MLGO-ol D; 14: MLGO-ol E; 15: MLGO-ol F; 16: Lam4-ol; 17: Gal6-ol; 18: GalA6-ol; 19: MLGO-ols A-F were not individually identified, but are hepta- to decasaccharides from barley-MLG digested with lichenase (A-C) or cellulose (D-F).

Throughout the present application, reference is made to the following sequences:
SEQ ID NO: 1: nucleotide sequence of *Equisetum fluviatile* HTG
SEQ ID NO: 2: amino acid sequence of protein encoded by SEQ ID NO: 1
SEQ ID NO: 3: nucleotide sequence of HTG fusion protein used for expression in *Pichia pastoris*
SEQ ID NO: 4: amino acid sequence of protein encoded by SEQ ID NO: 3
SEQ ID NO: 5: nucleotide sequence of *Equisetum hyemale* HTG
SEQ ID NO: 6: amino acid sequence of protein encoded by SEQ ID NO: 5
SEQ ID NO: 7: nucleotide sequence of *Equisetum diffusum* HTG
SEQ ID NO: 8: amino acid sequence of protein encoded by SEQ ID NO: 7

The examples illustrate the invention

EXAMPLE 1: MATERIALS AND METHODS 1.1 General

Unless stated otherwise, the cloning steps carried out, such as, for example, restriction cleavages, agarose gel electrophoresis, purification of DNA fragments, linking DNA fragments, transformation of bacterial or yeast cells, growing bacteria or yeast and sequence analysis of recombinant DNA, are carried out as described by Sambrook (2000). The sequencing of recombinant DNA molecules is carried out using ABI laser fluorescence DNA sequencer following the method of Sanger.

1.2 Extraction of Enzymes from Plant Material

Crude enzyme mixtures were extracted from fresh plant tissue in CaCl$_2$ (10 mM), succinic acid (0.3 M) and ascorbic acid (20 mM), made fresh to pH 5.5. Polyclar AT (3% w/v) was added to complex with phenolics. Fresh tissue was homogenized in a food blender with 5 ml of the extractant above per gram of fresh weight tissue. The tissue and extractant were stirred on ice for 2.5 h. The extract was filtered through two layers of Miracloth and centrifuged in a Sorvall Evolution RC Centrifuge (10 min, 10,000 rpm, 4° C.). The supernatant was collected and aliquotted, then frozen in liquid nitrogen and stored at −80° C.

1.3 Rotofor Isoelectric Focusing (IEF)

A Bio-Rad Rotofor Cell was assembled and prepared according to the manufacturer's manual. The Rotofor was powered by a BioRad PowerPac HV. Ampholytes were mixed with water and either a marker mixture containing phycocyanin, hemoglobins A and C, and cytochrome c, or a dialysed protein sample. The separation was conducted at 10 W constant power until the voltage stabilized, and fractions were collected according to the manufacturer's methods. A Sartorius PB-11 pH meter was used to measure the pH of the fractions. Transglucosylase activity was also assayed.

1.4 Fluorescent Transglucosylation Assay

Preparation of the Assay Papers

Dot-blot, or test, papers were made following Fry 1997. Test papers were made with Whatman 1CHR chromatography paper. XET-test paper was made by dipping through 1.0% XyG, drying, then dipping through 5 μM XXXG-SR (a conjugate of XXXG and sulphorhodamine (SR)) in 75% acetone or 75% ethanol. Another paper was dipped through 1.0% MLG, dried, then XXXG-SR to make MXE-test paper. Control paper was made, containing no polysaccharide donor substrate other than the paper itself, including the acceptor substrate. The final acceptor substrate concentration for all test papers was ~125 pmol/cm$^2$.

Test Paper Assay

Test papers, cut to size, were used in two ways: either enzyme solutions were applied to the papers as small dots (dot blot assay), or the papers were applied in close contact with native PAGE-gels (zymogram assay). The assay was incubated in a humid environment between two sealed glass plates. The papers were then dried at room temperature and washed in ethanol:FA:water (EFW) 1:1:1 for one hour. The strips were dried, pressed under weight overnight, and photographed using a UVP Multi Doc-It Digital Imaging System. Positive transglucosylation was evident as fluorescence when excited under ultraviolet light at 254 nm.

Fluorescent Dot-Blot Assay

Apply 3-μl aliquots of active enzyme solution [typically in succinate buffer, pH 5.5, containing 10 mM CaCl$_2$] as spots (9 mm centre-to-centre spacing, i.e., in 96-well plate format) to the dry test-paper.

Quickly sandwich the paper between 2 sheets of polythene or glass, press flat with a weight (telephone directory) and incubate at room temperature for 1-24 h. The spots of enzyme should remain moist. To achieve this it is helpful to place spots of enzyme solution (or buffer blanks) over the whole area of the paper, without leaving margins.

Allow to dry in open air, then wash in a polythene sandwich box containing
 either ethanol:90% formic acid:water (EFW) 1:1:1
 or 10% aq formic acid water
with gentle rocking for one hour.

If there is any question that XET or MXE products may also have been formed (though no appropriate donor substrates for these activities had been deliberately added), it might be helpful to wash the paper in 6 M NaOH (with very gentle rocking, as the paper than becomes fragile)

Thoroughly rinse in tap-water.

Dry.

View under UV light (254 nm or 310 nm) or green laser light, and record orange fluorescent spots of CXE reaction product.

1.5 Cellulose:Xyloglucan Endotransglucosylase (CXE) Assays

Whatman 1CHR chromatography paper (10-35 mg; pretreated*) was incubated with an enzyme extract or fraction, [$^3$H]XXXGol (2 kBq), and citrate buffer (pH 6.3, final volume 100 µl) for a designated time, typically 0-24 hours. The reaction was stopped by the addition of 90% formic acid (30 µl), then the paper was washed by repeated additions of water, centrifugation, and removal of the supernatant, until the supernatant no longer contained radioactivity. The cellulose usually required about six washes to become free of soluble radioactivity. The remaining cellulose was suspended in 0.5 ml of water, transferred to a scintillation vial with 5 ml of water-miscible scintillant, and assayed for radioactivity by scintillation counting.

*Pre-Treatment of Paper:

---

Add 3 g paper to 45 ml 6M NaOH, incubate at 37° C. overnight with gentle agitation, wash in water until almost neutral, then with succinate buffer (pH 5.5), then with more water; finally, dry the paper.

---

1.6 Native PAGE

Native polyacrylamide gels were made similar to SDS PAGE, but with a few differences. The stacking gel was made to 4.3% acrylamide with tris(hydroxymethyl)aminomethane (Tris) (67 mM, pH 6.7 with $H_3PO_4$). The resolving gel concentration was 7.5% acrylamide with Tris (376 mM, pH 8.9). Running buffer contained Tris (5 mM) and glycine (38 mM). Gels were electrophoresed at 6° C. for 25 min at 20 mA, then 3 h at 40 mA.

1.7 Dissolution of Cellulose in DMA/LiCl

This procedure was modified from Gurjanov et al. (2008). Molecular sieve (4 Å) was activated (100° C., 3 h). Dimethylacetamide (DMA) was dried over the sieve for at least 5 d. LiCl (8 g) was dried (180° C., 4 h), and dissolved in dry DMA (100 ml). Pieces of Whatman 1CHR were hydrated in water for 1 h, then filtered on nylon mesh. The paper pieces were washed in acetone, then incubated in acetone for 1 h. The pieces were again filtered out using nylon mesh, and washed in DMA, and incubated overnight in dry DMA. The DMA was removed and replaced with 8% LiCl in DMA, so that the paper was 1% (w/v). The paper was dissolved by stirring at room temperature. An equal volume of dry DMA was added to reduce the viscosity of the cellulose solution. The solution was slowly added by a peristaltic pump to rapidly stirring 6 M NaOH, where the cellulose precipitated, but hemicelluloses from the paper were expected to remain in solution.

EXAMPLE 2: CELLULOSE AS A DONOR SUBSTRATE FOR MXE

During a search for enzymes with transglucosylase, in particular MXE (MLG:xyloglucan endotransglucosylase) and XET (xyloglucan endotransglucosylase) activity, enzymes from *Equisetum fluviatile* which were partially purified using ammonium sulphate precipitation and isoelectric focusing (Rotofor) were shown to exert MXE activity and/or XET activity. In a negative control on a paper strip treated with XXXG-SR (a sulphorhodamine conjugate of XXXG (heptasaccharide of xyloglucan)) but with no added polysaccharide donor substrate no residual fluorescence indicating enzymatic activity was expected (FIG. 1). However, a band of apparent transglucosylase activity was mirrored on all three XET (xyloglucan endotransglucosylase), MXE, and control test papers. As cellulose was the only known polysaccharide present in the controls, the possibility of β-(1→4)-glucan to act as a donor substrate in a transglucosylation reaction was investigated.

Test Papers Impregnated with XXXG-SR

First, the apparent transglucosylation product formation with no (other than paper) donor substrate observation was repeated in a slightly different experiment. Partially purified enzyme, rich in MXE and XET activity, was applied as a dilution series to three test papers, impregnated with MLG (mixed-linkage 1,3;1,4-β-D-glucan), XyG (xyloglucan), or no added polysaccharide and XXXG-SR. The papers were maintained in a humid environment for 1 h, then washed free of XXXG-SR, and photographed under UV light to show fluorescent transglucosylation product (FIG. 2a). The three papers were then incubated in 6 M NaOH to remove hemicelluloses from the paper and photographed again (FIG. 2 b).

The initial observation that paper alone, with no added donor substrate, can be a substrate for a transglucosylation was indeed replicated here. The three test papers all show transglucosylation product, as seen by the fluorescent spots, even when the enzyme is diluted 16-fold in buffer. Hemicelluloses, including MXE and XET products, would have been washed out in 6 M NaOH. As expected, the MXE and XET test strips have significantly less product, possibly none, remaining on the paper. The control paper retains product after the NaOH wash, although less remains. Cellulose and some mannans do not dissolve in aqueous NaOH (Moreira and Filho, 2008), and were likely candidates for the donor substrate.

Whatman 1CHR chromatography paper was used. It is made from cotton, but no information about the treatment of the material in the process of making the paper could be obtained. The most abundant polysaccharide present which could donate the energy required for a transglycosylation reaction was undoubtedly cellulose. Other polysaccharides as donor substrates were excluded after analysis by TFA and Driselase® (a fungal enzyme preparation containing polysaccharide exo- and endo-hydrolases, including cellulase, pectinase, beta-xylanase and beta-mannanase) hydrolysis.

Overall, both TFA and Driselase hydrolysis showed that Whatman 1CHR is composed mostly of glucose, most likely from cellulose. TFA (trifluoroacetic acid) hydrolysis also showed traces of xylose. Similarly, Driselase® digestion produced xylose as the most abundant sugar after glucose and cellobiose. Also, the digestion did not show traces of isoprimeverose, indicating an absence of XyG. Some of the glycoproteins comprising the Driselase® mix autolyse during the incubation, producing traces of glucose and mannose.

Cellulose:Xyloglucan Endotransglucosylase Radioactive Assays

To assay the new transglucosylase activity with cellulose as the donor substrate, tentatively termed 'CXE', the radioactive acceptor [$^3$H]XXXGol (reduced XXXG, Xyl3.Glc3.glucitol) was used.

Natural Cellulose as Donor

To determine whether this activity was relevant to the growth of *Equisetum* plants, plant material was used as a potential donor substrate. First, alcohol-insoluble residue (AIR) of callus culture cells and mature plant stems was prepared. The residue was incubated in 6 M NaOH to remove hemicelluloses, some of which would also be donor substrates. AIR and NaOH-washed residue were tested as potential donor substrates (FIG. 3).

As was shown previously, Whatman paper was able to be a donor substrate for a transglucosylation reaction. Culture cells are rich in XyG but lack MLG (FIG. 1), and were expected to supply the donor substrate for XET. Mature shoots, rich in both MLG and XyG, contained the substrates for MXE, XET, and CXE. Interestingly, though, all samples washed in NaOH incorporated more acceptor substrate than unwashed paper or AIR. If 6 M NaOH removes all hemicelluloses covering the cellulose microfibrils, and if it can reduce the crystallinity of the microfibrils, it is possible that cellulose was a better substrate for the dominant transglucosylase than any other substrate.

Cellulose and CXE Product Solubilization and Reconstitution

It has been proposed that hemicelluloses may be trapped within amorphous regions of cellulose microfibrils (Rose and Bennet 1999). Such 'trapped' hemicelluloses may be more tightly connected to cellulose, remaining bound to microfibrils in warm alkali. One could argue that these hypothetical hemicelluloses were the true donor substrate for the observed transglycosylation with paper.

Another method of confirming that [$^3$H]XXXGol was covalently linked to cellulose was to dissolve the cellulosic product. If cellulose microfibrils were reconstituted in alkali, hemicelluloses would no longer be trapped within a microfibril and would remain soluble.

Cellulose was solubilized using lithium chloride (LiCl) in dimethylacetamide (DMA). A solution of 8% LiCl in DMA dissolved CXE product. The viscous solution was slowly transferred to a large volume of 6 M NaOH, where the cellulose re-precipitated. The solid cellulose was separated from the supernatant, and the radioactive product was monitored in each fraction (Table 1).

TABLE 1

| Reconstitution of CXE product | |
|---|---|
| Soluble in 6M NaOH | Precipitated cellulose |
| 6500 cpm | 14000 cpm |

CXE product (40 mg, produced using gel-permeation chromatography) was soaked in water for 1 h, followed by solvent exchange to acetone. The paper was soaked in acetone for 1 h, then exchanged for DMA freed of H$_2$O (over Sigma molecular sieve 4 Å for 5 d), and rotated for 16 h. The DMA was removed, and the CXE product was incubated in dry DMA (4 ml) with 8% (w/v) LiCl for 16 h. An additional 4 ml of DMA was then added to reduce viscosity. The solution of cellulose was slowly added to stirring 6 M NaOH (80 ml) through a peristaltic pump at the rate of 3.2 ml/h. The resultant mixture was stirred for 48 h. A portion of the mixture was removed and centrifuged. The supernatant was separated from the precipitants; both were neutralized with HOAc and scintillation counted. The cpm of the total supernatant and the total precipitates is reported.

Because much of the $^3$H product precipitated, cellulose might have indeed been the true substrate for the transglucosylation reaction with paper. The majority of $^3$H followed the expected pattern of cellulose precipitation in 6 M NaOH after dissolution in LiCl and DMA. While the measured ratio of tritium in the precipitate to tritium in the supernatant was 2.2:1, this ratio might have been higher still on a Bq basis since solid particles are counted with a lower efficiency than a solution.

The radioactivity that remained in solution might have been breakdown products of XXXGol, or could have been short pieces of β-(1→4)-glucan attached to XXXGol with increased solubility because of the XGO.

In summary, CXE product dissolved by LiCl in DMA precipitated upon reconstitution of the cellulose in 6 M NaOH, indicating that the transglucosylation product was not a hemicellulose.

CXE is an Activity of Partially Purified HTG

It was shown that multiple proteins in ammonium sulphate precipitate fractions of *Equisetum* were capable of transglucosylation, some of them displaying XET activity, and at least one other enzyme, MXE, capable of using either MLG or XyG as a donor substrate. Partially purified fractions of *Equisetum* extract obtained using isoelectric focusing (Rotofor) and containing the two enzyme activities MXE and XET were tested for their ability to use cellulose as a donor substrate (Table 2).

TABLE 2

| CXE activity from partially purified HTG | |
|---|---|
| Enzyme | Product formed (cpm) |
| pp MXE | 1825 |
| pp XET | 18 |
| ASP | 1217 |
| buffer only | 13 |

Partially purified (pp) MXE, pp XET, ASP, or buffer only (0.3 M citrate, pH 6.3) was incubated with [$^3$H]XXXGol (2 kBq), citrate buffer (up to 100 μl), and 10 mg of Whatman 1CHR paper (untreated) for 3.3 h. The reaction was stopped with FA (30 μl), and unused reactant was washed out with water. The paper (in 5 ml water) was incubated in scintillant and assayed for $^3$H.

The partially purified HTG fraction contained high levels of CXE activity, but the fraction with XET activity only did not use cellulose as a donor substrate. While the MXE fraction was not one pure protein, it contained only a few and was highly enriched in one protein. In another experiment, a series of Rotofor-purified fractions containing MXE activity were tested for CXE activity, and patterns of high CXE activity directly correlated with patterns of high MXE and XET activity (FIG. 5). This enzyme may be a relatively indiscriminate transglucosylase, able to use β-(1→4)-glucans irrespective of side-chains or other backbone linkages.

Summary of MXE Activity Using Various Donor and Acceptor Substrates

The partially purified MXE fraction was able to use cellulose, MLG, or XyG as donor substrates with many acceptor substrates (Table 3). While MLG was a better donor substrate than XyG, direct comparison of activity rates with cellulose as a donor substrate was difficult. The concentration of a polysaccharide in solution, such as MLG or XyG, cannot be compared with a similar concentration of a solid in water. In addition, tritium embedded in or on a solid substrate such as cellulose was counted with lower efficiency than tritium in solution, reducing the ability to detect CXE product. Therefore, MXE and XET activity can be directly compared, but only roughly compared with CXE activity.

TABLE 3

Summary of MXE activity using various donor and acceptor substrates

| | Relative reaction rate with the acceptor of: | | | | | |
|---|---|---|---|---|---|---|
| Donor | XXXGol | MLGOs | Cello₆ol | XXLGol | XLLGol | XXFG |
| XyG | +++ | + | + | + | + | |
| MLG | ++++ | + | + | ++ | + | + |
| Cellulose | ++ | | | | | |
| Lichenan | ± | | | | | |
| Laminarin | – | | | | | |
| Mannan | – | | | | | |
| GM | ± | | | | | |

(abbreviations: GM = glucomannan, XyG = xyloglucan, MLGO = mixed-linkage glucan oligosaccharide, Cello₆ol = cellohexaitol, XXFG = nonasaccharide of xyloglucan having composition Gucose4·Xylose3·Galactose1·Fucose1)

CXE Activity

A multitude of observations lead to the confirmation of cellulose:xyloglucan endotransglucosylase activity.

If the same xyloglucan molecule can be attached to two neighbouring cellulose microfibrils, the microfibrils themselves could become covalently attached through the XyG intermediate (FIG. 4). A covalently linked cellulose network could be stronger than a hydrogen bonded network.

EXAMPLE 3: TRACKING AND SEQUENCING OF GENES ENCODING HTG PROTEINS WITH CXE ACTIVITY

RNA was prepared from a mature shoot of an *E. fluviatile* individual using Trizol reagent (Invitrogen). cDNA was prepared with an Evrogen Mint-Universal cDNA synthesis kit, normalized with an Evrogen Trimmer kit and sequenced using 454 sequencing technology. Raw data were assembled into contigs and isotigs using Roche proprietary Newbler assembler version 2.5.

In order to identify the protein(s) having CXE activity in *Equisetum*, the following approach was followed:

HTG was purified from a crude *E. fluviatile* extract by four sequential techniques: differential ammonium sulphate precipitation, gel-permeation chromatography, lectin affinity-chromatography and isoelectric focusing. The resultant sample was separated by SDS PAGE from which a single predominant ~30 kDa band was cut. The sample was digested with trypsin and analysed by MALDI-ToF and LC-MS.

To identify target genes, the *Equisetum* transcriptome was translated and the inferred proteins were subjected to in silico trypsin digestion. From the ~30 kDa fraction prepared from the partially purified IEF fraction, two isotigs which had the highest scoring were partial gene sequences of XTH homologous proteins. The full length sequence of the two candidate genes was identified by the use of 5' and 3' RACE results showed that these were two parts of the same full-length gene. The protein had a predicted pI of 4.66 and a predicted mass of 29.5 kDa. The coding sequence is shown in SEQ ID NO: 1, and the sequence of the encoded protein in SEQ ID NO: 2. It is predicted that amino acids 1-21 of SEQ ID NO: 2 correspond to the signal peptide, and that amino acids 22-280 correspond to the mature protein, and thus that nts 1-63 of SEQ ID NO: 1 encode the signal peptide, and that nts 64-840 encode the mature protein.

The sequences of SEQ ID NOs 1 and 2 were used to blast a publically available sequence database. Two homologous genes were found, one from *Equisetum hyemale* (SEQ ID NO: 5 for the coding sequence, having 83% sequence identity to the nucleotide sequence of SEQ ID NO: 1, and SEQ ID NO: 6 for the encoded protein having 75% sequence identity to the amino acid sequence of SEQ ID NO: 2), and one from *Equisetum diffusum* (SEQ ID NO: 7 for the coding sequence, having 94% sequence identity to the nucleotide sequence of SEQ ID NO: 1, and SEQ ID NO: 8 for the encoded protein having 91% sequence identity to the amino acid sequence of SEQ ID NO: 2). An alignment of the nucleotide sequences and of the amino acid sequences of the *Equisetum* HTG proteins is shown in FIG. 8. It is predicted that amino acids 1 to 25 of SEQ ID NO: 6 correspond to the signal peptide, and amino acids 26 to 283 to the mature protein, and that amino acids 1 to 28 of SEQ ID NO: 8 correspond to the signal peptide, and amino acids 29 to 287 to the mature protein. Thus, nt 1-75 of SEQ ID NO: 5 encode the signal peptide, and nt 76-849 of SEQ ID NO: 5 encode the mature protein, and nt 1-84 of SEQ ID NO: 7 encode the signal peptide and nt 85-861 of SEQ ID NO: 7 encode the mature protein. The predicted mature protein, i.e. amino acids 26 to 283, of SEQ ID NO: 6 have 79% sequence identity to the predicted mature protein, i.e. amino acids 22-280, of SEQ ID NO: 2, whereas the predicted mature protein, i.e. amino acids 29 to 287, of SEQ ID NO: 8 have 94% sequence identity to the mature protein, i.e. amino acids 22-280, of SEQ ID NO: 2.

EXAMPLE 4: MXE, XET AND CXE ACTIVITY OF RECOMBINANT HTG EXPRESSED IN *PICHIA*

The mature HTG protein of *Equisetum fluviatile* (amino acids 22 to 280 of SEQ ID NO: 2) was expressed from the pPICZαA vector following insertion, by transformation into *Pichia pastoris* (SMD1168H) as fusion protein with an α-factor signal sequence at the N-terminus and a c-myc epitope and polyhistidine tag at the C-terminus. The coding sequence of the expressed fusion protein is shown in SEQ ID NO: 3, and the encoded protein in SEQ ID NO: 4. Of SEQ ID NO: 4, amino acids 1-89 correspond to the α-factor signal sequence, amino acids 92-350 correspond to the mature HTG protein, amino acids 353-362 to the c-myc epitope, and amino acids 368-373 to the polyhistidine tag.

Transformed *Pichia* cells expressing the HTG fusion protein were grown in liquid growth medium (90% (v/v) low salt LB, 1% (w/v) glycerol, 0.00004% (w/v) biotin, 100 μg ml$^{-1}$ zeocin). Expression was stimulated by centrifugation and resuspension of the culture in expression medium (identical to growth medium but with glycerol replaced with 10% (v/v) methanol). After 24 h the culture medium was harvested and assayed for endotransglucosylase activies.

XET and MXE Assay

XET activity was assayed using a reaction mixture consisting 10 μl *Pichia*-secreted enzyme extract, 1 kBq [3H] XXXGol (dried to give zero volume) and 10 μl 1% donor xyloglucan (XyG) polysaccharide. Donor, enzyme and acceptor components were in 50 mM MES buffer, pH 6.0. The reaction mixture was incubated for 16 hour at room temperature. The reaction was stopped by addition of 50 μl of 50% (w/v) formic acid. Each sample was loaded onto Whatman 3 MM filter paper, dried and then washed thoroughly with free-flowing water to remove unreacted [3H] XXXGol. Time taken for removal of excess [3H]XXXGol was determined by assaying a blank square of paper, washed in the same conditions as those containing the acceptor oligosaccharide, producing levels of radioactivity equivalent to background.

Each paper square was air-dried, incubated with scintillant (2 ml) and assayed for radioactivity twice for 5 minutes. Enzyme controls involved the addition of formic acid prior to the addition of enzyme to produce an environment in which it is unable to function.

The MXE activity assay differs from the XET assay by the use of 1% MLG as the donor polysaccharide instead of XyG.

CXE Assay

To 1 kBq dried [3H]XXXGol, 33 µl enzyme extract (in 50 mM MES; pH 6.0) was mixed thoroughly and added to 10 mg of pre-treated dry Whatman 1CHR paper and incubated at room temperature for up to 24 hours. The reaction was stopped by the addition of 300 µl 10% (w/v) formic acid before repeated washing for 8-16 hours to remove unreacted [3H]XXXGol. Following the final washing and removal of excess water, cellulose was collected in 400 µl water+4 ml water-miscible scintillant and transferred to a scintillation vial prior to assaying for radioactivity.

Results

XET, MXE and CXE activities of 10 µl of the recombinantly-expressed protein solution after incubation of 1 hour and 3 hours are shown in Table 4.

Substrate mixture comprised (final concentrations):
[3H]XXXGol 50 kBq/ml (specific activity 900 MBq/µmol)
23 mM citrate (Na$^+$), pH 6.3
32.4% (v/v) spent medium from HTG-expressing *Pichia* line.
0 or 0.11% w/v BSA
and a donor substrate polysaccharide as detailed below.

For the CXE assay, 20 µl (=1.00 kBq) of the mixture (with no added polysaccharide) was applied to a dried paper (mean dry weight of paper=18.6 mg), the vial was capped tightly, and incubation was conducted at 20° C. At desired time-points, the reaction was stopped by addition of formic acid to 20% v/v. The paper pieces were then washed in running tap-water, dried, and assayed for incorporated radioactivity by scintillation counting.

For the MXE or XET assays, 20 µl (=1.00 kBq) of the reaction mixture, supplemented with 0.5% (w/v; final concentration) barley mixed-linkage β-glucan or tamarind xyloglucan respectively, was incubated as free solution at 20° C. At intervals the reaction was stopped by addition of NaOH to 0.1 M. The mixtures were later slightly acidified with

TABLE 4

XET (Tamarind xyloglucan (Tx) used as donor), MXE (MLG used as donor) and CXE (cellulose used as donor) activity of recombinantly expressed HTG protein

| Activity | Inc time | Acceptor | Enzyme | Donor | cpm (i) | cpm (ii) | cpm (av) |
|---|---|---|---|---|---|---|---|
| Control | 1 h | Blank | Blank | Blank | 12.60 | 11.00 | 11.80 |
| XET | 1 h | [³H]XXXGol | HTG *Pichia* | Tx | 1592.00 | 1594.60 | 1593.30 |
| MXE | 1 h | [³H]XXXGol | HTG *Pichia* | MLG | 2143.01 | 2097.21 | 2120.11 |
| Control | 1 h | [³H]XXXGol | HTG *Pichia* | Control | 20.40 | 25.60 | 23.00 |
| Control | 3 h | Blank | Blank | Blank | 12.60 | 11.00 | 11.80 |
| XET | 3 h | [³H]XXXGol | HTG *Pichia* | Tx | 2267.63 | 2256.43 | 2262.03 |
| MXE | 3 h | [³H]XXXGol | HTG *Pichia* | MLG | 3141.65 | 3100.45 | 3121.05 |
| Control | 3 h | [³H]XXXGol | HTG *Pichia* | Control | 14.00 | 14.00 | 14.00 |
| Control | 1 h | Blank | Blank | Blank | 3.51 | 2.91 | 3.21 |
| CXE | 1 h | [³H]XXXGol | HTG *Pichia* | Cellulose | 226.85 | 233.70 | 230.27 |
| Control | 3 h | Blank | Blank | Blank | 3.51 | 2.91 | 3.21 |
| CXE | 3 h | [³H]XXXGol | HTG *Pichia* | Cellulose | 549.28 | 559.70 | 554.49 |

To determine the initial rates of MXE, XET and CXE activity of the HTG protein expressed in *Pichia*, MXE, XET and CXE assays were performed during 16 hours and activity was measured at several time points.

The results of the timescale in shown in FIG. 6. Initial rates were determined from the timescale and are shown in Table 5.

TABLE 5

Initial rates of the XET, MXE and CXE activities of the HTG protein expressed in *Pichia*

| XET | 43 cpm/min |
| MXE | 112 cpm/min |
| CXE | 11.7 cpm/min |

Tables 4 and 5, and FIG. 6 show that the recombinantly expressed *Equisetum* HTG protein has MXE and XET activity, as well as a significant CXE activity.

The CXE, MXE and XET activities of the HTG protein expressed in *Pichia* were also tested in the presence of BSA in the reaction mixture.

Briefly, Whatman No. 1 paper pieces (each 2.0×1.15 cm), were pre-treated with 6 M NaOH (containing 1% w/v NaBH$_4$) at room temp overnight, then washed in running tap-water, followed by 1% acetic acid and de-ionised water, and finally dried.

acetic acid, and dried onto Whatman No. 3 filter paper; the paper was then washed overnight in running tap-water, dried, and assayed for radioactivity by scintillation counting.

Time-course graphs are shown in FIG. 9, and reaction rates are shown in Table 6 (calculated as cpm $^3$H incorporated into polysaccharide, per kBq of acceptor substrate supplied, per hour of incubation).

BSA strongly promoted the CXE reaction, probably by preventing the HTG protein binding irreversibly to the paper surface; BSA had relatively little effect on the MXE and XET rates.

According to the +BSA data, the rates are in the ratio MXE:CXE:XET=100:38.4:38.2.

According to the −BSA data, the rates are in the ratio MXE:CXE:XET=100:2.3:39.1.

Thus, the HTG is a highly CXE-active enzyme.

TABLE 6

Mean reaction rates for the three enzyme activities of *Pichia*-expressed HTG under conditions made as directly comparable as feasible

| parameter | CXE −BSA | CXE +BSA | MXE −BSA | MXE +BSA | XET −BSA | XET +BSA |
|---|---|---|---|---|---|---|
| mean rate (cpm/kBq/h) | 0.88 | 17.20 | 38.65 | 44.85 | 15.11 | 17.14 |
| rate relative (%) to MXE + BSA | 1.96 | 38.36 | 86.17 | 100.00 | 33.69 | 38.21 |

TABLE 6-continued

Mean reaction rates for the three enzyme activities of *Pichia*-expressed HTG under conditions made as directly comparable as feasible

| parameter | CXE −BSA | CXE +BSA | MXE −BSA | MXE +BSA | XET −BSA | XET +BSA |
|---|---|---|---|---|---|---|
| rate relative (%) to MXE − BSA | 2.27 | 44.51 | 100.00 | 116.05 | 39.10 | 44.35 |

Acceptor Substrate Specificity of the Recombinant HTG

Acceptor substrate specificity of the recombinant HTG was tested in assays (in absence of BSA) using barley mixed-linkage glucan (BMLG) as donor. The enzyme used was recombinant HTG enzyme which was affinity-purified using the his-tag. All data points are the corrected means of three independent reactions.

For acceptor substrates showing relatively low affinity for paper, the conventional paper washing method was employed (running tap-water, overnight). For those acceptors exhibiting high affinity for paper (namely cellohexaitol, mannohexaitol, xylohexaitol, and the MLG oligosaccharides), a glass fibre method was employed in which the reaction products were dried onto pre-baked Whatman GF/A glass fibre paper and then washed in 75% ethanol.

The results are shown in FIG. 7. The only acceptor substrates that recombinant HTG was able to incorporate to any significant degree were xyloglucan oligosaccharides. In a further experiment, acceptor substrate specificity was determined for mixed-linkage glucan and xyloglucan as donor. The results are shown in FIG. 12. It was observed that non-galactosylated XGOs were preferred. The fact that the HTG protein used GXXGol equally well or better than XXXGol distinguishes it from conventional XETs which require xylosylation at subsite position+1; in stark contrast, HTG appears to prefer un-xylosylated Glc residues there. However, despite this preference for non-xylosylation at +1, the complete inability to utilise GGXXXGol indicates that xylosylation at +2 is a necessity for the HTG protein's activity. This requirement for xylosylation at +2 is consistent with the inability of the protein to utilise related non-xylosylated oligosaccharides such as cellohexaitol and the various MLG oligosaccharides.

Given that donor substrate specificity results indicate the HTG protein favours MLG as a donor substrate over xyloglucan, these results confirm that it is a predominant heterotransglucanase. While it is able to catalyse XET activity (xyloglucan-to-xyloglucan; FIG. 6), it appears completely unable to catalyse MLG-MLG endotransglycosylation at all, as shown in FIG. 7 by the inability to utilise MLG oligosaccharides.

It is likely that the HTG protein has similar acceptor substrate specificity when cellulose is used as donor.

This makes HTG the first plant enzyme whose preferred reaction is hetero-endotransglycosylation, and the first endotranglycosylase that favours MLG as a substrate.

Acceptor substrate specificity was also tested for the different donor substrates alkali-treated paper, mixed-linkage glucan, and xyloglucan. It was observed that XXXGol was a strong acceptor with alkali-treated paper and with mixed-linkage glucan as donor, but that the transglycosylation with GGGGol was much less efficient (see FIG. 11).

Substrate Specificity of the Recombinant HTG for Different Cellulosic Substrates HTG-catalysed transglycosylation with [3H]XXXGol as acceptor-substrate and various donor-substrates was tested in presence and absence of BSA, and with mixed-linkage glucan as control (see FIG. 10). It was observed that, under optimized conditions, the HTG had an XET:MXE activity ratio of ~1:7. It was also observed that water-soluble cellulose acetate was only a weak donor, but that HTG had remarkable CXE activity on (insoluble) cellulose. Over 94% of a radioactive CXE product resisted solubilisation in 6M NaOH at 37° C. (data not shown), indicating firm integration within the fibres. BSA strongly promoted the CXE reaction on alkali-treated paper and on plain paper.

Affinity of the Recombinant HTG for XXXGol

The affinity of recombinant HTG for XXXGol was determined by determining the reaction rate (fmol/h) with mixed-linkage glucan and xyloglucan as donor, at different concentrations of XXXGol. It was found that the $K_M$ for XXXGol with mixed-linkage glucan as donor-substrate was 0.52±0.06 μM, and the $K_M$ for XXXGol with xyloglucan as donor-substrate was 3.4±0.4 μM. This shows that HTG has a much higher affinity for XXXGol than do XTHs ($K_M$~50-200 μM).

The affinity of recombinant HTG for soluble donor-polysaccharides was determined by measuring the $^3H$ incorporation rate at different concentrations polysaccharides. The results are shown in Table 7.

TABLE 7

Vmax and Km values of recombinant HTG for different soluble donor polysaccharides

| Donor polysaccharide | Vmax (Bq/kBq/h) | $K_M$ (mg/ml) |
|---|---|---|
| xyloglucan | 0.626 ± 0.057 | 0.226 ± 0.077 |
| barley-mixed-linkage glucan | 7.59 ± 0.60 | 1.25 ± 0.32 |
| water-soluble cellulose acetate | 0.29 ± 0.03 | 1.65 ± 0.60 |
| Iceland-moss mixed-linkage glucan | 0.098 ± 0.014 | 3.05 ± 1.15 |

Table 7 shows that HTG has a lower affinity for barley-MLG than for xyloglucan. Iceland-moss MLG, largely comprising cellotriosyl repeat-units, was a poor donor-substrate. Thus HTG probably recognises cellotetraosyl repeat-units, which occur in barley-MLG and predominate in *Equisetum*-MLG.

EXAMPLE 5: TRANSFORMATION OF PLANTS WITH HTG

A T-DNA vector is constructed encoding a fusion protein of the 27 amino acids signal sequence of the alpha-amylase 3 gene from rice (Sutcliff et al., 1991, Plant Mol Biol 16:579) and amino acids 22 to 280 of SEQ ID NO: 2 under control of the Cauliflower Mosaic Virus 35S promoter.

Wheat plants are transformed with the T-DNA vector encoding the HTG fusion protein. It is observed that the transformed wheat plants have increased stem strength, resulting in an improved stem lodging resistance, and an increased pathogen resistance.

REFERENCES

Abdel-Massih R M, Baydoun E A, Brett C T (2003). In vitro biosynthesis of 1,4-beta-galactan attached to a pectin-xyloglucan complex in pea. Planta 216(3), 275-286.

Ait-Mohand F, Farkaš V (2006) Screening for hetero-transglycosylating activities in extracts from nasturtium (*Tropaeolum majus*). Carbohydrate Research 341: 577-581.

An Y Q, Huang S, McDowell J M, McKinney E C, Meagher R B (1996). Conserved expression of the *Arabidopsis*

ACT1 and ACT 3 actin subclass in organ primordia and mature pollen. *Plant Cell* 8: 15-30.

Bacic, A., Harris, P. J., and Stone, B. A. (1988) in *The Biochemistry of Plants* (Priess J., ed) pp. 297-371, Academic Press, New York.

Barry, G., Kishore, G., Padgette, S. et al. Inhibitors of amino acid biosynthesis: strategies for imparting glyphosate tolerance to crop plants. Curr Topics Plant Physiol 7:139-145 (1992).

Baumann M J, Eklöf J M, Michel G, Kallas A M, Teeri T T, Czjzek M, Brumer H 3rd. (2007). Structural evidence for the evolution of xyloglucanase activity from xyloglucan endo-transglycosylases: biological implications for cell wall metabolism. Plant Cell. 2007 June; 19(6):1947-63.

Benfey P N, Ren L, Chua N H. (1989). The CaMV 35S enhancer contains at least two domains which can confer different developmental and tissue-specific expression patterns. *EMBO J.* 8:2195-2202.

Chabouté et al., 1987. Polyadenylation of histone H3 and H4 mRNAs in dicotyledonous plants. *Gene, Volume* 71, *Issue* 1, 15, pp 217-223.

Cocuron, J. C., Lerouxel, O., Drakakaki, G., Alonso, A. P., Liepman, A. H., Keegstra, K., Raikhel, N. and Wilkerson, C. G. (2007) A gene from the cellulose synthase-like C family encodes a b-1,4 glucan synthase. Proc. Natl. Acad. Sci. USA, 104, 8550-8555.

Comai L, Sen L C, Stalker D M. (1983). An Altered aroA Gene Product Confers Resistance to the Herbicide Glyphosate. Science 221, 370-371.

Cornelissen B J, Hooft van Huijsduijnen R A, Van Loon L C, Bol J F. (1986). Molecular characterization of messenger RNAs for 'pathogenesis related' proteins Ia, Ib and Ic, induced by TMV infection of tobacco. EMBO J 5:37-40.

Cornelissen M. and Vandewiele M. (1989). Nucleic Acids Research, 17, 19-25.

Cregg J M, Vedvick T S, Raschke W C (1993). Recent advances in the expression of foreign genes in *Pichia pastoris*. Biotechnology (N Y) 11(8):905-10.

Crickmore N, Zeigler D R, Feitelson J, Schnepf E, Van Rie J, Lereclus D, Baum J, Dean D H (1998) Revision of the nomenclature for the *Bacillus thuringiensis* pesticidal crystal proteins. Microbiology and Molecular Biology Reviews, 62: 807-813.

Cumming C M, Rizkallah H D, McKendrick K A, Abdel-Massih R M, Baydoun E A, Brett C T. (2005). Biosynthesis and cell-wall deposition of a pectin-xyloglucan complex in pea. *Planta* 222, 546-555.

Datla R, Anderson J W, Selvaraj G (1997). Plant promoters for transgene expression. Biotechnology Ann. Rev. 3, 269-296.

Faik A, Price N J, Raikhel N V, Keegstra K. (2002). An *Arabidopsis* gene encoding an alpha-xylosyltransferase involved in xyloglucan biosynthesis. PNAS 99(11): 7797-7802.

Franková L and Fry S C (2013) Darwin Review: Biochemistry and physiological roles of enzymes that 'cut and paste' plant cell-wall polysaccharides. J Exp Bot 64: 3519-3550.

Fry S C, Smith R C, Renwick K F, Martin D J, Hodge S K, Matthews K J (1992) Xyloglucan Endotransglycosylase, A New Wall-Loosening Enzyme-Activity from Plants. Biochemical Journal 282: 821-828.

Fry S C, Mohler K E, Nesselrode B H W A, Frankova L (2008 a) Mixed-linkage beta-glucan:xyloglucan endotransglucosylase, a novel wall-remodelling enzyme from *Equisetum* (horsetails) and charophytic algae. Plant Journal 55: 240-252.

Fry S C, York W S, Albersheim P, Darvill A, Hayashi T, Joseleau J-P, Kato Y, Perez Lorences E, Maclachlan G A, McNeil M, Mort A J, Reid J S G, Seitz H U, Selvendran R R, Voragen A G J, White A R (1993) An unambiguous nomenclature for xyloglucan-derived oligosaccharides. Physiologia Plantarum 89: 1-3.

Gasser, C. S., J. A. Winter, C. M. Hironaka, D. M. Shah (1988). Structure, expression, and evolution of the 5-enolpyruvylshikimate-3-phosphate synthase genes of *petunia* and tomato. J. Biol. Chem. 263: 4280-4289.

Gritch et al (2006). PNAS 103(40), 14701-14706.

Gurjanov O P, Ibragimova N N, Gnezdilov O I, Gorshkova T A (2008) Polysaccharides, tightly bound to cellulose in cell wall of flax bast fibre: Isolation and identification. Carbohydrate Polymers 72: 719-729.

Harpster et al., 1988, Mol Gen Genet. 212(1):182-90.

Holtorf S, Apel K, Bohlmann H. (1995). Comparison of different constitutive and inducible promoters for the overexpression of transgenes in *Arabidopsis thaliana*. Plant Mol. Biol. 29:637-649.

Hou et al., 2008, *Chinese Science Bulletin* 53, pp 2639-2645.

Hrmova, M., Farkaš, V., Lahnstein, J., Fincher, G. B. (2007). A Barley Xyloglucan Xyloglucosyl Transferase Covalently Links Xyloglucan, Cellulosic Substrates, and (1,3; 1,4)-β-D-Glucans. JBC 282 (17); pp. 12951-62.

Keller B, Sauer N, Lamb C J (1988). Glycine-rich cell wall proteins in bean: gene structure and association of the protein with the vascular system. *EMBO J.* 7(12): 3625-3633.

Keller B, Lamb C J. (1989). Specific expression of a novel cell wall hydroxyproline-rich glycoprotein gene in lateral root initiation. *Genes Dev.* 3: 1639-1646.

Lindbo (2007). Plant Physiology 145, 1232-1240.

Logan, Edwards and Saunders (Editors; Real-Time PCR: Current Technology and Applications, Caister Academic Press 2009, ISBN: 978-1-904455-39-4.

Maris A, Kaewthai N, Eklof J M, Miller J G, Brumer H, Fry S C, Verbelen J P, Vissenberg K (2011) Differences in enzymic properties of five recombinant xyloglucan endo-transglucosylase/hydrolase (XTH) proteins of *Arabidopsis thaliana*. Journal of Experimental Botany 62: 261-271.

Moellenbeck D J, Peters M L, Bing J W, Rouse J R, Higgins L S, Sims L, Nevshemal T, Marshall L, Ellis R T, Bystrak P G, Lang B A, Stewart J L, Kouba K, Sondag V, Gustafson V, Nour K, Xu D, Swenson J, Zhang J, Czapla T, Schwab G, Jayne S, Stockhoff B A, Narva K, Schnepf H E, Stelman S J, Poutre C, Koziel M, Duck N. (2001). Insecticidal proteins from *Bacillus thuringiensis* protect corn from corn rootworms. Nat. Biotechnol. 19: 668-72.

Moreira A (2004) Genetic Algorithms for the imitation of genomic styles in protein backtranslation. Theor Comput Sci 332: 297-312.

Moreira L R S, Filho E X F (2008) An overview of mannan structure and mannan-degrading enzyme systems. Applied Microbiology and Biotechnology 79: 165-178.

Needleman and Wunsch (1970). A general method applicable to the search for similarities in the amino acid sequence of two proteins. J. Mol. Biol., 48, p. 443-453.

Odell J T, Nagy F, Chua N H (1985). Identification of DNA sequences required for activity of the cauliflower mosaic virus 35S promoter. Nature. 6; 313(6005):810-2.

Pearson and Lipman (1988). Improved tools for biological sequence comparison. Proc. Natl. Acad. Sci 85, p. 2444-48.

Peleman J, Saito K, Cottyn B, Engler G, Seurinck J, Van Montagu M, Inzé D (1989). Structure and expression analyses of the S-adenosylmethionine synthetase gene family in *Arabidopsis thaliana*. Gene 84: 359-369.

Pu L, Li Q, Fan X, Yang W, Xue Y (2008). The R2R3 MYB transcription factor GhMYB109 is required for cotton fiber development. *Genetics* 180, pp 811-820.

Rose J K C, Bennett A B (1999) Cooperative disassembly of the cellulose-xyloglucan network of plant cell walls: parallels between cell expansion and fruit ripening. Trends in Plant Science 4: 176-183.

Sambrook, J. F., Russell, D. W. and Irwin, N. (2000). Molecular Cloning: A Laboratory Manual, 3rd edition Volumes 1, 2, and 3. Cold Spring Harbor Laboratory Press.

Samac D A, Tesfaye M, Dornbusch M, Saruul P, Temple S J (2004). A comparison of constitutive promoters for expression of transgenes in alfalfa (*Medicago sativa*). Transgenic Res. 13(4):349-61).

Sanger M, Daubert S, Goodman R M (1990). Characteristics of a strong promoter from figwort mosaic virus: comparison with the analogous 35S promoter from cauliflower mosaic virus and the regulated mannopine synthase promoter. Plant Mol Biol. 14(3):433-43).

Schnepf H E, Lee S, Dojillo J, Burmeister P, Fencil K, Morera L, Nygaard L, Narva K E, Wolt J D. (2006). Characterization of Cry34/Cry35 Binary Insecticidal Proteins from Diverse *Bacillus thuringiensis* Strain Collections. Applied Environm. Microbiol. 71, 1765-1774.

Schramm, G, Bruchhaus, I and Roeder, T (2000). A simple and reliable 5'-RACE approach. Nucleic Acids Research 28: e96.

Shah, D M, Horsch, R B, Klee, H J, Kishore, G M, Winter, J A, Tumer, N E, Hironka, C M, Sanders, P R, Gasser, C S, Aykent, S, Siegel, N R, Rogers, S G and Fraley, R T (1986). Engineering Herbicide Tolerance in Transgenic Plants. Science 233, 478-481.

Somerville C, Bauer S, Brininstool G, Facette M, Hamann T, Milne J, Osborne E, Paredez A, Persson S, Raab T, Vorwerk S, Youngs H (2004) Toward a systems approach to understanding plant-cell walls. Science 306: 2206-2211.

Sørensen I, Pettolino F A, Wilson S M, Doblin M S, Johansen B, Bacic A, Willats W G T (2008) Mixed-linkage (1→3), (1→4)-beta-D-glucan is not unique to the poales and is an abundant component of *Equisetum arvense* cell walls. Plant Journal 54: 510-521.

Thompson, J E and Fry, S C (2000). Evidence for covalent linkage between xyloglucan and acidic pectins in suspension-cultured rose cells. Planta 211, 275-286.

Tranel P J, Wright T R (2002) Resistance of weeds to ALS-inhibiting herbicides: what have we learned? Weed Sci 50:700-712.

Wagner et al (2004). Methods 32, 227-234.

Waterman, M. S. (1995). Introduction to Computational Biology: Maps, sequences and genomes. Chapman & Hall. London.

Zanoni I, Ostuni R, Capuano G, Collini M, Caccia M, Ronchi A E, Rocchetti M, Mingozzi F, Foti M, Chirico G, Costa B, Zaza A, Ricciardi-Castagnoli P, Granucci F. (2009). CD14 regulates the dendritic cell life cycle after LPS exposure through NFAT activation. Nature 460, p:264-268, see also Nature Protocols: mRNA expression analysis by Real-Time PCR; ISSN: 1754-2189.

---

The invention claimed is:

1. A chimeric gene comprising the following operably linked elements:
   a. a heterologous promoter;
   b. the nucleic acid selected from the group consisting of:
      i. a nucleic acid sequence encoding a protein having cellulose:xyloglucan endotransglucosylase activity comprising
         1. the amino acid sequence of any one of SEQ ID NOs: 2, 6 and 8; or
         2. an amino acid sequence having at least 95% sequence identity to the sequence of any one of SEQ ID NOs: 2, 6 and 8, or
         3. an amino acid sequence having at least 95% sequence identity to the sequence of SEQ ID NO: 2 from amino acid 22 to 280, or to the sequence of SEQ ID NO: 6 from amino acid 26 to 283, or to the sequence of SEQ ID NO: 8 from amino acid 29 to 287,
      ii. a nucleic acid sequence having the sequence of any one of SEQ ID NOs: 1, 5 and 7;

iii. a nucleic acid sequence having the sequence of SEQ ID NO: 1 from nucleotide 64 to 840, or the sequence of SEQ ID NO: 5 from nucleotide 76 to 849, or the sequence of SEQ ID NO: 7 from nucleotide 85 to 861 and, optionally, c. a transcription termination and polyadenylation region.

2. The chimeric gene of claim 1, wherein said heterologous promoter is a constitutive promoter, a seed-specific promoter, a stem-specific promoter or a fiber-specific promoter.

3. A host cell comprising the chimeric gene of claim 1.

4. The cell of claim 3 which is a plant cell.

5. A transgenic plant, plant part or seed comprising the chimeric gene of claim 1.

6. The transgenic plant of claim 5 which is selected from cotton, wheat, canola and other oilseed rape, rice, corn, soy bean, sorghum, sunflower, tobacco, sugar beet, maize, barley, tomato, mango, peach, apple, pear, strawberry, banana, melon, potato, carrot, lettuce, cabbage, onion, sugar cane, pea, field beans, poplar, grape, citrus, alfalfa, rye, oats, turf and forage grasses, flax, nut producing plants and wood producing plants.

7. A method of producing a transgenic plant comprising providing a chimeric gene according to claim 1 introducing said chimeric gene or said vector into a plant.

8. A method of altering at least one fiber property in a fiber-producing plant or for strengthening plant cell walls of a plant comprising expressing the chimeric gene according to claim 1 in said fiber-producing plant or plant.

9. The method of claim 8, wherein said fiber property is selected from fiber strength and resistance to enzymatic digestion.

10. The method of claim 8, wherein strengthening a plant includes strengthening its stem, increasing resistance to lodging and increasing resistance to infection by pathogens.

11. The method of claim 8 further comprising growing said plant until seed is produced.

12. A method for producing a cellulosic material with improved properties, said method comprising providing a plant of claim 5 and harvesting the cellulosic material from said plant.

13. A method of producing food, feed, or an industrial product comprising
    a) obtaining the plant or a part thereof, of claim 5; and
    b) preparing the food, feed or industrial product from the plant or part thereof.

14. The method of claim 13 wherein
    a) the food or feed is oil, meal, grain, starch, flour or protein; or
    b) the industrial product is biofuel, fiber, industrial chemicals, a pharmaceutical or a nutraceutical.

15. The chimeric gene of claim 1, wherein said nucleic acid sequence encoding a protein having cellulose:xyloglucan endotransglucosylase activity comprises:
    a. an amino acid sequence having at least 98% sequence identity to the sequence of any one of SEQ ID NOs: 2, 6 and 8, or
    b. an amino acid sequence having at least 98% sequence identity to the sequence of SEQ ID NO: 2 from amino acid 22 to 280, or to the sequence of SEQ ID NO: 6 from amino acid 26 to 283, or to the sequence of SEQ ID NO: 8 from amino acid 29 to 287.

* * * * *

SEQUENCE LISTING

```
<160> NUMBER OF SEQ ID NOS: 8

<210> SEQ ID NO 1
<211> LENGTH: 843
<212> TYPE: DNA
<213> ORGANISM: Equisetum fluviatile
<220> FEATURE:
<221> NAME/KEY: CDS
<222> LOCATION: (1)..(843)
<220> FEATURE:
<221> NAME/KEY: sig_peptide
<222> LOCATION: (1)..(63)

<400> SEQUENCE: 1 atg ctg ggt ctg gtg ttt gga atg ttg gtg atc atg ctg gcg tct cca      48
Met Leu Gly Leu Val Phe Gly Met Leu Val Ile Met Leu Ala Ser Pro
1               5                   10                  15 aaa tta gca atg gca ggt ttc tat ggg gac ttt cag gta gaa ccg gtt      96
Lys Leu Ala Met Ala Gly Phe Tyr Gly Asp Phe Gln Val Glu Pro Val
                20                  25                  30 ccc gac cac gta ata atc caa agc gat agc ctc ctc caa ctc acc atg     144
Pro Asp His Val Ile Ile Gln Ser Asp Ser Leu Leu Gln Leu Thr Met
            35                  40                  45 gat aag aac tct ggt ggc tca gtt gtc tcc aaa agt aat tat ctg ttt     192
Asp Lys Asn Ser Gly Gly Ser Val Val Ser Lys Ser Asn Tyr Leu Phe
        50                  55                  60 ggc tac ttc aac atg aag atg aag ctc ata tca gga aac tct gca ggg     240
Gly Tyr Phe Asn Met Lys Met Lys Leu Ile Ser Gly Asn Ser Ala Gly
65                  70                  75                  80 aca gta acc aca ttc tat atc ttc tct gat gaa gca aac cac gat gag     288
Thr Val Thr Thr Phe Tyr Ile Phe Ser Asp Glu Ala Asn His Asp Glu
                85                  90                  95
```

| | | |
|---|---|---|
| ata gac ttt gag ttc ctt ggc aac tat tca ggg gat cct tat ctt ttg<br>Ile Asp Phe Glu Phe Leu Gly Asn Tyr Ser Gly Asp Pro Tyr Leu Leu<br>100 105 110 | | 336 |
| cat act aat att ttt gca agt ggt gtt gga aat aga gaa caa caa ttt<br>His Thr Asn Ile Phe Ala Ser Gly Val Gly Asn Arg Glu Gln Gln Phe<br>115 120 125 | | 384 |
| ttt ctg tgg ttt gac cct aca gct gac ttc cat gat tat aca ata att<br>Phe Leu Trp Phe Asp Pro Thr Ala Asp Phe His Asp Tyr Thr Ile Ile<br>130 135 140 | | 432 |
| tgg aac cct caa caa ata ttg ttt ctt gtt gat gga agg gct gtt aga<br>Trp Asn Pro Gln Gln Ile Leu Phe Leu Val Asp Gly Arg Ala Val Arg<br>145 150 155 160 | | 480 |
| tct ttt ccg aat aat gag gct ata ggt gtc cct tac tta aaa agt caa<br>Ser Phe Pro Asn Asn Glu Ala Ile Gly Val Pro Tyr Leu Lys Ser Gln<br>165 170 175 | | 528 |
| tgg atg aat gta cat tta agt ctt tgg aat ggc gag act tgg gcc aca<br>Trp Met Asn Val His Leu Ser Leu Trp Asn Gly Glu Thr Trp Ala Thr<br>180 185 190 | | 576 |
| cta gga ggg ttg aga agg ata gat tgg aat tca gcc cct ttt gta gct<br>Leu Gly Gly Leu Arg Arg Ile Asp Trp Asn Ser Ala Pro Phe Val Ala<br>195 200 205 | | 624 |
| tcc tat tct act ttt gta gga gac tca tgc ttc gat agc gca gat tcc<br>Ser Tyr Ser Thr Phe Val Gly Asp Ser Cys Phe Asp Ser Ala Asp Ser<br>210 215 220 | | 672 |
| ccg tgc atg gcc tca aaa tgg tgg aac caa gct gca tat caa tct tta<br>Pro Cys Met Ala Ser Lys Trp Trp Asn Gln Ala Ala Tyr Gln Ser Leu<br>225 230 235 240 | | 720 |
| agc aca agt gat gcc agc agt att caa tgg gtt agg gaa aat tat ctc<br>Ser Thr Ser Asp Ala Ser Ser Ile Gln Trp Val Arg Glu Asn Tyr Leu<br>245 250 255 | | 768 |
| aaa tat gac tat tgt tat gat aca aaa ctc tat ccg aac ggc ttt ccc<br>Lys Tyr Asp Tyr Cys Tyr Asp Thr Lys Leu Tyr Pro Asn Gly Phe Pro<br>260 265 270 | | 816 |
| aga gaa tgc tca aac cgt ggt ttc tag<br>Arg Glu Cys Ser Asn Arg Gly Phe<br>275 280 | | 843 |

<210> SEQ ID NO 2
<211> LENGTH: 280
<212> TYPE: PRT
<213> ORGANISM: Equisetum fluviatile

<400> SEQUENCE: 2

Met Leu Gly Leu Val Phe Gly Met Leu Val Ile Met Leu Ala Ser Pro
1               5                   10                  15

Lys Leu Ala Met Ala Gly Phe Tyr Gly Asp Phe Gln Val Glu Pro Val
            20                  25                  30

Pro Asp His Val Ile Ile Gln Ser Asp Ser Leu Leu Gln Leu Thr Met
        35                  40                  45

Asp Lys Asn Ser Gly Gly Ser Val Val Ser Lys Ser Asn Tyr Leu Phe
    50                  55                  60

Gly Tyr Phe Asn Met Lys Met Lys Leu Ile Ser Gly Asn Ser Ala Gly
65                  70                  75                  80

Thr Val Thr Thr Phe Tyr Ile Ser Asp Glu Ala Asn His Asp Glu
            85                  90                  95

Ile Asp Phe Glu Phe Leu Gly Asn Tyr Ser Gly Asp Pro Tyr Leu Leu
            100                 105                 110

His Thr Asn Ile Phe Ala Ser Gly Val Gly Asn Arg Glu Gln Gln Phe
        115                 120                 125

```
Phe Leu Trp Phe Asp Pro Thr Ala Asp Phe His Asp Tyr Thr Ile Ile
    130                 135                 140
Trp Asn Pro Gln Gln Ile Leu Phe Leu Val Asp Gly Arg Ala Val Arg
145                 150                 155                 160
Ser Phe Pro Asn Asn Glu Ala Ile Gly Val Pro Tyr Leu Lys Ser Gln
                165                 170                 175
Trp Met Asn Val His Leu Ser Leu Trp Asn Gly Glu Thr Trp Ala Thr
            180                 185                 190
Leu Gly Gly Leu Arg Arg Ile Asp Trp Asn Ser Ala Pro Phe Val Ala
        195                 200                 205
Ser Tyr Ser Thr Phe Val Gly Asp Ser Cys Phe Asp Ser Ala Asp Ser
    210                 215                 220
Pro Cys Met Ala Ser Lys Trp Trp Asn Gln Ala Ala Tyr Gln Ser Leu
225                 230                 235                 240
Ser Thr Ser Asp Ala Ser Ser Ile Gln Trp Val Arg Glu Asn Tyr Leu
                245                 250                 255
Lys Tyr Asp Tyr Cys Tyr Asp Thr Lys Leu Tyr Pro Asn Gly Phe Pro
            260                 265                 270
Arg Glu Cys Ser Asn Arg Gly Phe
        275                 280

<210> SEQ ID NO 3
<211> LENGTH: 1122
<212> TYPE: DNA
<213> ORGANISM: artificial
<220> FEATURE:
<223> OTHER INFORMATION: coding sequence CXE fusion protein for
      expression in Pichia
<220> FEATURE:
<221> NAME/KEY: CDS
<222> LOCATION: (1)..(1122)
<220> FEATURE:
<221> NAME/KEY: alpha factor signal sequence
<222> LOCATION: (1)..(267)
<220> FEATURE:
<221> NAME/KEY: HTG
<222> LOCATION: (274)..(1050)
<220> FEATURE:
<221> NAME/KEY: c-myc epitope
<222> LOCATION: (1057)..(1086)
<220> FEATURE:
<221> NAME/KEY: polyhistidine tag
<222> LOCATION: (1102)..(1119)

<400> SEQUENCE: 3 atg aga ttt cct tca att ttt act gct gtt tta ttc gca gca tcc tcc      48
Met Arg Phe Pro Ser Ile Phe Thr Ala Val Leu Phe Ala Ala Ser Ser
1               5                   10                  15 gca tta gct gct cca gtc aac act aca aca gaa gat gaa acg gca caa      96
Ala Leu Ala Ala Pro Val Asn Thr Thr Thr Glu Asp Glu Thr Ala Gln
                20                  25                  30 att ccg gct gaa gct gtc atc ggt tac tca gat tta gaa ggg gat ttc     144
Ile Pro Ala Glu Ala Val Ile Gly Tyr Ser Asp Leu Glu Gly Asp Phe
            35                  40                  45 gat gtt gct gtt ttg cca ttt tcc aac agc aca aat aac ggg tta ttg     192
Asp Val Ala Val Leu Pro Phe Ser Asn Ser Thr Asn Asn Gly Leu Leu
        50                  55                  60 ttt ata aat act act att gcc agc att gct gct aaa gaa gaa ggg gta     240
Phe Ile Asn Thr Thr Ile Ala Ser Ile Ala Ala Lys Glu Glu Gly Val
65                  70                  75                  80 tct ctc gag aaa aga gag gct gaa gct gaa ttc ggt ttc tat ggg gac     288
Ser Leu Glu Lys Arg Glu Ala Glu Ala Glu Phe Gly Phe Tyr Gly Asp
                85                  90                  95
```

```
ttt cag gta gaa ccg gtt ccc gac cac gtg ata atc caa agc gat agc    336
Phe Gln Val Glu Pro Val Pro Asp His Val Ile Ile Gln Ser Asp Ser
            100                 105                 110 ctc ctc caa ctc acc atg gat aag aac tct ggt ggc tca gtt gtc tcc    384
Leu Leu Gln Leu Thr Met Asp Lys Asn Ser Gly Gly Ser Val Val Ser
        115                 120                 125 aaa agt aat tat ctg ttt ggc tac ttc aac atg aag atg aag ctc ata    432
Lys Ser Asn Tyr Leu Phe Gly Tyr Phe Asn Met Lys Met Lys Leu Ile
    130                 135                 140 tca gga aac tct gca ggg aca gta acc aca ttc tat atc ttc tct gat    480
Ser Gly Asn Ser Ala Gly Thr Val Thr Thr Phe Tyr Ile Phe Ser Asp
145                 150                 155                 160 gaa gca aac cac gat gag ata gac ttt gag ttc ctt ggc aac tat tca    528
Glu Ala Asn His Asp Glu Ile Asp Phe Glu Phe Leu Gly Asn Tyr Ser
                165                 170                 175 ggg gat cct tat ctt ttg cat act aat att ttt gca agt ggt gtt gga    576
Gly Asp Pro Tyr Leu Leu His Thr Asn Ile Phe Ala Ser Gly Val Gly
            180                 185                 190 aat aga gaa caa caa ttt ttt ctg tgg ttt gac cct aca gct gac ttc    624
Asn Arg Glu Gln Gln Phe Phe Leu Trp Phe Asp Pro Thr Ala Asp Phe
        195                 200                 205 cat gat tat aca ata att tgg aac cct caa caa ata ttg ttt ctt gtt    672
His Asp Tyr Thr Ile Ile Trp Asn Pro Gln Gln Ile Leu Phe Leu Val
    210                 215                 220 gat gga agg gct gtt aga tct ttt ccg aat aat gag gct ata ggt gtc    720
Asp Gly Arg Ala Val Arg Ser Phe Pro Asn Asn Glu Ala Ile Gly Val
225                 230                 235                 240 cct tac tta aaa agt caa tgg atg aat gta cat tta agt ctt tgg aat    768
Pro Tyr Leu Lys Ser Gln Trp Met Asn Val His Leu Ser Leu Trp Asn
                245                 250                 255 ggc gag act tgg gcc aca cta gga ggg ttg aga agg ata gat tgg aat    816
Gly Glu Thr Trp Ala Thr Leu Gly Gly Leu Arg Arg Ile Asp Trp Asn
            260                 265                 270 tca gcc cct ttt gta gct tcc tat tct act ttt gta gga gac tca tgc    864
Ser Ala Pro Phe Val Ala Ser Tyr Ser Thr Phe Val Gly Asp Ser Cys
        275                 280                 285 ttc gat agc gca gat tcc ccg tgc atg gcc tca aaa tgg tgg aac caa    912
Phe Asp Ser Ala Asp Ser Pro Cys Met Ala Ser Lys Trp Trp Asn Gln
    290                 295                 300 gct gca tat caa tct tta agc aca agt gat gcc agc agt att caa tgg    960
Ala Ala Tyr Gln Ser Leu Ser Thr Ser Asp Ala Ser Ser Ile Gln Trp
305                 310                 315                 320 gtt agg gaa aat tat ctc aaa tat gac tat tgt tat gat aca aaa ctc   1008
Val Arg Glu Asn Tyr Leu Lys Tyr Asp Tyr Cys Tyr Asp Thr Lys Leu
                325                 330                 335 tat ccg aac ggc ttt ccc aga gaa tgc tca aac cgt ggt ttc tat cta   1056
Tyr Pro Asn Gly Phe Pro Arg Glu Cys Ser Asn Arg Gly Phe Tyr Leu
            340                 345                 350 gaa caa aaa ctc atc tca gaa gag gat ctg aat agc gcc gtc gac cat   1104
Glu Gln Lys Leu Ile Ser Glu Glu Asp Leu Asn Ser Ala Val Asp His
        355                 360                 365 cat cat cat cat cat tga                                           1122
His His His His His
    370
```

<210> SEQ ID NO 4
<211> LENGTH: 373
<212> TYPE: PRT
<213> ORGANISM: artificial
<220> FEATURE:
<223> OTHER INFORMATION: Synthetic Construct

<400> SEQUENCE: 4

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe Gly Phe Tyr Gly Asp
                85                  90                  95

Phe Gln Val Glu Pro Val Pro Asp His Val Ile Ile Gln Ser Asp Ser
            100                 105                 110

Leu Leu Gln Leu Thr Met Asp Lys Asn Ser Gly Gly Ser Val Val Ser
        115                 120                 125

Lys Ser Asn Tyr Leu Phe Gly Tyr Phe Asn Met Lys Met Lys Leu Ile
130                 135                 140

Ser Gly Asn Ser Ala Gly Thr Val Thr Thr Phe Tyr Ile Phe Ser Asp
145                 150                 155                 160

Glu Ala Asn His Asp Glu Ile Asp Phe Glu Phe Leu Gly Asn Tyr Ser
                165                 170                 175

Gly Asp Pro Tyr Leu Leu His Thr Asn Ile Phe Ala Ser Gly Val Gly
            180                 185                 190

Asn Arg Glu Gln Gln Phe Phe Leu Trp Phe Asp Pro Thr Ala Asp Phe
        195                 200                 205

His Asp Tyr Thr Ile Ile Trp Asn Pro Gln Gln Ile Leu Phe Leu Val
    210                 215                 220

Asp Gly Arg Ala Val Arg Ser Phe Pro Asn Asn Glu Ala Ile Gly Val
225                 230                 235                 240

Pro Tyr Leu Lys Ser Gln Trp Met Asn Val His Leu Ser Leu Trp Asn
                245                 250                 255

Gly Glu Thr Trp Ala Thr Leu Gly Gly Leu Arg Arg Ile Asp Trp Asn
            260                 265                 270

Ser Ala Pro Phe Val Ala Ser Tyr Ser Thr Phe Val Gly Asp Ser Cys
        275                 280                 285

Phe Asp Ser Ala Asp Ser Pro Cys Met Ala Ser Lys Trp Trp Asn Gln
    290                 295                 300

Ala Ala Tyr Gln Ser Leu Ser Thr Ser Asp Ala Ser Ser Ile Gln Trp
305                 310                 315                 320

Val Arg Glu Asn Tyr Leu Lys Tyr Asp Tyr Cys Tyr Asp Thr Lys Leu
                325                 330                 335

Tyr Pro Asn Gly Phe Pro Arg Glu Cys Ser Asn Arg Gly Phe Tyr Leu
            340                 345                 350

Glu Gln Lys Leu Ile Ser Glu Glu Asp Leu Asn Ser Ala Val Asp His
        355                 360                 365

His His His His
    370
```

<210> SEQ ID NO 5
<211> LENGTH: 852
<212> TYPE: DNA
<213> ORGANISM: Equisetum hyemale

```
<220> FEATURE:
<221> NAME/KEY: sig_peptide
<222> LOCATION: (1)..(75)
<220> FEATURE:
<221> NAME/KEY: CDS
<222> LOCATION: (1)..(852)

<400> SEQUENCE: 5 atg aag aag aag att gga atg gtg ctg ctt ttg ggg ctt ttc atg atc      48
Met Lys Lys Lys Ile Gly Met Val Leu Leu Leu Gly Leu Phe Met Ile
1               5                   10                  15 atc ata gcg tct ccc aaa gca gag gca aat ttc tat caa gat ttc gtc      96
Ile Ile Ala Ser Pro Lys Ala Glu Ala Asn Phe Tyr Gln Asp Phe Val
                20                  25                  30 gta gtt aca gct cct gac cat gtc caa atc ctt aat gat aac ctc ctc     144
Val Val Thr Ala Pro Asp His Val Gln Ile Leu Asn Asp Asn Leu Leu
            35                  40                  45 cag ctt acc atg gat aag aat act ggt agc tca att agc tcc acc agt     192
Gln Leu Thr Met Asp Lys Asn Thr Gly Ser Ser Ile Ser Ser Thr Ser
        50                  55                  60 aaa tac ctg ttt ggc tac ttc aac atg agg atg aag ctc ata gca ggc     240
Lys Tyr Leu Phe Gly Tyr Phe Asn Met Arg Met Lys Leu Ile Ala Gly
65                  70                  75                  80 aac tct gca ggg aca gtg acc acc ttc tat ctc ttc tcc agt gaa ccc     288
Asn Ser Ala Gly Thr Val Thr Thr Phe Tyr Leu Phe Ser Ser Glu Pro
                85                  90                  95 aac cat gat gag cta gac ttt gag ttc ctt ggc aat ctt tca ggg gaa     336
Asn His Asp Glu Leu Asp Phe Glu Phe Leu Gly Asn Leu Ser Gly Glu
                100                 105                 110 cct tat gtt ttg cat aca aat gtt ttt gca agt ggt gtt gga aat aga     384
Pro Tyr Val Leu His Thr Asn Val Phe Ala Ser Gly Val Gly Asn Arg
            115                 120                 125 gaa caa caa ttt ttt ctg tgg ttt gac cct aca act gac ttc cac gac     432
Glu Gln Gln Phe Phe Leu Trp Phe Asp Pro Thr Thr Asp Phe His Asp
        130                 135                 140 tat aca ata att tgg aac cct caa caa gta ttg ttt gtt gtt gat gga     480
Tyr Thr Ile Ile Trp Asn Pro Gln Gln Val Leu Phe Val Val Asp Gly
145                 150                 155                 160 agg act gtt aga tct ttc cca aat aat gag gct ata ggt gtc cct tac     528
Arg Thr Val Arg Ser Phe Pro Asn Asn Glu Ala Ile Gly Val Pro Tyr
                165                 170                 175 tta aaa agt caa tgg atg aat gta tat gca agc ctt tgg aat ggt gag     576
Leu Lys Ser Gln Trp Met Asn Val Tyr Ala Ser Leu Trp Asn Gly Glu
                180                 185                 190 tct tgg gcc aca cta gga ggg ctg ata aag ata gat tgg agt gta tcc     624
Ser Trp Ala Thr Leu Gly Gly Leu Ile Lys Ile Asp Trp Ser Val Ser
            195                 200                 205 cct ttt gtg gct tcc tat gct gat ttt gca gca gac tca tgc ttt gat     672
Pro Phe Val Ala Ser Tyr Ala Asp Phe Ala Ala Asp Ser Cys Phe Asp
        210                 215                 220 agt gca gat tcc tca tgc atg gcc aca aag tgg tgg aac caa cct gca     720
Ser Ala Asp Ser Ser Cys Met Ala Thr Lys Trp Trp Asn Gln Pro Ala
225                 230                 235                 240 tat caa ttt tta agc aca aat gat gca agc agt att caa tgg gtt agg     768
Tyr Gln Phe Leu Ser Thr Asn Asp Ala Ser Ser Ile Gln Trp Val Arg
                245                 250                 255
```

```
gca aat tat ctc aaa tac gac tat tgt tat gat acg gaa ctc tat cca    816
Ala Asn Tyr Leu Lys Tyr Asp Tyr Cys Tyr Asp Thr Glu Leu Tyr Pro
        260                 265                 270 act cct ccc atc gaa tgt cag aac cgt ggc ttc tag                    852
Thr Pro Pro Ile Glu Cys Gln Asn Arg Gly Phe
        275                 280
```

<210> SEQ ID NO 6
<211> LENGTH: 283
<212> TYPE: PRT
<213> ORGANISM: Equisetum hyemale

<400> SEQUENCE: 6

```
Met Lys Lys Lys Ile Gly Met Val Leu Leu Leu Gly Leu Phe Met Ile
1               5                   10                  15

Ile Ile Ala Ser Pro Lys Ala Glu Ala Asn Phe Tyr Gln Asp Phe Val
            20                  25                  30

Val Val Thr Ala Pro Asp His Val Gln Ile Leu Asn Asp Asn Leu Leu
        35                  40                  45

Gln Leu Thr Met Asp Lys Asn Thr Gly Ser Ser Ile Ser Ser Thr Ser
    50                  55                  60

Lys Tyr Leu Phe Gly Tyr Phe Asn Met Arg Met Lys Leu Ile Ala Gly
65                  70                  75                  80

Asn Ser Ala Gly Thr Val Thr Thr Phe Tyr Leu Phe Ser Ser Glu Pro
                85                  90                  95

Asn His Asp Glu Leu Asp Phe Glu Phe Leu Gly Asn Leu Ser Gly Glu
            100                 105                 110

Pro Tyr Val Leu His Thr Asn Val Phe Ala Ser Gly Val Gly Asn Arg
        115                 120                 125

Glu Gln Gln Phe Phe Leu Trp Phe Asp Pro Thr Thr Asp Phe His Asp
    130                 135                 140

Tyr Thr Ile Ile Trp Asn Pro Gln Gln Val Leu Phe Val Val Asp Gly
145                 150                 155                 160

Arg Thr Val Arg Ser Phe Pro Asn Asn Glu Ala Ile Gly Val Pro Tyr
                165                 170                 175

Leu Lys Ser Gln Trp Met Asn Val Tyr Ala Ser Leu Trp Asn Gly Glu
            180                 185                 190

Ser Trp Ala Thr Leu Gly Gly Leu Ile Lys Ile Asp Trp Ser Val Ser
        195                 200                 205

Pro Phe Val Ala Ser Tyr Ala Asp Phe Ala Ala Asp Ser Cys Phe Asp
    210                 215                 220

Ser Ala Asp Ser Ser Cys Met Ala Thr Lys Trp Trp Asn Gln Pro Ala
225                 230                 235                 240

Tyr Gln Phe Leu Ser Thr Asn Asp Ala Ser Ser Ile Gln Trp Val Arg
                245                 250                 255

Ala Asn Tyr Leu Lys Tyr Asp Tyr Cys Tyr Asp Thr Glu Leu Tyr Pro
            260                 265                 270

Thr Pro Pro Ile Glu Cys Gln Asn Arg Gly Phe
        275                 280
```

<210> SEQ ID NO 7
<211> LENGTH: 864
<212> TYPE: DNA
<213> ORGANISM: Equisetum diffusum
<220> FEATURE:
<221> NAME/KEY: sig_peptide
<222> LOCATION: (1)..(84)
<220> FEATURE:
<221> NAME/KEY: CDS
<222> LOCATION: (1)..(864)

<400> SEQUENCE: 7

| | | | | | | | | | | | | | | | | |
|---|---|---|---|---|---|---|---|---|---|---|---|---|---|---|---|---|
| atg | aag | aag | aag | acc | gcg | tcg | atg | ctg | ggt | ttg | gcg | ttt | ggg | atg | ttg | 48 |
| Met | Lys | Lys | Lys | Thr | Ala | Ser | Met | Leu | Gly | Leu | Ala | Phe | Gly | Met | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttg | atc | atg | ctg | gcg | tct | cca | aaa | tta | gca | ata | gca | ggt | ttc | tat | gag | 96 |
| Leu | Ile | Met | Leu | Ala | Ser | Pro | Lys | Leu | Ala | Ile | Ala | Gly | Phe | Tyr | Glu | |
| | | 20 | | | | | 25 | | | | | 30 | | | | |

| | | | | | | | | | | | | | | | | |
|---|---|---|---|---|---|---|---|---|---|---|---|---|---|---|---|---|
| gac | ttt | gac | gta | gat | cca | cct | ccc | gac | cac | gtg | ata | atc | caa | agt | gat | 144 |
| Asp | Phe | Asp | Val | Asp | Pro | Pro | Pro | Asp | His | Val | Ile | Ile | Gln | Ser | Asp | |
| | | 35 | | | | | 40 | | | | | 45 | | | | |

| | | | | | | | | | | | | | | | | |
|---|---|---|---|---|---|---|---|---|---|---|---|---|---|---|---|---|
| agc | ctc | ctc | gaa | ctc | acc | atg | gat | aag | aac | tct | ggt | agc | aca | gtt | gtc | 192 |
| Ser | Leu | Leu | Glu | Leu | Thr | Met | Asp | Lys | Asn | Ser | Gly | Ser | Thr | Val | Val | |
| 50 | | | | | 55 | | | | | 60 | | | | | | |

| | | | | | | | | | | | | | | | | |
|---|---|---|---|---|---|---|---|---|---|---|---|---|---|---|---|---|
| tcc | acc | cgt | aaa | tat | ctg | ttt | ggc | tac | ttc | aac | atg | aag | atg | aag | ctc | 240 |
| Ser | Thr | Arg | Lys | Tyr | Leu | Phe | Gly | Tyr | Phe | Asn | Met | Lys | Met | Lys | Leu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ata | tca | ggc | aac | tct | gca | ggg | aca | gta | acc | aca | ttc | tat | atc | ttc | tct | 288 |
| Ile | Ser | Gly | Asn | Ser | Ala | Gly | Thr | Val | Thr | Thr | Phe | Tyr | Ile | Phe | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| gag | gaa | gca | aac | cac | gat | gag | ata | gac | ttt | gag | ttc | ctt | ggc | aac | tat | 336 |
| Glu | Glu | Ala | Asn | His | Asp | Glu | Ile | Asp | Phe | Glu | Phe | Leu | Gly | Asn | Tyr | |
| | | | 100 | | | | | 105 | | | | | 110 | | | |

| | | | | | | | | | | | | | | | | |
|---|---|---|---|---|---|---|---|---|---|---|---|---|---|---|---|---|
| tca | ggg | gat | cct | tat | ctt | ttg | cat | act | aat | att | ttt | gca | agt | ggt | gtt | 384 |
| Ser | Gly | Asp | Pro | Tyr | Leu | Leu | His | Thr | Asn | Ile | Phe | Ala | Ser | Gly | Val | |
| | | | 115 | | | | | 120 | | | | | 125 | | | |

| | | | | | | | | | | | | | | | | |
|---|---|---|---|---|---|---|---|---|---|---|---|---|---|---|---|---|
| gga | aat | aga | gaa | caa | caa | ttt | ttt | ctg | tgg | ttt | gac | cct | aca | gct | gac | 432 |
| Gly | Asn | Arg | Glu | Gln | Gln | Phe | Phe | Leu | Trp | Phe | Asp | Pro | Thr | Ala | Asp | |
| | 130 | | | | | 135 | | | | | 140 | | | | | |

| | | | | | | | | | | | | | | | | |
|---|---|---|---|---|---|---|---|---|---|---|---|---|---|---|---|---|
| ttc | cat | gat | tat | aca | ata | att | tgg | aac | cct | caa | caa | ata | ttg | ttt | ctt | 480 |
| Phe | His | Asp | Tyr | Thr | Ile | Ile | Trp | Asn | Pro | Gln | Gln | Ile | Leu | Phe | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gtt | gat | gga | agg | gct | gtt | aga | tct | ttt | ccg | aat | aat | gag | gct | ata | ggt | 528 |
| Val | Asp | Gly | Arg | Ala | Val | Arg | Ser | Phe | Pro | Asn | Asn | Glu | Ala | Ile | Gly | |
| | | | | 165 | | | | | 170 | | | | | 175 | | |

| | | | | | | | | | | | | | | | | |
|---|---|---|---|---|---|---|---|---|---|---|---|---|---|---|---|---|
| gtc | cct | tac | tta | aaa | agt | caa | tgg | atg | aat | gta | cat | tta | agt | ctt | tgg | 576 |
| Val | Pro | Tyr | Leu | Lys | Ser | Gln | Trp | Met | Asn | Val | His | Leu | Ser | Leu | Trp | |
| | | | | 180 | | | | | 185 | | | | | 190 | | |

| | | | | | | | | | | | | | | | | |
|---|---|---|---|---|---|---|---|---|---|---|---|---|---|---|---|---|
| aat | ggc | gag | act | tgg | gcc | aca | cta | gga | ggg | ttg | aga | agg | ata | gat | tgg | 624 |
| Asn | Gly | Glu | Thr | Trp | Ala | Thr | Leu | Gly | Gly | Leu | Arg | Arg | Ile | Asp | Trp | |
| | | 195 | | | | | 200 | | | | | 205 | | | | |

| | | | | | | | | | | | | | | | | |
|---|---|---|---|---|---|---|---|---|---|---|---|---|---|---|---|---|
| aat | tca | gcc | cct | ttt | gta | gct | tcc | tat | tct | act | ttt | gta | gga | gac | tca | 672 |
| Asn | Ser | Ala | Pro | Phe | Val | Ala | Ser | Tyr | Ser | Thr | Phe | Val | Gly | Asp | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| tgc | ttc | gat | agc | gca | gat | tcc | ccg | tgc | atg | gcc | tca | aaa | tgg | tgg | aac | 720 |
| Cys | Phe | Asp | Ser | Ala | Asp | Ser | Pro | Cys | Met | Ala | Ser | Lys | Trp | Trp | Asn | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| caa | gct | gca | tat | caa | tct | tta | agc | aca | agt | gat | gcc | agc | agt | att | caa | 768 |
| Gln | Ala | Ala | Tyr | Gln | Ser | Leu | Ser | Thr | Ser | Asp | Ala | Ser | Ser | Ile | Gln | |
| | | | | 245 | | | | | 250 | | | | | 255 | | |

| | | | | | | | | | | | | | | | | |
|---|---|---|---|---|---|---|---|---|---|---|---|---|---|---|---|---|
| tgg | gtt | agg | gca | aat | tat | ctc | aaa | tat | gac | tat | tgt | tat | gat | aca | aaa | 816 |
| Trp | Val | Arg | Ala | Asn | Tyr | Leu | Lys | Tyr | Asp | Tyr | Cys | Tyr | Asp | Thr | Lys | |
| | | | | 260 | | | | | 265 | | | | | 270 | | |

```
ctc tat ccg aac ggc ttt ccc agc gaa tgc tca aac cgt ggt ttc tag    864
Leu Tyr Pro Asn Gly Phe Pro Ser Glu Cys Ser Asn Arg Gly Phe
        275             280                 285
```

<210> SEQ ID NO 8
<211> LENGTH: 287
<212> TYPE: PRT
<213> ORGANISM: Equisetum diffusum

<400> SEQUENCE: 8

```
Met Lys Lys Lys Thr Ala Ser Met Leu Gly Leu Ala Phe Gly Met Leu
1               5                   10                  15

Leu Ile Met Leu Ala Ser Pro Lys Leu Ala Ile Ala Gly Phe Tyr Glu
            20                  25                  30

Asp Phe Asp Val Asp Pro Pro Asp His Val Ile Ile Gln Ser Asp
            35                  40                  45

Ser Leu Leu Glu Leu Thr Met Asp Lys Asn Ser Gly Ser Thr Val Val
    50                  55                  60

Ser Thr Arg Lys Tyr Leu Phe Gly Tyr Phe Asn Met Lys Met Lys Leu
65                  70                  75                  80

Ile Ser Gly Asn Ser Ala Gly Thr Val Thr Thr Phe Tyr Ile Phe Ser
                85                  90                  95

Glu Glu Ala Asn His Asp Glu Ile Asp Phe Glu Phe Leu Gly Asn Tyr
            100                 105                 110

Ser Gly Asp Pro Tyr Leu Leu His Thr Asn Ile Phe Ala Ser Gly Val
            115                 120                 125

Gly Asn Arg Glu Gln Gln Phe Phe Leu Trp Phe Asp Pro Thr Ala Asp
    130                 135                 140

Phe His Asp Tyr Thr Ile Ile Trp Asn Pro Gln Gln Ile Leu Phe Leu
145                 150                 155                 160

Val Asp Gly Arg Ala Val Arg Ser Phe Pro Asn Asn Glu Ala Ile Gly
                165                 170                 175

Val Pro Tyr Leu Lys Ser Gln Trp Met Asn Val His Leu Ser Leu Trp
            180                 185                 190

Asn Gly Glu Thr Trp Ala Thr Leu Gly Gly Leu Arg Arg Ile Asp Trp
    195                 200                 205

Asn Ser Ala Pro Phe Val Ala Ser Tyr Ser Thr Phe Val Gly Asp Ser
    210                 215                 220

Cys Phe Asp Ser Ala Asp Ser Pro Cys Met Ala Ser Lys Trp Trp Asn
225                 230                 235                 240

Gln Ala Ala Tyr Gln Ser Leu Ser Thr Ser Asp Ala Ser Ser Ile Gln
                245                 250                 255

Trp Val Arg Ala Asn Tyr Leu Lys Tyr Asp Tyr Cys Tyr Asp Thr Lys
            260                 265                 270

Leu Tyr Pro Asn Gly Phe Pro Ser Glu Cys Ser Asn Arg Gly Phe
        275             280                 285
```